United States Patent
Tsai et al.

(10) Patent No.: US 10,265,336 B2
(45) Date of Patent: Apr. 23, 2019

(54) COMPOSITIONS CONTAINING TANNIC ACIDS AND USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW); Tien-Lan Hsieh, New Taipei (TW); Yi-Wen Mao, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 15/834,428

(22) Filed: Dec. 7, 2017

(65) Prior Publication Data

US 2018/0092935 A1 Apr. 5, 2018

Related U.S. Application Data

(63) Continuation-in-part of application No. PCT/CN2017/078361, filed on Mar. 28, 2017.

(60) Provisional application No. 62/458,216, filed on Feb. 13, 2017, provisional application No. 62/313,946, filed on Mar. 28, 2016.

(51) Int. Cl.

| | |
|---|---|
| *A61P 1/16* | (2006.01) |
| *A61P 5/50* | (2006.01) |
| *A61P 9/00* | (2006.01) |
| *C07H 1/08* | (2006.01) |
| *A23L 33/00* | (2016.01) |
| *A23L 33/10* | (2016.01) |
| *A61K 31/00* | (2006.01) |
| *A61K 36/22* | (2006.01) |
| *A61K 36/48* | (2006.01) |
| *A61K 36/49* | (2006.01) |
| *A61K 36/82* | (2006.01) |
| *A61K 36/87* | (2006.01) |
| *A61K 38/26* | (2006.01) |
| *A61K 45/06* | (2006.01) |
| *A61P 11/00* | (2006.01) |
| *A61P 11/06* | (2006.01) |
| *A61P 25/16* | (2006.01) |
| *A61P 25/18* | (2006.01) |
| *A61P 25/24* | (2006.01) |
| *A61P 25/28* | (2006.01) |
| *A61K 31/7024* | (2006.01) |
| *C07H 13/08* | (2006.01) |
| *A61P 25/30* | (2006.01) |
| *A61K 36/185* | (2006.01) |
| *A23L 33/105* | (2016.01) |

(52) U.S. Cl.
CPC .......... *A61K 31/7024* (2013.01); *A23L 33/10* (2016.08); *A23L 33/105* (2016.08); *A23L 33/30* (2016.08); *A61K 31/00* (2013.01); *A61K 36/185* (2013.01); *A61K 36/22* (2013.01); *A61K 36/48* (2013.01); *A61K 36/49* (2013.01); *A61K 36/82* (2013.01); *A61K 36/87* (2013.01); *A61K 38/26* (2013.01); *A61K 45/06* (2013.01); *A61P 1/16* (2018.01); *A61P 5/50* (2018.01); *A61P 9/00* (2018.01); *A61P 11/00* (2018.01); *A61P 11/06* (2018.01); *A61P 25/16* (2018.01); *A61P 25/18* (2018.01); *A61P 25/24* (2018.01); *A61P 25/28* (2018.01); *A61P 25/30* (2018.01); *C07H 1/08* (2013.01); *C07H 13/08* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,571,551 A | * | 11/1996 | Fusi | .................... C09B 67/0071 426/250 |
| 2011/0287109 A1 | * | 11/2011 | Bagley | .................. A61K 31/07 424/638 |
| 2018/0133237 A1 | | 5/2018 | Tsai et al. | |

FOREIGN PATENT DOCUMENTS

| | | |
|---|---|---|
| CN | 1398871 A | 2/2003 |
| CN | 1454599 A | 11/2003 |
| CN | 102180917 A | 9/2011 |
| CN | 102245180 A | 11/2011 |
| CN | 102250159 A | 11/2011 |

OTHER PUBLICATIONS

[No Author Listed] Nuts and Seeds in Health and Disease Prevention. Eds: Preedy et al. Apr. 14, 2011. 506.
Jeyaseelan et al., Antibacterial activity of sequentially extracted organic solvent extracts of fruits, flowers and leaves of *Lawsonia inermis* L. from Jaffna. Asian Pac J Trop Biomed. Oct. 2012;2(10):798-802. doi: 10.1016/S2221-1691(12)60232-9.
Qiao et al., Research progress in Galla chinensis and gallic tannins. Sci Tech Food Industry. Jul. 31, 2011. 458-462. Abstract only.
Wu et al., Preparation of gallnut tannins liposome and its quality evaluation. Sci Tech Food Industry. Mar. 31, 2015. 74-77, 81.
PCT/CN2017/078361, dated Jul. 4, 2017, International Search Report and Written Opinion.

* cited by examiner

*Primary Examiner* — Layla D Berry
(74) *Attorney, Agent, or Firm* — Wolf, Greenfield & Sacks, P.C.

(57) ABSTRACT

Compositions (e.g., pharmaceutical compositions, nutraceutical compositions or medical food compositions) comprising tannic acids, particularly tannic acids which are D-amino acid oxidase inhibitor with superior potency, purity and safety profile; and uses thereof for treating CNS disorder and obesity disorders including diabetes, hyperglycemia, hyperlipidemia or hypercholesterolemia.

17 Claims, 26 Drawing Sheets

Experimental design

Animal: 8 week-old male C57BL/6J mice
Groups: 10 males per group
       1. PBS control     2. Tannic acid_15 mg/kg
Drug administration route: intra-peritoneal injection
Acute pain assays: von Frey test
Procedure of hot plate & Von Frey testing:

(A) Enriched method #10

(B) USP Standard (C) Wenzhou Ouhai Fine Chemicals Corporation

COMPOSITIONS CONTAINING TANNIC ACIDS AND USES THEREOF

RELATED APPLICATION

This application is a continuation-in-part application of the International Application No. PCT/CN2017/078361, filed on Mar. 28, 2017, which claims the benefit of U.S. Provisional Application No. 62/313,946, filed Mar. 28, 2016 and U.S. Provisional Application No. 62/458,216, filed Feb. 13, 2017, the entire content of each of which is herein incorporated by reference.

BACKGROUND OF THE INVENTION

Tannins are a group of naturally occurring compounds that exist in various plants, for example, *Rhus chinensis, Rhus javanica, Rhus semialata, Rhus coriaria, Rhus potaninii, Rhus punjabensis* var. *sinica* (Diels) Rehder & E. H. Wilson, *Camellia sinensis, Berry, Bixa orellana, Vitis vinifera, Punica granatum, Quercus infectoria, Quercus cerris, Acacia mearnsii, Pseudotsuga menziesii, Caesalpinia spinosa, Fagus hayata* Palib. ex Hayata, or *Machilus thunbergii* Sieb. & Zucc. etc. There are three major classes of tannins, including hydrolysable tannins (also known as tannic acids), condensed tannins, and phlorotannins, which contain gallic acid, flavone, and phloroglucinol, respectively, as the base unit. Tannins are widely used as a type of industrial particleboard adhesive and for production of anti-corrosive primer or resins. It was also suggested that tannins may have various effects on human health.

D-amino acid oxidase (DAAO) is a peroxisomal enzyme that oxidizes D-amino acids to the corresponding imino acids. It has been reported that DAAO is involved in the metabolism of brain D-amino acids, including D-serine, and the regulation of the glutamatergic neurotransmission. As such, DAAO is a target for treating central nervous system (CNS) disorders that are associated with D-serine and/or glutamatergic neurotransmission.

SUMMARY OF THE INVENTION

The present disclosure is based on the discovery that tannic acids, particularly those having more than three galloyl moieties, effectively inhibited the activity of DAAO. As such, compositions containing such tannic acids would benefit treatment of diseases and disorders associated with DAAO and/or glutamatergic neurotransmission, such as obesity, diabetes, hyperlipidemia and CNS disorders.

Accordingly, one aspect of the present disclosure features a composition (e.g., a pharmaceutical composition, a health food product, or a medical food product), which comprises (i) a mixture of tannic acids or a pharmaceutically acceptable salt thereof, and (ii) a carrier, wherein the composition is substantially free of tannic acids having less than four galloyl moieties. In some examples, the mixture of tannic acids in the composition comprises tannic acids having 4-10 galloyl moieties (e.g., 5-10 galloyl moieties, 5-12 galloyl moieties, or 8-12 galloyl moieties). In some examples, the mixture of tannic acids constitutes at least 95% by weight of the total tannic acid content in the composition. In some examples, the tannic acids described herein are the only tannic acid content in the composition.

In some embodiments, the composition described herein may comprise no more than 20% (e.g., <15%, <10% or <5%) of tannic acids having 1-5 galloyl moieties. Alternatively or in addition, the composition may comprise at least 50% (e.g., >60%, >70%, or >80%) tannic acids having 6-12 galloyl moieties (e.g., 8-12 galloyl moieties).

In some embodiments, the composition described herein comprises (i) a mixture of tannic acids or an acceptable salt thereof, and (ii) a carrier, wherein the composition is substantially free of tannic acids having less than four galloyl moieties. In some examples, ≥98% of the tannic acids in the composition have 4-12 galloyl moieties. In some examples, ≥97% of the tannic acids in the composition have 5-12 galloyl moieties. In some examples, ≥90% of the tannic acids in the composition have 6-12 galloyl moieties. In some examples, ≥60% of the tannic acids in the composition have 8-12 galloyl moieties. In one particular example, the composition comprises about 4-20% of the tannic acids having 5 galloyl moieties, about 10-35% of the tannic acids having 6-7 galloyl moieties, and about 55-85% of the tannic acids having 8-12 galloyl moieties.

In another aspect, the present disclosure provides a composition, comprising (i) a tannic acid or an acceptable salt thereof, and (ii) a carrier, wherein the tannic acid contains 4, 5, 6, 7, 8, 9, 10, 11, or 12 galloyl moieties. The tannic acid may constitute at least 90% (w/w) of the total tannic acid content in the composition. In some examples, the tannic acid constitutes at least 95% by weight of the total tannic acid content in the composition.

In some embodiments, any of the compositions described herein is a pharmaceutical composition, which comprises a pharmaceutically acceptable carrier. Such a pharmaceutical composition may further comprise a second therapeutic agent.

In some examples, the second therapeutic agent is an anti-obesity agent, which includes, but is not limited to, orlistat, lorcaserin, sibutramine, rimonabant, metformin, exenatide, pralintide, phentermine, fenfluramine, dexfenfluramine topiramate, dinitrophenol, bupropion, and zonisamide.

In other examples, the second therapeutic agent is an agent for treating a central nervous system (CNS) disorder. Such an agent can be an antidepressant, an antipsychotic, a phsychostimulant, a mood stabilizer, an anxiolytic, an agent for treating attention deficit hyperactivity disorder (ADHD) or an agent for treating Alzheimer's disease (AD).

Examples of antipsychotic drugs include, but are not limited to, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, memantine, cannabidiol, LY2140023, droperidol, pimozide, butaperazine, carphenazine, remoxipride, piperacetazine, sulpiride, acamprosate, and tetrabenazine.

The antidepressants can be monoamine oxidase inhibitors (MAOIs), tricyclic antidepressants (TCAs), tetracyclic antidepressants (TeCAs), selective serotonin reuptake inhibitors (SSRIs), noradrenergic and specific serotonergic antidepressants (NASSAs), norepinephrine (noradrenaline) reuptake inhibitors, norepinephrine-dopamine reuptake inhibitors, or serotonin-norepinephrine reuptake inhibitors (SNRIs). Examples include, but are not limited to, fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, bupropion, clomipramine, desipramine, doxepin, isocarboxazid, tranylcypromine, trazodone, nefazodone, phenelzine, lamatrogine, lithium, topiramate, gabapentin, carbamazepine, oxacarbazepine, valporate, maprotiline, brofaromine, gepirone, moclobemide, isoniazid, and iproniazid.

Any of the pharmaceutical compositions described herein may be formulated for oral administration or for parenteral administration.

In other embodiments, the composition is a health food product (e.g., a nutraceutical composition) or a medical food product, which may comprise an edible carrier. Such compositions may be formulated as a tablet, a capsule, a soft chew, or a gel.

Also provided herein are methods for preparing the tannic acid composition as described herein. Such a method may comprise (i) providing gallnuts of a plant (e.g., any of the plant or botanic sources as described herein); (ii) grinding the gallnuts to form gallnut power; (iii) extracting the gallnut powder with a first solvent to produce a first tannic acid extract; and (iv) contacting the tannic acid extract with charcoal, $Na_2CO_3$, $K_2CO_3$, $CaSO_4$, $MgSO_4$, or a combination thereof to remove substances absorbed to the charcoal or removed by $Na_2CO_3$, $K_2CO_3$, $CaSO_4$, or $MgSO_4$, thereby producing a first tannic acid composition. Optionally, the method may further comprise (v) dissolving the first tannic acid composition in a second solvent to form a solution, (vi) adding methylene chloride ($CH_2Cl_2$) or dichloroethane to the solution, and (vii) collecting solid substances thus formed, thereby producing a second tannic acid composition. Examples of the first solvent for use in step (iii) include, but are not limited to, acetone, methyl ethyl ketone, ethyl acetate, methyl acetate, ethanol, isopropanol, tetrahydrofuran, 1,4-dioxane, hexane, or a combination thereof. Examples of the second solvent for use in step (v) include, but are not limited to, acetone, acetonitrile, ethyl acetate, methyl ethyl ketone, ethanol, isopropanol, tetrahydrofuran, 1,4-dioxane, or a combination thereof.

In some embodiments, any of the preparation methods as described herein may further comprise a step of removing tannic acids having 2-5 galloyl moieties to form an enriched tannic acid extract. The removing step can be performed by mixing a first tannic acid extract with a solvent, which can be a combination of (i) any one of acetone, acetonitrile, methyl ethyl ketone, ethyl acetate, or methyl acetate, and (ii) any one of pentane, hexane, or heptane, to form two organic layers and collect the oily layer to produce the enriched tannic acid extract. In some instances, the solvent comprises methyl ethyl ketone/hexane, or ethyl acetate/hexane. In some examples, the removing step can be performed after step (iii) and before step (iv).

In some embodiments, any of the preparation methods as described herein may further comprise, prior to step (iii) and after step (ii), passing the gallnut power through a sieve of 20-60-mesh.

In certain embodiments, a method for preparing a tannic acid composition as described herein may comprise: (i) providing a composition containing tannic acids; (ii) extracting (e.g., at 20-80° C.) the composition with a first solvent (e.g., acetone, acetonitrile, methyl ethyl ketone, ethyl acetate, methyl acetate, ethanol, isopropanol, tetrahydrofuran, 1,4-dioxane, heptane, hexane, water, or a combination thereof) to produce a first tannic acid extract; and (iii) contacting the first tannic acid extract with one or more of charcoal, metal carbonate, and metal sulfate (e.g., at 20-80° C.) to remove substances absorbed to the charcoal and/or metal carbonate, or precipitated by the metal sulfate, thereby producing a first tannic acid composition. Optionally, the method may further comprise contacting the mixture formed in step (iii) with silicon dioxide.

In some examples, step (ii) may be performed at 20-60° C. Alternatively or in addition, step (ii) above may be performed by incubating multiple batches of the composition with the first solvent sequentially. For example, step (ii) can be performed by (a) incubating a first batch of the composition with the first solvent, (b) incubating a second batch of the composition with the mixture formed in (a), and (c) incubating a third batch of the composition with the mixture formed in (b) to produce the first tannic acid extract.

In some examples, step (iii) can be performed by (a) contacting the first tannic acid extract with a metal carbonate (e.g., at 20-60° C.) to form a mixture, (b) extracting the mixture with ethyl acetate, methyl acetate, methyl ethyl ketone, or a combination thereof (e.g., at 20-50° C.) to produce an organic solution, and (c) incubating the organic solution with the charcoal and metal sulfate (e.g., at 20-60° C.), simultaneously or sequentially. When desired, the mixture formed in step (c) may be incubated with silicon dioxide for a suitable period. Exemplary metal carbonates include, but are not limited to, lithium carbonate, sodium carbonate, or potassium carbonate. Exemplary metal sulfate can be calcium sulfate or magnesium sulfate.

Any of the preparation methods described herein may further comprise: (iv) mixing the first tannic acid composition with a second solvent (e.g., acetone, acetonitrile, ethyl acetate, methyl acetate, methyl ethyl ketone, or a combination thereof) to form a solution; (v) contacting the solution with dichloromethane, dichloroethane, pentane, hexane, heptane, or a mixture thereof (e.g., at 20-40° C.) to allow for precipitation of tannic acids in solid form; and (vi) collecting the tannic acids in solid form, thereby producing a second tannic acid composition.

In some instances, the method may further comprise, (e.g., prior to step (iv)), removing dextrin, gum, and/or resin from the first or second tannic acid composition. This removing step may be performed by a process comprising (a) mixing the first or second tannic acid composition with a polar solvent (e.g., ethyl acetate, methyl acetate, acetone, methyl ethyl acetone, acetonitrile, and collecting the organic layer thus formed; and optionally (b) contacting the organic layer with an alkyl solvent (e.g., pentane, hexane, or heptane), a chlorinated solvent (e.g., dichloromethane or dichloroethane), or a mixture thereof at 10-70° C., and (c) collecting the bottom oily layer thus formed.

Alternative or in addition, the method may further comprise a step of removing solvent residues. This step may comprise (a) mixing the second tannic acid composition with an alkyl solvent (e.g., pentane, hexane, or heptane), a chlorinated solvent (e.g., dichloromethane, or dichloroethane), or a combination thereof, and (b) stirring the mixture formed in (a) (e.g., at 10-70° C. such as 50-70° C.) to remove solvent residues.

In any of the preparation methods described herein, the composition containing tannic acids of step (i) may be gallnut powder or gallnut chips obtained from gallnuts of a plant. Suitable plants for use in the methods described herein include, but are not limited to, *Rhus chinensis, Rhus javanica, Rhus semialata, Rhus coriaria, Rhus potaninii, Rhus punjabensis* var. *sinica* (Diels) Rehder & E. H. Wilson, *Camellia sinensis, Berry, Bixa orellana, Vitis vinifera, Punica granatum, Quercus infectoria, Quercus cerris, Acacia mearnsii, Pseudotsuga menziesii, Caesalpinia spinosa, Fagus hayata* Palib. ex Hayata, and *Machilus thunbergii* Sieb. & Zucc. In some examples, the plant is one of *Rhus chinensis, Rhus javanica, Rhus semialata, Rhus coriaria, Rhus potaninii*, and *Rhus punjabensis* var. *sinica* (Diels) Rehder & E. H. Wilson.

The gallnuts for use in preparing tannic acid compositions described herein may have diameters ranging from 1-8 cm. In some examples, the gallnuts can be Chinese belly-shaped gallnuts or horned gallnuts. In one example, the gallnuts are Chinese horned gallnuts having diameters ranging from 1-8 cm, e.g., from 2-6 cm or from 3-5 cm.

A tannic acid composition prepared by any of the preparation methods described herein is also within the scope of the present disclosure. Such a tannic acid composition may contain ≤2% of the tannic acids in the second tannic acid composition have 1-4 galloyl moieties.

In yet another aspect, the present disclosure features a method for treating a disease or disorder associated with DAAO, the method comprising administering to a subject in need thereof an effective amount of a composition (e.g., a pharmaceutical composition, a health food product, or a medical food product), which comprises (i) one or more tannic acids or a pharmaceutically acceptable salt thereof and (ii) a pharmaceutically acceptable carrier; wherein the pharmaceutical composition is substantially free of condensed tannins and/or phlorotannins. In some embodiments, the target disease to be treated by the method disclosed herein is a CNS disorder, which may be pain, psychosis, anxiety, depression, suicidal ideation and/or behavior, autism, OCD, mania, Tourette's syndrome, dementia, and behavior and psychological symptoms of dementia (BPSD).

In some embodiments, the composition for use in the treatment method described herein can be any of the pharmaceutical compositions, health food products, and/or medical food products described herein. Such a composition may be used for treating a disorder associated with obesity. In some examples, the subject in need of the treatment is a human patient having or suspected of having the disorder associated with obesity. In other examples, the subject is a human patient who has been subjected to or is on a treatment of an obesity disorder. Exemplary disorders associated with obesity include, but are not limited to, eating disorders, anorexia nervosa, bulimia nervosa, stroke, coronary heart disease, heart attack, congestive heart failure, congenital heart disease, hypertension, diabetes mellitus, hyperlipidemia, hypercholesterolemia, non-alcoholic steatohepatitis, insulin resistance, hyperuricemia, hypothyroidism, osteoarthritis, gallstones, infertility (e.g., hypogonadism and hyperandrogegism), obesity hypoventilation syndrome, obstructive sleep apnea, chronic obstructed pulmonary disease, and asthma.

In some embodiments, the composition described herein is for use in treating a central nervous system (CNS) disorder. Exemplary CNS disorders include, but are not limited to, ADHD, schizophrenia, pain, depression, suicidal ideation and/or behavior, bipolar disorder, tic disorder, post-traumatic stress disorder, anxiety, social anxiety disorder, panic disorder, autism, Asperger's disorder, obsessive-compulsive disorder (OCD), learning disorder, Tourette's syndrome, mild cognitive impairment, dementia, vascular dementia, multi-infarct dementia, Alzheimer's disorder, frontotemporal dementia, dementia with Lewy bodies, Parkinson's disorder, Huntington's disease, amyotrophic lateral sclerosis, nocturnal enuresis, blepharospasm, and non-epileptic seizure. In some examples, the subject in need of the treatment is a human patient having or suspected of having the CNS disorder. In other examples, the subject is a human patient who has been subjected to or is on a treatment for treating the CNS disorder.

Also within the scope of the present disclosure are (i) any of the tannic acid-containing compositions (e.g., pharmaceutical compositions, health food products, or medical food products) described herein for use in treating an DAAO- and/or glutamatergic neurotransmission-associated disease/disorder, such as those described herein, or for treating an obesity disorder, eating disorder, anorexia nervosa, bulimia nervosa, hyperlipidemia, hyperglycemia, diabetes, or an CNS disorder, and (ii) uses of such composition in manufacturing medicaments for use in treating any of the target diseases/disorders, including those described herein.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION

Figure 1:
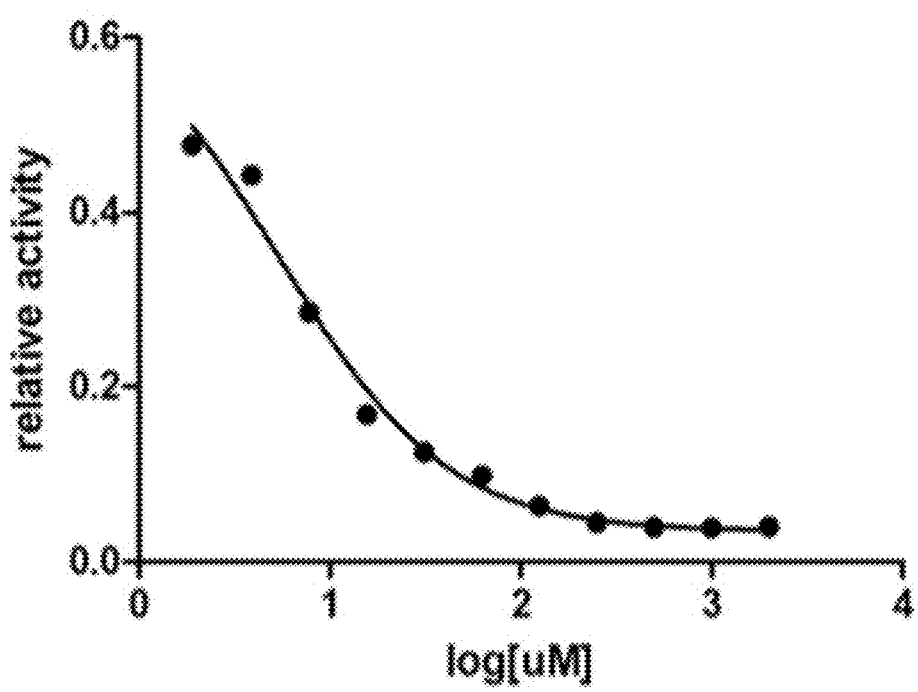
FIG. 1 is a chart showing that tannic acids as a group inhibit D-amino acid oxidase (DAAO).

Tannic acids are a subfamily of tannins existing in various plants. Tannic acids extracted from plants are a mixture of polygalloyl glucoses or polygalloyl quinic acid esters containing 2-12 galloyl moieties. Provided below is the structure of an exemplary tannic acid molecule that contains 10 galloyl moieties linked to a glucose moiety.

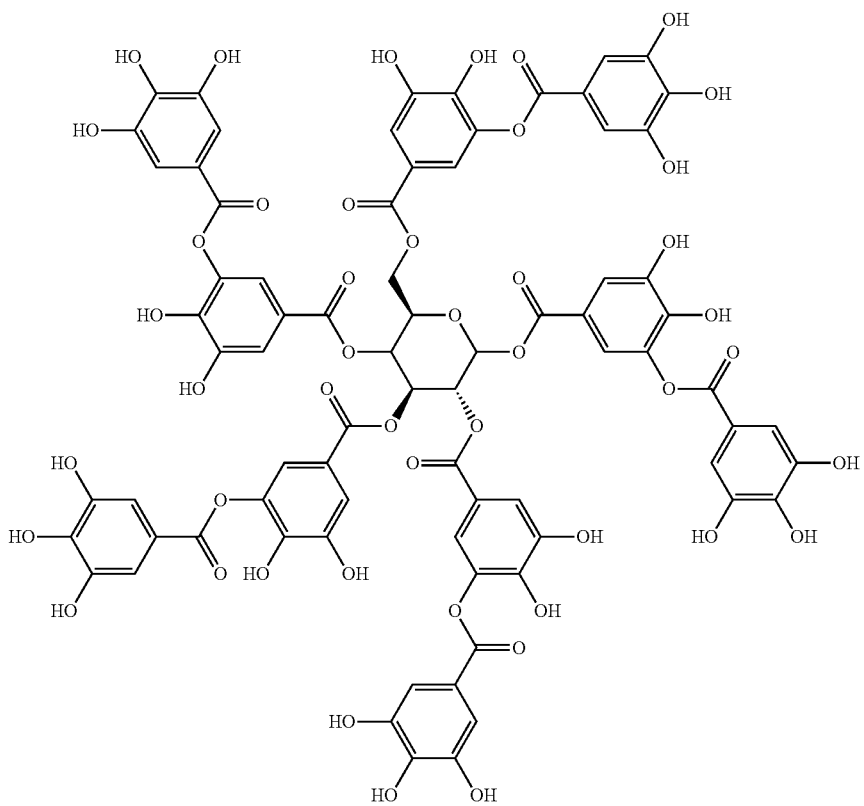 [SMILES: O=C(OC[C@H]1OC(OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H](OC(=O)c2cc(O)c(O)c(OC(=O)c3cc(O)c(O)c(O)c3)c2)C1OC(=O)c1cc(O)c(O)c(OC(=O)c2cc(O)c(O)c(O)c2)c1)c1cc(O)c(O)c(OC(=O)c2cc(O)c(O)c(O)c2)c1]

Historically, tannic acids have been used as an antidote to soak up poisons, and for treating short-term conditions, such as bleeding, rashes and other conditions of soreness.

The present disclosure is based on the discoveries that tannic acids, particularly those having four or more galloyl moieties, showed strong inhibitory activity against DAAO, which is known to be involved in various diseases and disorders, such as an obesity disorder, hyperlipidemia, hypercholesterolemia, hyperglycemia, diabetes, and CNS disorders. The present studies also showed that tannic acids successfully reduced body weight and improved basic behavioral functioning, hyperactivity, anxiety, depression, sensorimotor gating, pain threshold, memory and cognitive behaviors in a mouse model. Further, tannic acids showed rescue and protective effects on mice treated with MK-801, an antagonist of the N-methyl-D-aspartate receptor (the NMDA receptor). NMDA receptor is a glutamate receptor and ion channel protein expressed on nerve cells and plays an important role in controlling synaptic plasticity, repair, neurodevelopment, learning and memory function. Most CNS disorders have dysfunction of NMDA receptor.

Accordingly, the present disclosure provides tannic acid-containing compositions, kits and methods of using such for improving basic functioning, body weight, hyperactivity, anxiety, depression, suicidal ideation and/or behavior, sensorimotor gating, pain threshold, memory and cognitive behaviors in a subject in need of the treatment, and/or for treating diseases and disorders associated with DAAO, such as obesity disorders, hyperlipidemia, hypercholesterolemia, hyperglycemia, diabetes, and CNS disorders.

I. Tannic Acid-Containing Compositions and Kits Containing Such

One aspect of the present disclosure relates to compositions, for example, pharmaceutical compositions, health food product such as nutraceutical compositions, and medical food that comprise one or more tannic acids and a carrier, e.g., a pharmaceutically acceptable carrier and/or an edible carrier. Such carriers, either naturally occurring or non-naturally occurring (synthetic), may confer various benefits to the tannic acids in the composition, for example, improving in vitro and/or in vivo stability of the tannic acids, enhancing bioavailability of the tannic acids, increasing bioactivity of the tannic acids, and/or reducing side effects. Suitable carriers include, but are not limited to, diluents, fillers, salts, buffers, stabilizers, solubilizers, buffering agents, preservatives, or a combination thereof. In some examples, the carrier may comprise benzoate such as sodium benzoate.

(A) Tannic Acid Content

The compositions described herein comprise one or more tannic acids or pharmaceutically acceptable salts thereof. The term "pharmaceutically-acceptable salts" refers to the relatively non-toxic, inorganic or organic base addition salts of tannic acids. These salts can be prepared in situ in the administration vehicle or the dosage form manufacturing process, or by separately reacting the one or more tannic acids with a suitable organic or inorganic base, and isolating the salt thus formed during subsequent purification. Suitable inorganic bases include, but are not limited to, sodium hydroxide, barium hydroxide, iron (ii) hydroxide, iron(III) hydroxide, magnesium hydroxide, calcium hydroxide, aluminium hydroxide, ammonium hydroxide, potassium hydroxide, caesium hydroxide, or lithium hydroxide. Suitable organic bases include, but are not limited to, pyridine, methyl amine, imidazole, benzimidazole, histidine, phosphazene bases, or a hydroxide of an organic cation such as quaternary ammonium hydroxide and phosphonium hydroxide. See, for example, Berge et al. (1977) J. Pharm. Sci. 66:1-19.

In some embodiments, the tannic acids contained in the compositions disclosed herein are a mixture of tannic acids having various numbers of galloyl moieties, e.g., 2-12, 4-12, 4-10, 5-10, 5-12, 6-12, or 8-12, or pharmaceutically acceptable salts thereof. In some examples, the mixture of tannic acids contains tannic acids having at least 4 galloyl moieties (e.g., 4-12, 4-10, 4-9, or 4-7 galloyl moieties) or pharmaceutically acceptable salts thereof. Optionally, the tannic acids in the composition may be substantially free of tannic acids having 3 or less galloyl moieties which have relatively low activity to inhibit D-amino acid oxidase. As used herein, "substantially free" of tannic acids having 3 or less galloyl moieties means that the total amount of such tannic acids in the composition is no more than 10% by weight. In some examples, the total amount of tannic acids having 3 or less galloyl moieties in the compositions described herein may be less than 8%, 5%, 2%, 1%, or less. In some examples, the composition is completely free of any tannic acid having 3 or less galloyl moieties.

Any of the compositions described herein may contain no more than 20% (e.g., no more than 18%, 15%, 12%, 10%, 5%, or less) tannic acids with 1-5 galloyl moieties. Alternatively or in addition, the composition may contain no less than 50% (e.g., 60%, 70%, 75%, 80%, 85%, 90%, or more) of tannic acids with 6-12 galloyl moieties or with 8-12 galloyl moieties. In one particular example, the composition contains no more than 18% of tannic acid having 1-5 galloyl moieties and no less than 60% tannic acids having 6-12 galloyl moieties. In another example, the composition contains no more than 15% of tannic acids with 1-5 galloyl moieties and no less than 70% of tannic acids with 6-12 galloyl moieties. In yet another example, the composition contains no more than 12% of tannic acids with 1-5 galloyl moieties and no less than 80% of tannic acids with 6-12 galloyl moieties. Alternatively, the composition contains no more than 10% of tannic acids having with 1-5 galloyl moieties and no less than 90% of tannic acids with 6-12 galloyl moieties.

In some embodiments, the composition described herein may contain ≥98% (e.g., 98.5%, 99%, or 99.5%) of tannic acids that have 4-12 galloyl moieties. In other embodiments, the composition may contain ≥97% (e.g., 97.5%, 98%, 98.5%, 99%, or 99.5%) of tannic acids that have 5-12 galloyl moieties. In yet other embodiments, the composition may contain ≥90% (e.g., 92%, 95%, 97%, 98%, or higher) of tannic acids that have 6-12 galloyl moieties. Alternatively, the composition described herein may contain ≥60% (e.g., 70%, 75%, 80%, 85%, 90%, 95%, or higher) of tannic acids that have 8-12 galloyl moieties.

In particular examples, the composition described herein may contain about 4-20% (e.g., about 10-20% such as about 15%) of tannic acids having 5 galloyl moieties, about 10-35% (e.g., about 15-25% such as about 20%) of tannic acids having 6-7 galloyl moieties, and about 55-85% (e.g., about 55-65% such as about 60% or 65%) of tannic acids having 8-12 galloyl moieties.

In other embodiments, the tannic acids contained in the compositions described herein are a substantially homogeneous population. Such a tannic acid population may contain a tannic acid having a defined number of galloyl moieties, for example, any number between 3 and 12 (including 3 and 12), or a pharmaceutically acceptable salt thereof. As used herein, the term "substantially homogenous" means that the tannic acid having the defined number of galloyl moieties constitutes at least 85% by weight (e.g., 90%, 95%, 97%, 98%, 99%, or above) of the total tannic acid content in the composition. In some examples, the substantially homogenous tannic acid population contains tannic acids having 4, 5, 6, 7, 8, 9, 10, 11 or 12 galloyl moieties. Such substantially homogeneous tannic acid populations may be isolated from a mixture of tannic acids having varied numbers of gallolyl moieties (e.g., those described herein) via a conventional method, for example, chromatography.

The tannic acid or tannic acid mixture for use in making the compositions disclosed herein may be prepared by conventional methods. For example, a mixture of tannic acids may be extracted or isolated from at least a suitable plant source, including. but not limited to *Rhus chinensis, Rhus javanica, Rhus semialata, Rhus coriaria, Rhus potaninii, Rhus punjabensis* var. *sinica* (Diels) Rehder & E. H. Wilson, *Camellia sinensis*, Berry, *Bixa orellana, Vitis vinifera, Punica granatum, Quercus infectoria, Quercus cerris, Acacia mearnsii, Pseudotsuga menziesii, Caesalpinia spinosa, Fagus* hayata Palib. ex Hayata, or *Machilus thunbergii* Sieb. & Zucc. In some embodiments, the tannic acid or tannic acid mixture contained in the composition herein are extracted from *Rhus chinensis, Rhus javanica, Rhus semialata, Rhus coriaria, Rhus potaninii*, or *Rhus punjabensis* var. *sinica* (Diels) Rehder & E. H. Wilson.

The plant source described herein may require a nesting insect including but not limited to *Andricus kollari, Andricus fecundatrix, Andricus quercuscalicis, Andricus quercuscalicis, Biorhiza pallida, Neuroterus quercusbaccarum, Neuroterus albipes, Neuroterus numismalis, Cynips quercusfolii, Melaphis chinensis* (Bell), *Melaphis peitan* Tsai et Tang, *Nurudea sinica* Tsai et Tang, *Nurudea shiraii* Matsumura, *Nurudea rosea* Matsumura, *Meitanaphis elongallis* Tsai et Tang, *Macrorhinarium ensigallis* Tsai et Tang, *Macrorhinarium ovagallis* Tsai et Tang, *Floraphis meitanensis* Tsai et Tang, *Meitanaphis flavogallis* Tang, *Kaburagia rhusicola* Takagi, *Kaburagia ovatihuicola* Xiang, *Kaburagia ensigallis* Tsai et Tang, *Kaburagia ovogallis, Kaburagia thusicola* Takagi, *Meitanaphis microgallis* Xiang, and *Floraphis choui* Xiang.

In some embodiments, the tannic acid or tannic acid mixture is extracted from gallnuts, including, but not limited to, Chinese belly-shaped gallnuts, horned gallnuts, hard ensiform gallnuts, egg-hard ensiform gallnuts, and inflorescence gallnuts of at least a plant or botanic source and requiring nesting insect described herein. The gallnut for use in preparing the tannic acids may have a diameter ranging from 1-8 cm (e.g., 1 cm, 2 cm, 3 cm, 4 cm, 5 cm, 6 cm, 7 cm, or 8 cm). In some examples, the gallnut may have a diameter ranging from 2-6 cm (e.g., 3-5 cm).

| Plant | Nesting insect | Gallnuts |
|---|---|---|
| Quercus infectoria | Andricus kollari | Oak gallnuts[1] |
| Rhus chinensis | Melaphis chinensis (Bell) | Chinese horned gallnuts[2] |
| Rhus potaninii | Melaphis peitan Tsai et Tang | Chinese belly-shaped gallnuts[2] |

[1]The population biology of oak gall wasps (Hymenoptera: Cynipidae), Annual Review of Entomology. 2002; 47: 633-68
[2]Study on Chinese Gallnut, Forest Research, 2003, 16(6): 760-767

While the tannic acid population, either heterogeneous or substantially homogeneous, can be purified from a suitable natural source, the tannic acid-containing composition described differs from the naturally-occurring tannic acid compositions in various aspects. In some examples, the tannic acid mixture in the composition is substantially free of tannic acids having less than 4 galloyl moieties, which exist in naturally-occurring tannic acid mixtures. Removal of the tannic acids having a low number of galloyl moieties can enhance the biological activity (e.g., inhibiting DAAO) of the resultant tannic acid mixture. In other examples, the composition described herein contain tannic acids having a high number of gallolyl moieties (e.g., 5-12, 6-12, 7-12, or 8-12) at a level substantially greater than such tannic acids in naturally-occurring tannic acid mixtures. As provided herein, the tannic acid populations contained in the composition described herein showed enhanced biological activity (e.g., inhibiting DAAO) as compared with tannic acids having lower numbers of gallolyl moieties. In yet other examples, the composition may contain a substantially homogeneous population of tannic acids, as opposed to the heterogeneous population of tannic acids existing in nature.

The tannic acid extract may be subjected to one or more purification procedures, for example, gel filtration, fractionation, partition, re-crystallization, and chromatography (e.g., HPLC) or a combination thereof. See, e.g., Examples below. Alternatively, the tannic acid or tannic acid mixture may be prepared by chemical synthesis following routine methodology. In some embodiments, a tannic acid composition as described herein can be prepared as follows. Gallnuts from a suitable plant or botanic source, e.g., those described herein, can be obtained via routine methods. The gallnuts can be grinded to form gallnut powers or gallnut chips. In some examples, the gallnut power can be passed through a sieve having a suitable size (e.g., 20-mesh, 30-mesh, 40-mesh, 50-mesh, or 60-mesh) to form fine gallnut powers.

A suitable solvent can then be used to extract the tannic acid content from any of the gallnut powers described herein. As used herein, the term "solvent" refers to a liquid capable of dissolving one or more solutes. A solvent may comprise a pure population of a substance that dissolves a solute of interest. Alternatively, a solvent as used herein may be a mixture of multiple substances for dissolving the solute. A suitable solvent for extracting tannic acids comprise acetone, acetonitrile, methyl ethyl ketone, ethyl acetate, methyl acetate, ethanol, isopropanol, tetrahydrofuran, 1,4-dioxane, pentane, hexane, heptane, water, or a combination thereof. To extract the tannic acid contents, the gallnut powers can be placed into a suitable volume of the solvent. The mixture thus formed can be stirred at a suitable temperature (e.g., room temperature) for a suitable period (e.g., 6-18 hours, 6-12 hours, 12-18 hours, or 18-24 hours). The resultant solution can then be filtered and concentrated by routine practice (e.g., by vacuum evaporation).

In some embodiment, tannic acids can be extracted from a composition comprising tannic acids, for example, the gallnut power or chips described herein, using a suitable solvent as also described herein. Such a tannic acid-containing composition may comprise a heterogeneous population of tannic acids. In some examples, multiple batches of the tannic acid-containing compositions may be placed into the suitable solvent sequentially, each being incubated (e.g., with stirring) in the suitable solvent for a suitable period, e.g., 1-6 hours. For example, a first batch of the tannic acid-containing composition may be incubated with the suitable solvent for a suitable period, e.g., 1-6 hours or 2-4 hours. A second batch of the tannic acid-containing composition (which may be in substantially the same amount as the first batch) may then be placed into the suitable solvent (containing the first batch) and incubated for a suitable period, e.g., 1-6 or 2-4 hours. Afterwards, a third batch of the tannic acid-containing composition (which may also be in substantially the same amount as the first batch and/or second batch) may be placed in the same suitable solvent (containing the first and second batches) and incubate for a suitable period, e.g., 1-10 hours, 2-8 hours, or 3-6 hours. If needed, additional batches of the tannic acid-containing composition may be incubated with the suitable solvent in a similar manner. The soluble portion of the mixture then formed can then be filtered to remove insoluble substances and concentrated in vacuum to produce a crude tannic acid extract. Surprisingly, the yield of tannic acids using the multiple-batch approach was found to be at least 2 fold higher than the yield of tannic acids using a single-batch approach (incubating the same total amount of the tannic acid-containing composition in the same amount of the solvent simultaneously). See Enrichment method 11 below.

The crude tannic acid extract can then be dissolved in a suitable solvent such as water, an organic solvent or a combination thereof to form a tannic acid solution, which can be mixed with one or more of charcoal, metal carbonate (e.g., $Na_2CO_3$, $K_2CO_3$) and metal sulfate (e.g., $CaSO_4$, $MgSO_4$), simultaneously or sequentially to remove undesired substances (e.g., substances that can be absorbed to the charcoal or precipitated by the metal carbonate and/or metal sulfate). In some examples, any of the tannic acid-containing compositions obtained from preceding steps can be mixed with charcoal first for a suitable period of time (e.g., stirred at room temperature for 1-24 hours). the metal carbonate and/or metal sulfate can then be added to the mixture, which can be stirred under a suitable temperature (e.g., room temperature) for a suitable period (e.g., 30 minutes to 6 hours). The mixture can then be filtered through, e.g., a bed of Celite, washed with a suitable solvent (e.g., acetone, acetonitrile, methyl ethyl ketone, ethyl acetate, ethanol, or a combination thereof), and concentrated by a routine method to produce a tannic acid composition.

In other examples, the tannic acid solution as described herein can be mixed with charcoal first for a suitable period of time (e.g., stirred at room temperature for 1-24 hours, for example, 6-12 hours or 12-18 hours). The charcoal can then be removed from the mixture to form a solution. $Na_2CO_3$, $K_2CO_3$, $CaSO_4$ and/or $MgSO_4$ can then added to the solution, which can be stirred under a suitable temperature (e.g., room temperature) for a suitable period (e.g., 30 minutes to 6 hours, for example, 30 minutes to 2 hours or to 1 hour). The mixture can then be filtered through, e.g., a bed of Celite, washed with a suitable solvent (e.g., acetone, acetonitrile, methyl ethyl ketone, ethyl acetate, methyl acetate, ethanol, or a combination thereof), and concentrated by a routine method to produce a tannic acid composition.

In other examples, the crude tannic acid extract can be mixed with charcoal first for a suitable period of time (e.g., stirred at room temperature for 1-24 hours, for example, 6-12 hours or 12-18 hours). The charcoal can then be removed from the mixture to form a solution. A metal carbonate and/or metal sulfate (e.g., $Na_2CO_3$, $K_2CO_3$, $CaSO_4$ and/or $MgSO_4$) can then added to the solution, which can be stirred under a suitable temperature (e.g., room temperature) for a suitable period (e.g., 30 minutes to 6 hours, for example, 30 minutes to 2 hours or to 1 hour). The mixture can then be filtered through, e.g., a bed of Celite, washed with a suitable solvent (e.g., acetone, acetonitrile, methyl ethyl ketone, ethyl acetate, methyl acetate, ethanol, or a combination thereof), and concentrated by a routine method to produce a tannic acid composition.

In some examples, a mixture formed in any of the steps described above may be placed in a suitable amount of ethyl acetate (e.g., 3-8×mL or 6×mL) and incubated at a suitable temperature (e.g., room temperature) for a suitable period (e.g., 1-2 hours). The organic layer thus formed can be collected, which contains tannic acids.

When needed, a method for preparing the tannic acid composition as described herein may further comprise a step of reducing or removing tannic acids having 2-5 galloyl moieties (2-5 G), a step of enriching tannic acids having 6-12 galloyl moieties (6-12 G), or both.

To remove tannic acids having 2-5 G, a crude tannic acid composition can be mixed with a suitable solvent to form a mixture, which can be incubated (e.g., stirred) for a suitable period (e.g., 6-18 hours) under a suitable temperature (e.g., room temperature) to allow for formation of two organic layers. Tannic acids having less than 5 G would be dissolved in the upper layer. Tannic acids having greater than 5 G would stay in the oiler layer (lower layer) as solid substances. The oiler layer, enriched with tannic acids having large numbers of galloyl moieties, can be collected. If needed, the oiler layer can be concentrated and the solids thus obtained can be dissolved in a suitable solvent. Suitable solvents for removing tannic acids having less than 5 G include, but are not limited to, a mixture of any one of the group (i) solvent and any one of the group (ii) solvent listed below:

(i) acetone, acetonitrile, methyl ethyl ketone, or ethyl acetate; and (ii) pentane, hexane, or heptane.

The resultant solution may be subject to the charcoal, $Na_2CO_3$, $K_2CO_3$, $CaSO_4$ and/or $MgSO_4$ treatment to remove undesired substances as described herein.

To enrich tannic acids having large numbers of galloyl moieties (e.g., 6-12 G), a tannic acid-containing composition can be first dissolved in a suitable solvent such as acetone, acetonitrile, methyl ethyl ketone, ethyl acetate, or methyl acetate. The solution thus formed can be stirred and $CH_2Cl_2$ or dichloroethane can be added to the solution slowly dropwise to allow for precipitation of the desired tannic acids. The solids can then be collected by routine practice (e.g., filtration and/or drying) to produce an enriched tannic acid composition.

In some embodiments, any of the preparation methods described herein may comprise a resin removal step. This step may be performed by mixing a tannic acid-containing composition with a suitable amount of an alkyl solvent and stirring the mixture thus formed at a suitable temperature (e.g., room temperature) for a suitable period (e.g., 1-4 hours or 2-3 hours). The tannic acid-containing composition may be diluted in a suitable solvent (in which tannic acids can be dissolved, for example, acetone) if needed. Alkyl solvent refers to a solvent having an alkyl chain, for example, a $C_1$-$C_{10}$ alkyl chain. Examples include, but are not limited to, hexane, pentane or heptane. After the stirring process, the mixture can be kept for a while to allow for separation of two layers. The organic layer thus formed can be collected. If needed, the resin-removal step can be repeated multiple times (e.g., 2-4 times).

Prior to the treatment with the alkyl solvent, the tannic acid-containing composition may be first mixed with a polar solvent for a suitable period to allow formation of an organic layer, which can be collected and subject to the following treatment with the alkyl solvent as described herein. A polar solvent contains molecules that are partially charges (have large dipole moments) and typically contain bonds between atoms with very different electronegativities, such as between oxygen and hydrogen. In some instances, the polar solvent can be a protic solvent, which contains molecules having a hydrogen atom bound to an oxygen or nitrogen. Examples include formic acid, n-butanol, isopropanol (IPA), nitromethane, ethanol (EtOH), methanol (MeOH), acetic acid, and water. In other instances, the polar solvent can be an aprotic solvent, which lacks an acidic hydrogen. Examples include N-methylpyrrolidone, tetrahydrofuran (THF), ethyl acetate (EtOAc), acetone, dimethylformamide (DMF), acetonitrile (MeCN), dimethyl sulfoxide (DMSO), and propylene carbonate (PC).

Results from this study showed that performing the resin removal step noted above twice led to significantly enhanced resin removal efficiency as compared with using $MgSO_4$, $Na_2CO_3$, and/or $K_3CO_3$ treatment.

In some embodiments, any of the preparation methods described herein may further comprise a step of removing solvent residues from tannic acid solids obtained following the procedures described herein. To perform this removal step, tannic acid solids may be slurried using a suitable amount (e.g., 5-30×mL such as 20×mL) of a suitable solvent at a suitable temperature (e.g., 40-70° C. such as 60° C.) for a suitable period (e.g., 12-24 hours, such as 16 hours). The resultant mixture can then be filtered and evaporated in vacuum at a suitable temperature (e.g., 10-80° C., preferably 60-80° C. such as 70° C.) to allow for removal of residues of solvents used in the preparation process. The solvent for use in this step may be an alkyl solvent (e.g., $C_1$-$C_{10}$ alkyl solvent such as hexane), a chlorinated solvent such as dichloromethane, or dichloroethane, or a combination thereof. When needed, this step can be repeated multiple times (e.g., 2-5 times) such that solvent residues can be removed substantially from the final tannic acid products. As shown in the table below, performing this step could significantly remove solvent residues from the final tannic acid products.

TABLE 1

Efficiency of Solvent Residue Removal

| Slurry | Conditions | % of Solvent residue |
| --- | --- | --- |
| No Slurry | — | Dichloromethane: 2.0% |
| | | Acetone: 5.0% |
| 1$^{st}$ Slurry | 1. Heptane, 60° C., 16 hr | Dichloromethane: 1.0% |
| | 2. Dry, 70° C., 8 hr | Acetone: 1.2% |
| | | Heptane: <0.2% |
| 2$^{nd}$ Slurry | 1. Heptane, 60° C., 16 hr | Dichloromethane: 0.1% |
| | 2. Dry, 70° C., 8 hr | Acetone: 0.7% |
| | | Heptane: <0.2% |
| 3$^{rd}$ Slurry | 1. Heptane, 60° C., 16 hr | Dichloromethane: 0% |
| | 2. Dry, 70° C., 8 hr | Acetone: 0.4% |
| | | Heptane: <0.2% |

Some examples follow, which are merely illustrative and by no means limit the present disclosures to these specific examples.

A method comprising: (i) grinding gallnuts of a suitable plant or botanic source to form crude gallnut powder; (ii) passing the crude gallnut powder though a 40-mesh sieve to form fine gallnut powders; (iii) dissolving the fine gallnut powders in a suitable solvent (e.g., acetone, acetonitrile, methyl ethyl ketone (MEK), ethyl acetate (EtOAc), methyl acetate (MeOAc), ethanol (EtOH), isopropanol (IPA), tetrahydrofuran (THF), 1,4-dioxane, or a combination thereof) and stirring the mixture thus formed at 20 to 60° C. for 3-24 hr; (iv) filtering and concentrating the resultant solution to form solid residues; (v) mixing the solid residues with a solvent (e.g., 20%-60% methyl ethyl ketone/hexane or 30-50% methyl ethyl ketone/hexane) at 20 to 60° C. for 3-24 hrs to form two organic layers; (vi) harvesting and concentrating the oilier layer from (v); (vii) dissolving the residues thus formed in a suitable solvent (e.g., acetone, acetonitrile, methyl ethyl ketone, ethyl acetate, ethanol, or a combination thereof) to form a solution; (viii) stirring the solution from (vii) in the presence of charcoal for 1-24 hrs; (ix) stirring the mixture from (viii) in the presence of $Na_2CO_3$, $K_2CO_3$, $CaSO_4$ or $MgSO_4$; (x) removing charcoal, $Na_2CO_3$, $K_2CO_3$, $CaSO_4$ or $MgSO_4$ from the mixture from (ix) via a routine practice; (xi) concentrating the filtrate from (x); (xii) dissolving the residue from (xi) in a suitable solvent (e.g., acetone, acetonitrile, methyl ethyl ketone, ethyl acetate, methyl acetate, or a combination thereof); (xiii) adding methylene chloride or dichloroethane into the solution from (xii); and (xiv) collecting and drying the solid formed in (xiii).

A method comprising: (i) grinding gallnuts of a suitable plant to form crude gallnut powder; (ii) passing the crude gallnut powder from (i) though 40-mesh sieve to form fine gallnut power; (iii) dissolving the fine gallnut powder in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring the resultant solution at 20 to 60° C. for 3-24 hrs; (iv) filtering the solution, (v) adding a suitable solvent (e.g., pentane, hexane, heptane, or a combination thereof) to the solution from (iv) and stirring it for 3-24 hrs to form two organic layers; (vi) harvesting and concentrating the oilier layer from (v); (vii) dissolving the residue from (vi) in a suitable solvent (e.g., acetone, acetonitrile, methyl ethyl ketone, ethyl acetate, methyl acetate, ethanol, or a combination thereof); (viii) stirring the solution from (vii) in the presence of charcoal for 1-24 hrs (e.g., 6-12 hrs or 12-18 hrs); (ix) stirring the mixture from (viii) in the presence of $Na_2CO_3$, $K_2CO_3$, $CaSO_4$ or $MgSO_4$; (x) removing charcoal, $Na_2CO_3$, $K_2CO_3$, $CaSO_4$ or $MgSO_4$ from the mixture from (ix) via routine practice; (xi) concentrating the filtrate from (x); (xii) dissolving the residue from (xi) in a suitable solvent (e.g., acetone, acetonitrile, methyl ethyl ketone, ethyl acetate, methyl acetate, ethanol, or a combination thereof), (xiii) adding methylene chloride or dichloroethane into the solution from (xii); and (xiv) collecting and drying the solid formed in (xiii).

A method comprising: (i) grinding gallnuts of a suitable plant to form crude gallnut powder; (ii) passing the crude gallnut powder from (i) though 40-mesh sieve to form fine gallnut powder; (iii) dissolving the fine gallnut powder in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring at 20-60° C. for 3-24 hrs; (iv) filtering the solution from (iii); (v) adding a suitable solvent (e.g., pentane, hexane, heptane, or a combination thereof) to the solution from (iv) and stirring for 3-24 hrs to form two organic layers; (vi) harvesting the oilier layer from (v); (vii) diluting the oiler layer from (vi) with a suitable solvent (e.g., acetone, acetonitrile, methyl ethyl ketone, ethyl acetate, methyl acetate, ethanol, or a combination thereof); (viii) stirring the solution from (vii) in the presence of charcoal for 1-24 hrs (e.g., 6-12 hrs or 12-18 hrs); (ix) stirring the mixture from (viii) in the presence of $Na_2CO_3$, $K_2CO_3$, $CaSO_4$ or $MgSO_4$; (x) removing charcoal, $Na_2CO_3$, $K_2CO_3$, $CaSO_4$ or $MgSO_4$ from the mixture from (ix) via routine practice; (xi) concentrating the filtrate from (x); (xii) dissolving the residue from (xi) in a suitable solvent (e.g., acetone, acetonitrile, methyl ethyl ketone, ethyl acetate, methyl acetate, ethanol, or a combination thereof); (xiii) adding methylene chloride or dichloroethane into the solution from (xii); and (xiv) collecting and drying the solid formed in (xiii).

A method comprising: (i) grinding gallnuts of a suitable plant to form crude gallnut powder; (ii) passing the crude gallnut powder from (i) though 40-mesh sieve to form fine gallnut power; (iii) dissolving the fine gallnut powder in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring at 20-60° C. for 3-24 hrs; (iv) stirring the solution from (iii) in the presence of charcoal for 1-24 hr (e.g., 6-12 hrs or 12-18 hrs); (v) stirring the mixture from (iv) in the presence of $Na_2CO_3$, $K_2CO_3$, $CaSO_4$ or $MgSO_4$; (vi) removing charcoal, $Na_2CO_3$, $K_2CO_3$, $CaSO_4$ or $MgSO_4$ from the mixture from (v) via routine practice; (vii) concentrating the filtrate from (vi); (viii) dissolving the residue from (vii) in a suitable solvent (e.g., acetone, acetonitrile, methyl ethyl ketone, ethyl acetate, methyl acetate, ethanol, or a combination thereof); (ix) adding methylene chloride or dichloroethane into the solution from (viii); and (x) collecting and drying the solid formed in (ix).

A method comprising: (i) grinding gallnuts of a suitable plant to form crude gallnut powder; (ii) passing the crude gallnut powder from (i) though 40-mesh sieve to form fine gallnut power; (iii) dissolving the fine gallnut powder in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring at 20-60° C. for 3-24 hrs; (iv) stirring the solution from (iii) in the presence of charcoal 1-24 hrs (e.g., 6-12 hrs or 12-18 hrs); (v) stirring the mixture from (iv) in the presence of $Na_2CO_3$, $K_2CO_3$, $CaSO_4$ or $MgSO_4$; (vi) removing charcoal, $Na_2CO_3$, $K_2CO_3$, $CaSO_4$ or $MgSO_4$ from the mixture from (v) via routine practice; (vii) reducing the volume of the filtrate from (vi) to about $1/10$ to $1/100$ of original volume; (ix) adding methylene chloride or dichloroethane into the solution from (vii); and (x) collecting and drying the solid formed in (ix).

A method comprising: (i) grinding gallnuts of a suitable plant to form crude gallnut powder; (ii) passing the crude gallnut powder from (i) though 40-mesh sieve to form fine gallnut power; (iii) dissolving the fine gallnut powder in a suitable solvent (e.g., acetone, acetonitrile, methyl ethyl ketone, ethyl acetate, methyl acetate, ethanol, isopropanol, tetrahydrofuran, 1,4-dioxane or a combination thereof) and stirring at 20-60° C. for 3-24 hrs; (iv) filtering the solution from (iii); (v) stirring the filtrate from (iv) in the presence of charcoal for 1-24 hrs (e.g., 6-12 hrs or 12-18 hrs); (vi) stirring the mixture from (v) in the presence of $Na_2CO_3$, $K_2CO_3$, $CaSO_4$ or $MgSO_4$; (vii) removing charcoal, $Na_2CO_3$, $K_2CO_3$, $CaSO_4$ or $MgSO_4$ from the mixture from (vi); (viii) concentrating the filtrate from (vii) via routine practice; (ix) dissolving the residue from (viii) in a suitable solvent (e.g., acetone, acetonitrile, methyl ethyl ketone, ethyl acetate, methyl acetate, ethanol, or a combination thereof); (x) adding methylene chloride or dichloroethane into the solution from (ix); and (xi) collecting and drying the solid formed in (x).

A method comprising: (i) grinding gallnuts of a suitable plant to form crude gallnut powder; (ii) passing the crude gallnut powder from (i) though 40-mesh sieve to form fine gallnut powder; (iii) placing the solution of fine gallnut powder from (ii) in a solvent (e.g., 50-30% methyl ethyl ketone/hexane) and stirring the mixture thus formed at RT for 3-24 hrs; (iv) filtering the solution from (iii); (v) dissolving the solid collected from (iv) in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring the solution at 20-60° C. for 3-24 hrs; (vi) filtering the solution from (v); (vii) stirring the filtrate from (vi) in the presence of charcoal 1-24 hrs; (viii) stirring the mixture from (vii) in the presence of $Na_2CO_3$, $K_2CO_3$, $CaSO_4$ or $MgSO_4$; (ix) removing charcoal, $Na_2CO_3$, $K_2CO_3$, $CaSO_4$ or $MgSO_4$ from the mixture from (viii) via routine practice; (x) concentrating the filtrate from (ix); (xi) dissolving the residue from (x) in a suitable solvent (e.g., acetone, acetonitrile, methyl ethyl ketone, ethyl acetate, methyl acetate, ethanol, or a combination thereof); (xii) adding methylene chloride or dichloroethane into the solution from (xi); and (xiii) collecting and drying the solid formed in (xii).

A method comprising: (i) grinding gallnuts of a suitable plant to form crude gallnut powder; (ii) passing the crude gallnut powder from (i) though 40-mesh sieve to form fine gallnut power; (iii) placing the fine gallnut powder from (ii) in a solvent (e.g., 20-60%, for example, 30-50%, methyl ethyl ketone/hexane) and stirring the solution thus formed at RT 3-24 hr; (iv) filtering the solution from (iii); (v) dissolving the solid collected from (iv) in a suitable solvent (e.g., acetone, acetonitrile, methyl ethyl ketone, ethyl acetate, methyl acetate, ethanol, isopropanol, tetrahydrofuran, 1,4-dioxane, or a combination thereof) and stirring the solution at 20-60° C. for 3-24 hrs; (vi) stirring the filtrate from (v) in the presence of charcoal for 1-24 hr (e.g., 6-12 or 12-18 hrs); (vii) stirring the mixture from (vi) in the presence of $Na_2CO_3$, $K_2CO_3$, $CaSO_4$ or $MgSO_4$; (viii) removing charcoal, $Na_2CO_3$, $K_2CO_3$, $CaSO_4$ or $MgSO_4$ from the mixture from (vii); (ix) reducing the volume the filtrate from (viii) to about 1/10 to 1/100 of the original volume; (x) dissolving the residue from (ix) in a suitable solvent (e.g., acetone, acetonitrile, methyl ethyl ketone, ethyl acetate, methyl acetate, ethanol, or a combination thereof); (xi) adding methylene chloride or dichloroethane into the solution from (x); and (xii) collecting and drying the solid formed in (xi).

A method comprising (i) grinding gallnuts of a suitable plant to form fine powder or small chips; (ii) extracting the find powder or small chips with a first solvent (e.g., those described herein) via the multiple-batch approach as described herein to produce a crude tannic acid extract; (iii) dissolving the crude tannic acid extract in water and mixing the tannic acid solution thus formed with $K_2CO_3$; (iv) extracting the mixture formed in (iii) with a suitable solvent (e.g., ethyl acetate) and collecting the organic layer thus formed; (v) mixing the organic layer with charcoal and stirring the mixture thus formed for a suitable period (e.g., 0.5 hour); (vi) incubating the mixture with $MgSO_4$ for a suitable period; (vii) filtering the mixture formed in (vi) through Celite and collecting the filtrate; (viii) mixing the filtrate (which may be diluted) with an alkyl solvent (e.g., hexane) and collecting the organic layer thus formed; (ix) optionally repeating step (viii); (x) collecting the resultant oily residues, which is optionally diluted in acetone, and mixing the oily residues with $CH_2Cl_2$; (xi) stirring the mixture thus formed for a suitable period allowing for precipitation of solid tannic acids; (xii) collecting the solid tannic acids, which can be dried under vacuum if needed; (xiii) slurrying the solid tannic acids with an alkyl solvent, a chlorinated solvent, or a combination thereof; (xiv) evaporating the mixture thus formed in vacuum; and (xv) optionally repeating step (xiv), thereby producing a tannic acid composition.

Figure 27:
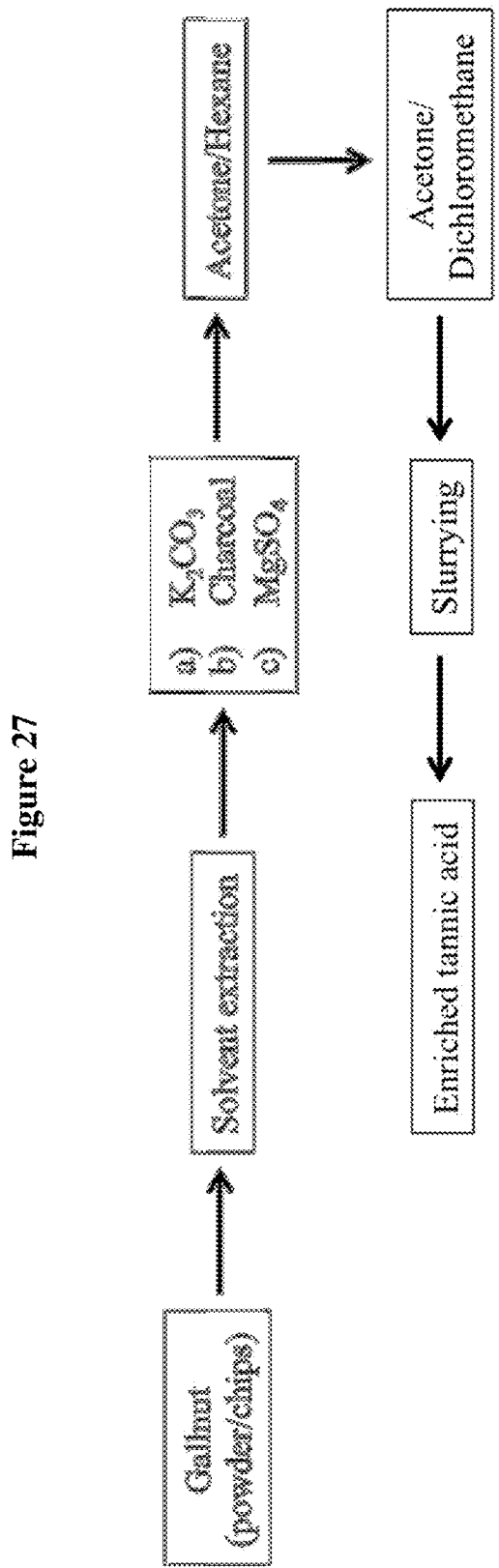
FIG. 27 is a schematic illustration of an exemplary enrichment method for preparing the tannic acid compositions described herein. See also Enrichment method 11 described below.

A schematic illustration of the above-described preparation method is provided in FIG. 27.

(B) Pharmaceutical Compositions

In some embodiments, the one or more tannic acids described herein (e.g., a mixture of tannic acids or a substantially homogenous population of tannic acids having a defined number of galloyl moieties as described herein) can be mixed with a pharmaceutically acceptable carrier (excipient) to form a pharmaceutical composition, which can be used for treating any of the target diseases as described herein. In some embodiments, the tannic acid population in the composition is substantially free of condensed tannins and/or phlorotannins. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

Pharmaceutically acceptable carriers include diluents, fillers, salts, buffers, stabilizers, solubilizers and other material which are well-known in the art. Exemplary pharmaceutically acceptable carriers for tannic acids or salts thereof in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from a suitable inorganic base, (e.g., sodium hydroxide, barium hydroxide, iron (ii) hydroxide, iron(III) hydroxide, magnesium hydroxide, calcium hydroxide, aluminium hydroxide, ammonium hydroxide, potassium hydroxide, caesium hydroxide, or lithium hydroxide) or a suitable organic base (e.g., pyridine, methyl amine, imidazole, benzimidazole, histidine, phosphazene bases, or a hydroxide of an organic cation such as quaternary ammonium hydroxide and phosphonium hydroxide). Also, pharmaceutically-acceptable salts can be prepared as alkaline metal or alkaline earth salts, such as lithium, sodium, potassium or calcium salts.

The tannic acid-containing pharmaceutical compositions as described herein can comprise pharmaceutically acceptable carriers, excipients, or stabilizers in the form of lyophilized formulations or aqueous solutions. Remington: The Science and Practice of Pharmacy 20th Ed. (2000) Lippincott Williams and Wilkins, Ed. K. E. Hoover. Such carriers, excipients or stabilizers may enhance one or more properties of the active ingredients (e.g., tannic acids) in the compositions described herein, e.g., bioactivity, stability, bioavailability, and other pharmacokinetics and/or bioactivities.

Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ (polysorbate), PLURONICS™ (nonionic surfactants), or polyethylene glycol (PEG).

In other examples, the pharmaceutical composition described herein can be formulated in sustained-release format. Suitable examples of sustained-release preparations include semipermeable matrices of solid hydrophobic polymers containing tannic acids, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation, or jntrathecal or intracerebral routes.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

In some embodiments, any of the tannic acid-containing pharmaceutical compositions may further comprise a second therapeutic agent based on the intended therapeutic uses of the composition.

In some examples, the second therapeutic agent is an anti-obesity agent, including, but not limited to, orlistat, lorcaserin, sibutramine, rimonabant, metformin, exenatide, pralintide, phentermine, fenfluramine, dexfenfluramine topiramate, dinitrophenol, bupropion, and zonisamide.

In other examples, the second therapeutic agent is an agent for treating a CNS disease/disorder. Such a therapeutic agent may be an antipsychotic drug. Exemplary antipsychotic drugs include, but are not limited to, butyrophenone (e.g., haloperidol (HALDOL™), phenothiazine (e.g., chlorpromazine (THORAZINE™), fluphenazine (PROLIXIN™), perphenazine (TRILAFON™), prochlorperazine (COMPAZINE™), thioridazine (MELLARIL™), trifluoperazine (STELAZINE™), mesoridazine, promazine, triflupromazine (VESPRIN™), levomepromazine (NOZINAN™), promethazine (PHENERGAN™), thioxanthene (e.g., chlorprothixene, flupenthixol (DEPIXOL™ FLUANXOL™), thiothixene (NAVANE™), zuclopenthixol (CLOPIXOL™ ACUPHASE™), clozapine (CLOZARIL™), olanzapine (ZYPREXA™), risperidone (RISPERDAL™, RISPERDAL CONSTA™), quetiapine (SEROQUEL™), ziprasidone (GEODON™), amisulpride (SOLIAN™), asenapine, paliperidone (INVEGA®), aripiprazole (ABILIFY™), dopamine partial agonists (BIFEPRUNOX™, NORCLOZAPINE™ (ACP-104)), lamotrigine (LAMICTAL™), tetrabenazine (NITOMAN™, XENAZINE™) cannabidiol, LY2140023, and the like).

Alternatively, the second therapeutic agent can be an antidepressant and/or mood stabilizer. In certain embodiments the antidepressant comprises a monoamine oxidase inhibitor (MAOI), a tricyclic antidepressant (TCA), a tetracyclic antidepressant (TeCA), a selective serotonin reuptake inhibitor (SSRI), a noradrenergic and specific serotonergic antidepressant (NASSA), a norepinephrine (noradrenaline) reuptake inhibitor, a norepinephrine-dopamine reuptake inhibitor, and/or a serotonin-norepinephrine reuptake inhibitor (SNRI). Exemplary SSRIs include fluoxetine (PROZAC™), paroxetine (PAXIL™ SEROXAT™), escitalopram (LEXAPRO™, ESIPRAM™), citalopram (CELEXA™), sertraline (ZOLOFT™), fluvoxamine (LUVOX™)). Exemplary SNRIs include venlafaxine (EFFEXOR™), milnaciprim and duloxetine (CYMBALTA™). Additional antidepressant include a noradrenergic and specific serotonergic antidepressant (NASSA) (e.g., mirtazapine (AVANZA™, ZISPIN™, REMERON™), or mianserin, a norepinephrine (noradrenaline) reuptake inhibitor (NRI) (e.g., reboxetine (EDRONAX™)), a norepinephrine-dopamine reuptake inhibitors (e.g., bupropion (WELLBUTRIN™, ZYBAN™)), amitriptyline, nortriptiline, protriptyline, desipramine, imipramine, trimipramine, amoxapine, bupropion, bupropion SR, clomipramine, doxepin, isocarboxazid, venlafaxine XR, tranylcypromine, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, and the like.

In other examples, the second therapeutic agent can be an agent for the treatment of ADD and/or ADHD. Suitable ADHD medications include, but are not limited to amphetamine, modafinil, desoxyn, methamphetamine, cocaine, arecoline, dexmethylphenidate (focalin, focalin XR), dextroamphetamine (dexedrine, dexedrine spansules, dextroamphetamine ER, dextrostat), methylphenidate (concerta, daytrana, metadate CD, metadate ER, methylin, methylin ER, ritalin, ritalin-LA, ritalin-SR), lisdexamfetamine dimesylate (Vyvanse), mixed salts amphetamine (Adderall, Adderall XR), atomoxetine (Strattera), clonidine hydrochloride (Catapres), guanfacine hydrochloride (Tenex), arecoline, and pemoline.

Further, the second therapeutic agent may be an agent for use in treating a cognitive disorder, and/or a condition characterized by neurodegeneration (e.g., Alzheimer's disease, or Parkinson's disease). Such therapeutic agents include, but are not limited to tacrine, rivastigmine, memantine (AXURA™, AKATINOL™, NAMENDA™, EBIXA™ ABIXA™), donepezil (Aricept™), physostigmine, nicotine, arecoline, huperzine alpha, selegiline, Rilutek™ (riluzole), vitamine c, vitamine e, carotenoids, ginkgo biloba, and the like.

(C) Health Food Products

In some embodiments, the tannic acid-containing compositions described herein can be a health food product, which can be any kinds of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, or for facilitating treatment of any of the target diseases noted herein (e.g., an obesity disorder, hyperlipidemia, hyperglycemia, diabetes, or a CNS disorder, including those described herein). The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein, containing one or more tannic acids (e.g., the tannic acid mixture described herein or the substantially homogenous population of a tannic acid having a defined number of galloyl moieties as also described herein), may comprise one or more edible carriers, which confer one or more of the benefits to the tannic acids in the product as described herein. Examples of edible carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, flax seed oil, and/or benzoate.

In some examples, the healthy food product is a nutraceutical composition, which refers to compositions containing components from food sources and conferring extra health benefits in addition to the basic nutritional value found in foods. A nutraceutical composition as described herein comprises the tannic acid content described herein (e.g., the tannic acid mixture or the substantially homogenous tannic acid population as described herein) and additional ingredients and supplements that promote good health and/or enhance stability and bioactivity of the tannic acids.

The actions of nutraceutical compositions may be fast or/and short-term or may help achieve long-term health objectives as those described herein, e.g., improving basic behavioral functioning, hyperactivity, anxiety, depression, sensorimotor gating, pain threshold, memory and/or cognitive functioning in, e.g., human subjects who have or are at risk for diseases associated with DAAO such as CNS disorders or human subjects who have or are at risk for an obesity disorder. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or *acacia*); non-aqueous vehicles (for example, almond oil, oily esters, ethyl alcohol or fractionated vegetable oils); and preservatives (for example, methyl or propyl-p-hydroxybenzoates, benzoate or sorbate).

The health food products described herein may further comprise one or more second therapeutic agents, including those described herein.

(D) Medical Food Products

The present disclosure also provides compositions of medical food products, use in improving basic behavioral functioning, hyperactivity, anxiety, depression, sensorimotor gating, pain threshold, memory and/or cognitive functioning, and/or for treating a target disease as described herein (e.g., an obesity disorder, hyperlipidemia, hyperglycemia, diabetes, or a CNS disorder). A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management.) In some examples, a medical food composition described herein is not one of those that would be simply recommended by a physician as part of an overall diet to manage the symptoms or reduce the risk of a disease or condition.

Any of the medical food compositions described herein, comprising one or more tannic acid molecules or salts thereof and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the tannic acid content in the composition, for example, stability, bioavailability, and/or bioactivity. Any of the carriers described herein may be used for making the medical food composition. In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

(E) Kits

The present disclosure also provides kits for use in improving basic behavioral functioning, hyperactivity, anxiety, depression, sensorimotor gating, pain threshold, memory and/or cognitive functioning, and/or for treating a target disease as described herein (e.g., an obesity disorder, hyperlipidemia, hyperglycemia, diabetes, or a CNS disorder). Such kits can include one or more containers comprising a tannic acid-containing composition as described herein and optionally one or more of the second therapeutic agents as also described herein.

In some embodiments, the kit can comprise instructions for use in accordance with any of the methods described herein. The included instructions can comprise, for example, a description of administration of the tannic acid-containing composition and optionally a description of administration of the second therapeutic agent(s) to improve basic behavioral functioning, hyperactivity, anxiety, depression, sensorimotor gating, pain threshold, memory and/or cognitive functioning, or to treat a target disease as described herein. The kit may further comprise a description of selecting an individual suitable for treatment based on identifying whether that individual has the disease or is at risk for the disease. In still other embodiments, the instructions comprise a description of administering one or more agents of the disclosure to an individual at risk of the disease or to an individual who is in need of improving basic behavioral functioning, hyperactivity, anxiety, depression, sensorimotor gating, pain threshold, memory and/or cognitive functioning.

The instructions relating to the use of the tannic acid-containing composition to achieve the intended therapeutic effects generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert may indicate that the composition is used for the intended therapeutic utilities. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

II. Applications of Tannic Acid-Containing Compositions

Any of the tannic acid-containing compositions described herein may be used to improve basic behavioral functioning, weight reduction, hyperactivity, anxiety, depression, suicidal ideation and/or behavior, sensorimotor gating, pain threshold, memory, and/or cognitive functioning in a subject in need of the treatment. Such compositions may also be used to treating diseases or disorders associated with DAAO such as a central nervous disorder (e.g., those described herein). The compositions may also be used to treating an obesity disorder.

As used herein, the term "treating" refers to the application or administration of a composition including one or more active agents to a subject, who is in need of the treatment, for example, having a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a tannic acid-containing composition may be administered to a subject in need of the treatment via a suitable route.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

A human subject who needs the treatment may be a human patient having, at risk for, or suspected of having a target disease/disorder, such as a CNS disorder, or a disease associated with obesity, e.g., diabetes, hyperglycemia, hypercholesterolemia or hyperlipidemia. A subject having a target disease or disorder can be identified by routine medical examination, e.g., laboratory tests, organ functional tests, and/or behavior tests. A subject suspected of having any of such target disease/disorder might show one or more symptoms of the disease/disorder. A subject at risk for the disease/disorder can be a subject having one or more of the risk factors for that disease/disorder, for example, a genetic factor. In some instances, the human subject is a child who has, is suspected of having, or is at risk for obesity or a CNS disorder associated with children, for example, attention deficit/hyperactivity disorder (ADHD), autism, Asperger's disorder, obsessive compulsive disorder, depression, psychosis, chronic pain, and learning disorder.

The methods and compositions described herein may be used to treat a CNS disorder. Exemplary CNS disorders that can be treated by the methods and compositions described herein include attention deficit/hyperactivity disorder (ADHD), schizophrenia, pain, depression, suicidal ideation and/or behavior, bipolar disorder, tic disorder, post-traumatic stress disorder, anxiety, social anxiety disorder, panic disorder, autism, Asperger's disorder, obsessive-compulsive disorder, learning disorder, Tourette's syndrome, mild cognitive impairment, dementia, vascular dementia, a neurodegenerative disorder (e.g., Alzheimer's disorder or Parkinson's disease, frontotemporal dementia, Huntington's disease), nocturnal enuresis, blepharospasm, non-epileptic seizure, psychosis, mania, cerebral malaria and behavior and psychological symptoms of dementia (BPSD).

A disease associated with obesity includes diseases and disorders that lead to obesity, as well as diseases and disorders that have a high occurrence rate in obesity patients. Obesity is a medical condition characterized by accumulation of excess body fat to the extent that it may have a negative effect on health. Obesity may be determined by body mass index (BMI), a measurement obtained by dividing a person's weight by the square of the person's height. For example, BMI over 30 $kg/m^2$ may indicate obesity. Exemplary diseases associated with obesity include, but are not limited to, eating disorders, anorexia nervosa, bulimia nervosa, stroke, coronary heart disease, heart attack, congestive heart failure, congenital heart disease, hypertension, non-alcoholic steatohepatitis, insulin resistance, hyperuricemia, hypothyroidism, osteoarthritis, gallstones, infertility, obesity hypoventilation syndrome, obstructive sleep apnea, chronic obstructed pulmonary disease, and asthma.

As used herein, "an effective amount" refers to the amount of each active agent (e.g., the tannic acid mixture or the substantially homogenous population of tannic acids as described herein) required to confer therapeutic effect on the subject, either alone or in combination with one or more other active agents, such as one or more of the second therapeutic agents described herein. In some embodiment, the therapeutic effect is to inhibit the activity of DAAO (e.g., by at least 20%, 30%, 40%, 50%, 60%, 70%, 80%, 90%, 95%, or higher) in the subject. In some embodiments, the therapeutic effect is improvement of basic behavioral functioning, weight reduction, hyperactivity, anxiety, depression, sensorimotor gating, pain threshold, memory, and/or improvement of cognitive functioning. In some embodiments, the therapeutic effect is alleviating one or more symptoms associated with any of the CNS disorders described herein. Alternatively or in addition, the therapeutic effect is maintaining or reducing body weight of the subject.

Determination of whether an amount of the composition as described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration, genetic factors and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a composition as described herein may be appropriate. Various formulations and devices for achieving sustained release are known in the art.

Generally, for administration of any of the compositions, an exemplary daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering one or more initial doses at a suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to four times a day or a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency can be three times a day, twice a day, once a day, once every other day, once every week, once every 2 weeks, once every 4 weeks, once every 2 months, or once every 3 months. The dosing regimen can vary over time.

In some embodiments, for an adult patient of normal weight, doses ranging from about 0.3 to 50.00 mg/kg/day (e.g., 0.5 to 40 mg/kg/day, 1-30 mg/kg/day, 5-30 mg/kg/day, or 10-20 mg/kg/day) may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a tannic acid-composition as described herein will depend on the specific tannic acid or tannic acid mixture, and/or other active ingredient employed, the type and severity of the disease/disorder, whether the composition is administered for preventive or therapeutic purposes, previous therapy, the patient's clinical history and response to the DAAO inhibitor, and the discretion of the attending physician. Typically the clinician will administer a composition, until a dosage is reached that achieves the desired result.

Conventional methods, known to those of ordinary skill in the art of medicine, can be used to administer the composition (e.g., a pharmaceutical composition, a health food composition, a nutraceutical composition or a medical food composition) to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-week, half (or two week)-, 1-, 3-, or 6-month depot injectable or biodegradable materials and methods. In some examples, the pharmaceutical composition is administered intraocularlly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water-soluble antibodies can be administered by the drip method, whereby a pharmaceutical formulation containing tannic acids and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of tannic acids, can be dissolved and administered in a pharmaceutical excipient such as Water-for-Injection, 0.9% saline, or 5% glucose solution.

In one embodiment, a tannic acid-containing composition is administered via a site-specific or targeted local delivery technique. Examples of site-specific or targeted local delivery techniques include various implantable depot sources of the tannic acid-containing compositions or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Treatment efficacy for a target disease/disorder can be assessed by methods well-known in the art.

III. Combined Therapy

Also provided herein are combined therapies using any of the tannic acid-containing compositions described herein and a second therapeutic agent, such as those described herein. The term combination therapy, as used herein, embraces administration of these agents (e.g., a tannic acid-containing composition and an anti-CNS disorder or anti-obesity agent) in a sequential manner, that is, wherein each therapeutic agent is administered at a different time, as well as administration of these therapeutic agents, or at least two of the agents, in a substantially simultaneous manner. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a tannic acid-containing composition) can be administered orally, and a second agent (e.g., an anti-CNS disorder agent or an anti-obesity agent) can be administered intravenously.

As used herein, the term "sequential" means, unless otherwise specified, characterized by a regular sequence or order, e.g., if a dosage regimen includes the administration of a tannic acid-containing composition and an anti-CNS disorder or anti-obesity agent, a sequential dosage regimen could include administration of the tannic acid-containing composition before, simultaneously, substantially simultaneously, or after administration of the anti-CNS disorder or anti-obesity agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the agents described herein.

Combination therapy can also embrace the administration of the agents described herein (e.g., a tannic acid-containing composition and an anti-CNS disorder or anti-obesity agent) in further combination with other biologically active ingredients (e.g., a different anti-CNS disorder agent) and non-drug therapies (e.g., surgery).

It should be appreciated that any combination of a tannic acid-containing composition and a second therapeutic agent (e.g., an anti-CNS disorder or anti-obesity agent) may be used in any sequence for treating a target disease. The combinations described herein may be selected on the basis of a number of factors, which include but are not limited to the effectiveness of inhibiting DAAO, improving basic behavioral functioning, weight reduction, hyperactivity, anxiety, depression, sensorimotor gating, pain threshold, memory or enhancing cognitive functioning, and/or alleviating at least one symptom associated with the target disease, or the effectiveness for mitigating the side effects of another agent of the combination. For example, a combined therapy described herein may reduce any of the side effects associated with each individual members of the combination, for example, a side effect associated with the second therapeutic agent.

IV. General Techniques

The practice of the present invention will employ, unless otherwise indicated, conventional techniques of neuroscience, molecular biology (including recombinant techniques), microbiology, cell biology, biochemistry and immunology, which are within the skill of the art. Such techniques are explained fully in the literature, such as, Current protocol in Neuroscience (Developmental Editor: Eric Prager, Online ISBN: 9780471142300, DOI: 10.1002/0471142301). Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The specific embodiments provided herein are, therefore, to be construed as merely illustrative, and not limitative of the remainder of the disclosure in any way whatsoever. All publications cited herein are incorporated by reference for the purposes or subject matter referenced herein.

Example 1. Identification of Potent Moieties of Tannic Acid and Determination of its Effectiveness for Treating Central Nervous System (CNS) Disorders The activity of tannic acids for inhibiting D-amino acid oxidase (DAAO) was determined as follows.

The activity of DAAO was determined in vitro by measuring the inhibition of the catabolism of known substrate, D-proline. The cofactor FAD (40 $\mu$M) was added to the DAAO stock solution first. For the assay, potential inhibitors of tannic acid(s) were mixed with reaction mixture containing phosphate buffered saline (137 mM NaCl, 3 mM KCl, 10 mM $Na_2HPO_4$, 2 mM $NaH_2PO_4$, pH 7.4), horseradish peroxidase (5 U/ml), o-phenylendiamine (OPD, 0.03%), and 0.6 µg human-(or porcine-) DAAO, and incubated for about 5 min. After the pre-incubation period, 40 mM D-proline were added as substrate and the reaction continued for 10 min. OPD was oxidized to form 2,3-diaminophenazine (DAP) by horseradish peroxidase. The absorbance of DAP was measured at 453 nm by a spectrophotometry. Assay was done in serial dilutions of the inhibitors to generate $IC_{50}$ and analyzed by Prism (Graphpad Software). In the analysis, the spectrophotometry readings were fit to a standard equation to determine the concentration of 50% inhibition ($IC_{50}$). All enzymatic assays were conducted at room temperature in 96-well plate format.

As shown in FIG. 1, crude tannic acids as a group showed a strong D-amino acid oxidase (DAAO) inhibitory activity with an $IC_{50}$ value of 5.47 µM.

Figure 2:
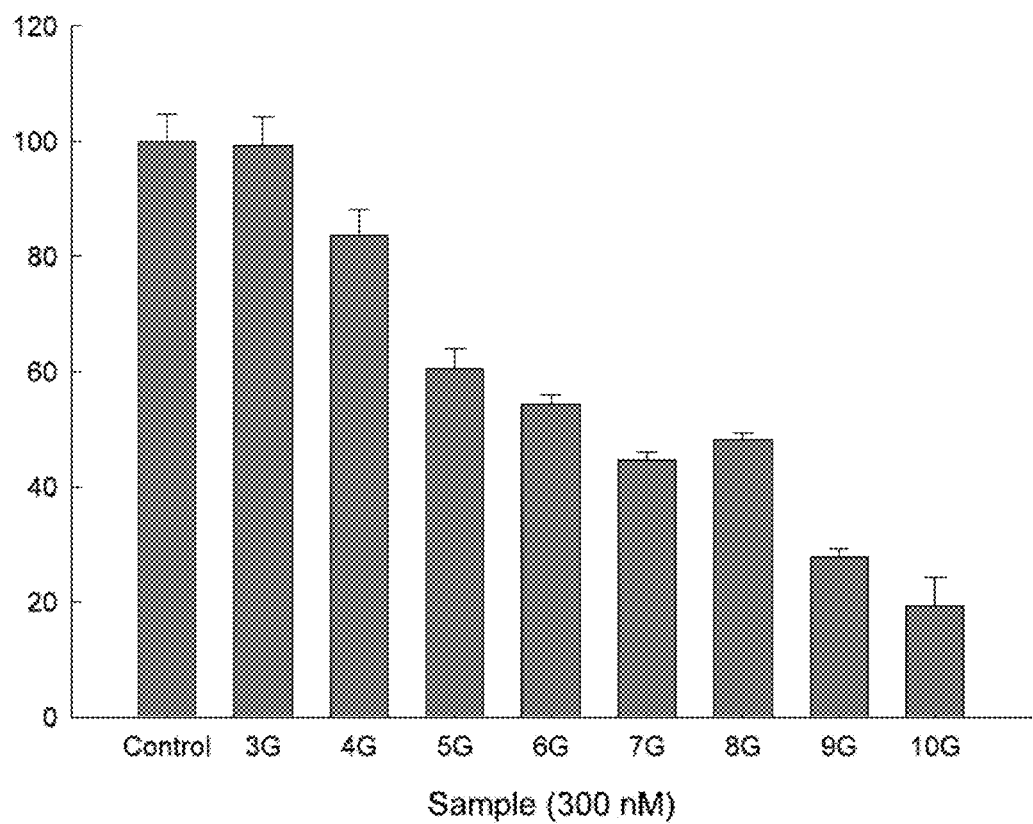
FIG. 2 is a chart showing the anti-DAAO activities of tannic acids with different numbers of galloyl moieties at 300 nM. 3 galloyl moieties showed low activity. Tannic acids with four or more 4 galloyl moieties showed higher activity in inhibiting DAAO as compared with tannic acids with 3 galloyl moieties. The higher the number of galloyl moieties, the stronger the potency in inhibiting DAAO.

The DAAO inhibitory activities of subgroups of tannic acids (having a particular number of galloyl moieties) were determined as follows. Tannic acid fractions having different numbers of galloyl moieties were separated by a reversed-phase column (LiChroprep® RP-18) with a mobile phase of acetonitrile and distilled water in gradient elution. The DAAO inhibitory activity of each tannic acid fraction at 80 µM (Table 1) and 300 nM (FIG. 2, Table 2) was analyzed by the method described above, using distilled water and 10% DMSO aqueous solution as blank controls and sodium benzoate as a positive control.

TABLE 2

DAAO-inhibitory Activities of Individual Tannic Acids

| Samples (80 µM) | Relative DAAO activity (%) | SEM |
|---|---|---|
| H₂O | 100.00 | 1.01 |
| 10% DMSO | 100.00 | 1.97 |
| Sodium Benzoate | 38.05 | 0.46 |
| Fraction 7 (2 galloyl) | 24.35 | 0.72 |
| Fraction 9 (2 galloyl) | 26.42 | 0.20 |
| Fraction 13 (3 galloyl) | 13.17 | 0.20 |
| Fraction 15 (4 galloyl) | 6.71 | 0.14 |
| Fraction 19 (5 galloyl) | 5.62 | 0.17 |
| Fraction 20 (6 galloyl) | 5.63 | 0.30 |
| Fraction 22 (7 galloyl) | 5.16 | 0.36 |
| Fraction 24 (8~9 galloyl) | 7.45 | 0.13 |

Table 2 shows the anti-DAAO activities of tannic acids with different numbers of galloyl moieties. Tannic acids with four or more 4 galloyl moieties showed much higher activity in inhibiting DAAO as compared with tannic acids with less than 4 galloyl moieties. All DAAO assays were done with 80 µM of tannic acids.

TABLE 3

DAAO-inhibitory Activities of Individual Tannic Acids

| Sample (300 nM) | Relative DAAO activity (%) | SD |
|---|---|---|
| Control | 100.00 | 4.74 |
| 3G | 99.25 | 5.01 |
| 4G | 83.67 | 4.55 |
| 5G | 60.41 | 3.62 |
| 6G | 54.19 | 1.81 |
| 7G | 44.60 | 1.39 |
| 8G | 48.23 | 1.17 |
| 9G | 27.92 | 1.36 |
| 10G | 19.25 | 5.13 |

Table 3 shows the anti-DAAO activities of tannic acids with different numbers of galloyl moieties at 300 nM. 3 galloyl moieties showed weak activity, while the higher numbers of galloyl moieties showed significantly higher inhibition of DAAO activities. (G=number of galloyl group)

TABLE 4

Potency of Individual Tannic Acids

| | 3G | 4G | 5G | 6G | 7G | 8G | 9G | 10G |
|---|---|---|---|---|---|---|---|---|
| $IC_{50}$ (µM) | 8.474 | 1.576 | 0.496 | 0.375 | 0.256 | 0.337 | 0.240 | 0.215 |
| Std. Error | 0.031 | 0.020 | 0.019 | 0.014 | 0.014 | 0.012 | 0.011 | 0.008 |

Tables 4 and 5 show the $IC_{50}$ (µM) of anti-DAAO activities of tannic acids with different numbers of galloyl moieties. The $IC_{50}$ were determined for each tannic acid with different numbers of galloyl moieties, which indicating potent tannic acids with more than 3 galloyl moieties. Tannic acids with four or more 4 galloyl moieties showed much smaller IC50 and more potent in inhibiting DAAO as compared with tannic acids with less than 4 galloyl moieties. (G=number of galloyl group).

TABLE 5

Tannic acid purification with 4-9 galloyl moieties (4-9 G) exhibits stronger potency than the tannic acid mixture.

| Sample | Tannic Acids | 4-9 G |
|---|---|---|
| $IC_{50}$ (µg/ml) | 0.515 | 0.361 |
| Std. Error | 0.020 | 0.017 |

Therefore, purification of tannic acids with more than 3 galloyl moieties enriches the potency as indicated by the smaller $IC_{50}$, as compared to the tannic acid mixture (Tables 4 and 5). The results show that tannic acids having more than 3 galloyl moieties (e.g., 4-10) exhibited higher DAAO inhibition potency than the tannic acids having 3 and less galloyl moieties.

Figure 3:
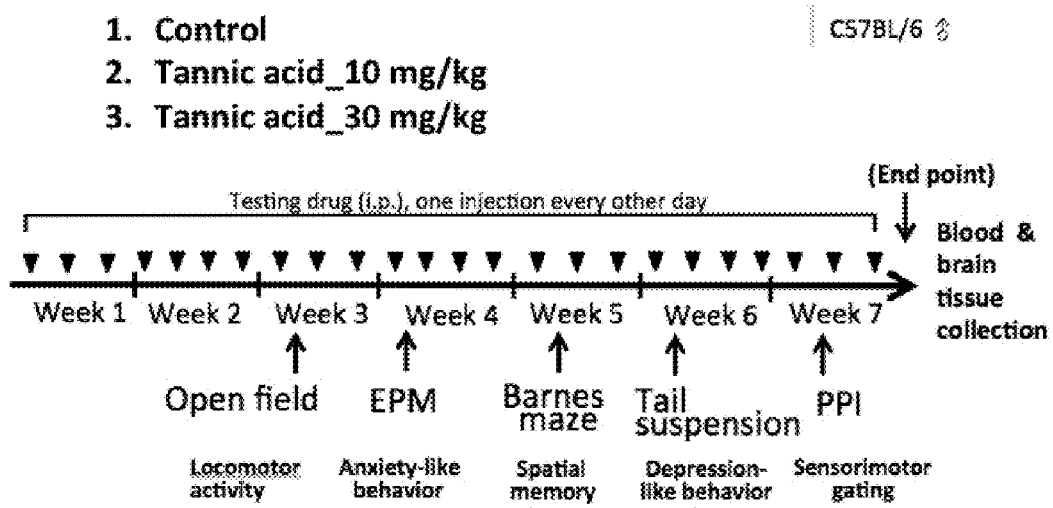
FIG. 3 is a schematic illustration of an exemplary design for verifying the activity of tannic acids on improving basic behavioral functioning, anxiety, depression, memory, sensorimotor gating and cognitive behaviors. The mice received either a vehicle control or tannic acids at 10 mg/kg or 30 mg/kg by injection every other day. Body weights of the treated mice were measured every other day. The behavioral tests were performed on days that injections were not administered.

Example 2. The Effects of Tannic Acid on Basic Behavioral Functioning and Cognitive Behaviors The objective of this study was to verify the effects of multiple doses of tannic acids on basic metabolism, behavioral functioning, and cognitive behaviors. In this experiment, the body weight, spontaneous locomotion activity, anxiety-like behaviors, spatial learning and memory, depressive-like behaviors and sensorimotor gating function of each mouse were examined following the repeated injections or oral administrations of tannic acids. These activities are known to be mediated by the NMDA receptor. (Wu et al., *PNAS;* 110(36):14765-70 (2013); Furuya et al., *Eur J Pharmacol,* 364(2-3):133-140 [1999]; Lai et al., *Curr Pharm Des,* 20(32):5139-5150 [2014]; McLamb et al., *Pharmacol Biochem Behav,* 37(1):41-45 [1990]; Vardigan et al., *Pharmacol Biochem Behav,* 95(2):223-229 [2010]; Wiley et al, *Eur J Pharmacol,* 294(1):101-107 [1995]; Wu et al., *Psychopharmacology (Berl),* 177(3):256-263 [2005]). An exemplary illustration of this study is shown in FIG. 3.

Methods and Materials
Animal and Housing Conditions

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies were performed during the dark cycle. All animals used in this study were adult mice (at least 2.5 months of age).

Repeated Injections of Tannic Acid

Tannic acids were purchased from Sigma (Sigma-Aldrich, USA). The adult mice were randomly assigned to three groups: (1) control, (2) tannic acid (10 mg/kg), and (3) tannic acid (30 mg/kg), which were treated, respectively, by a vehicle control (PBS), tannic acid at 10 mg/kg, and tannic acid at 30 mg/kg. Two weeks prior to the behavioral tests, all mice were injected intraperitoneally (i.p.) with either the vehicle control or tannic acid every other day. The body weight of each mouse, which served as an index of its physical development and metabolism, was recorded on the day of injection.

Examination the Effects of Repeated Injections of Tannic Acid on Mouse Basic Behavior Functioning and Cognitive Behaviors All mice treated with either the vehicle control or the tannic acids as described above were tested sequentially by 5 tasks: (1) open field task for spontaneous locomotion test, (2) anxiety-like behaviors test by elevated plus maze, (3) spatial learning and memory test by Barnes maze, (4) depressive-like behaviors test by tail suspension, and (5) sensorimotor function test by prepulse inhibition. At least a 1-week interval was made between different tasks. In order to minimize carryover effects, the tasks were arranged in the sequence to ensure that the more stressful task did not occur prior to a less stressful one. The procedures are described in Current protocol in Neuroscience (Developmental Editor: Eric Prager, Online ISBN: 9780471142300, DOI: 10.1002/0471142301), the relevant disclosures of which are incorporated by reference herein for the intended purposes.

Results

Physical Development and Weight Reduction

Figure 4:
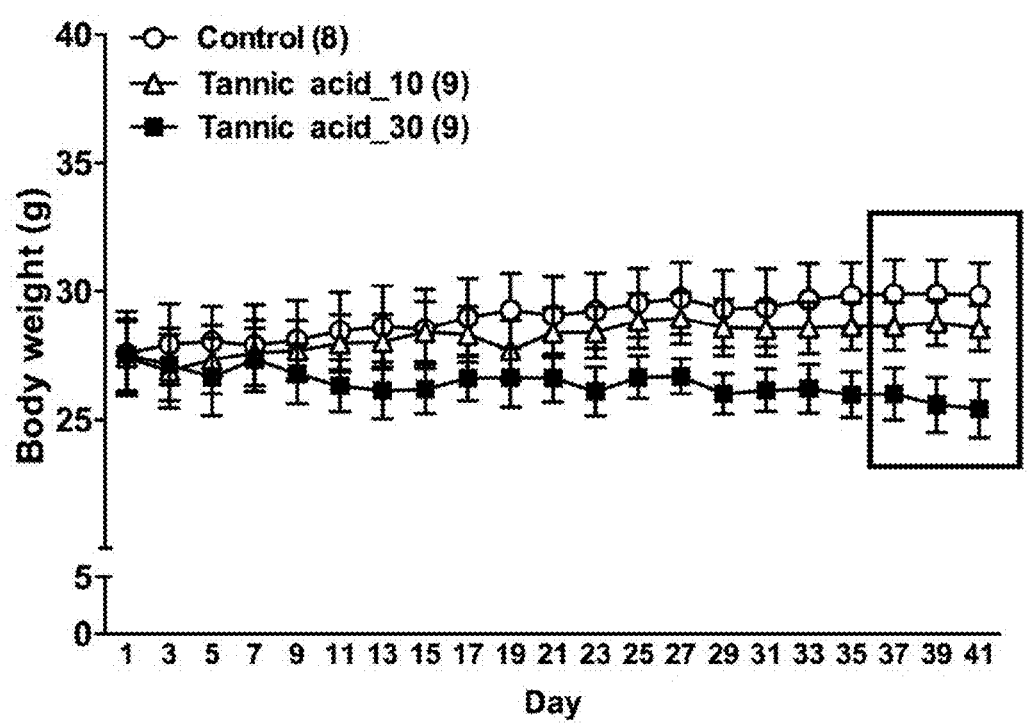
FIG. 4 is a chart showing the body weight changes of mice treated with a vehicle control and tannic acids at various doses as indicated during the course of the treatment. Tannic acid at 10 mg/kg arrests the weight gain while 30 mg/kg reduces the weight. This is an example for tannic acid for weight reduction and to treat obesity disorders

During the period of repeated injections, the body weight of the tannic acid (10 mg/kg) group were increased at a level lower than that of the control group, while the body weight of the tannic acid (30 mg/kg) was much lighter than the controls. See FIG. 4.

Spontaneous Locomotor Activity

Figure 5:
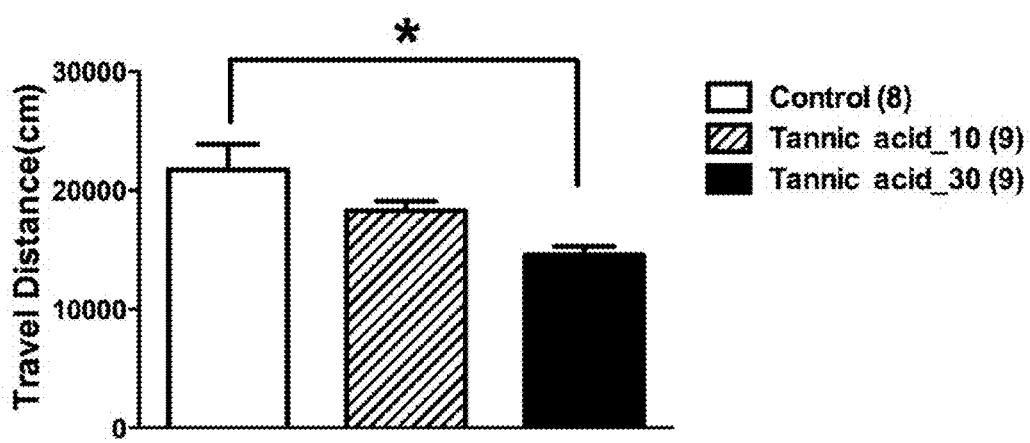
FIG. 5 is a chart showing dose-dependent reduction of the spontaneous locomotion activities of mice after repeated injections of tannic acids or a vehicle control.

The open field task is a common measurement of novelty induced exploratory behavior and general activity in both mice and rats. In this study, the mice were placed in a PLEXIGLAS® cage (37.5 cm×21.5 cm×18 cm) under 50-65 lux light intensity. Their spontaneous locomotor activities were measured for 60 minutes using the EthoVision video tracking system (Noldus Information Technology, the Netherlands). The travel distance of each mouse was measured as an index of locomotion activity. As shown in FIG. 5, tannic acids reduced the travel distances of the treated mice in a dose-dependent manner.

Figure 6:
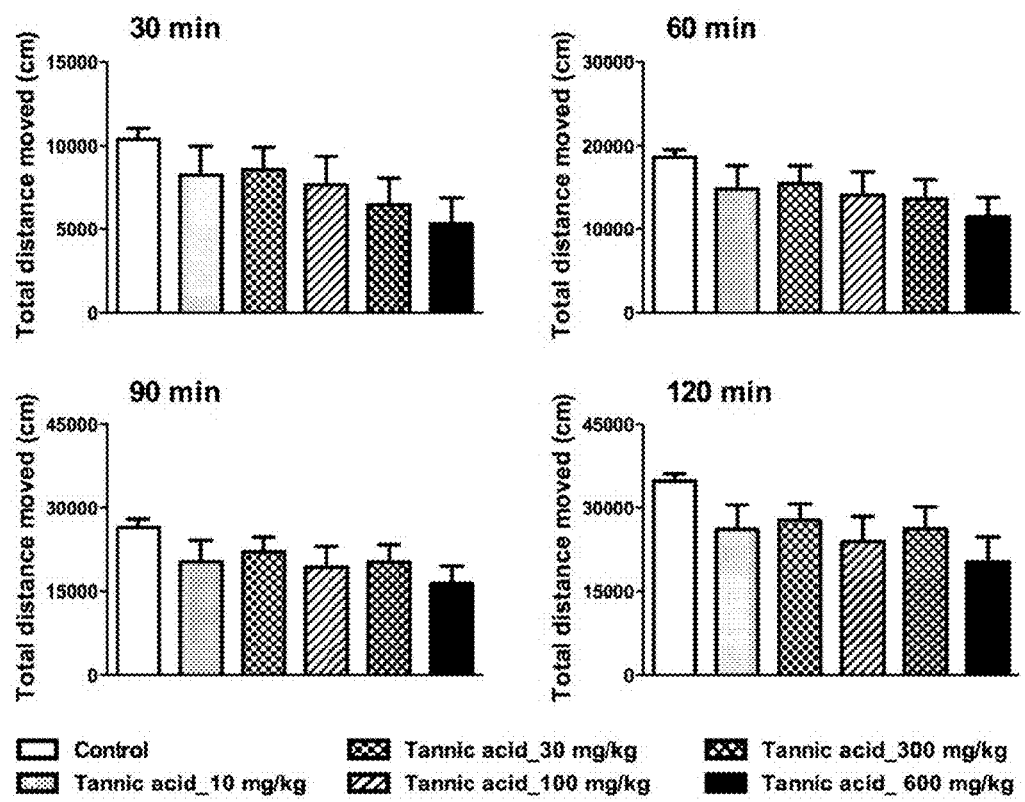
FIG. 6 is a chart showing that tannic acids (Merck Millipore, Germany) by a single oral gavage at the various doses as indicated dose-dependently reduced locomotion activity in mice in a dose-dependent manner.

A similar experiment was carried out, in which mice were administered orally at 10 mg/kg, 30 mg/kg, 100 mg/kg, 300 mg/kg, and 600 mg/kg for a single dose and their locomotion activities were measured for 30 minutes, 60 minutes, 90 minutes, and 120 minutes. Tannic acids at all tested doses reduced the locomotion of the treated mice as compared with the mice treated with the vehicle control. The results are illustrated in FIG. 6.

Anxiety-Like Behaviors

An elevated plus maze consisting of two open arms and two closed arms was used to assess the instinctively anxious behavior. The maze was elevated 50 cm from the floor with two open arms (each 50 cm long×10 cm wide), two closed arms plus 45 cm high walls without a roof (each 50 cm long×10 cm wide), and a square shaped central platform (10×10 cm). Each mouse was placed in the central platform and faced toward one of the closed arms for observation under 50-65 lux light intensity for 5 minutes. The time spent on each part of the maze and travel distance on each part of maze was recorded by the EthoVision tracking system (Noldus Information Technology, the Netherlands).

Figure 7:
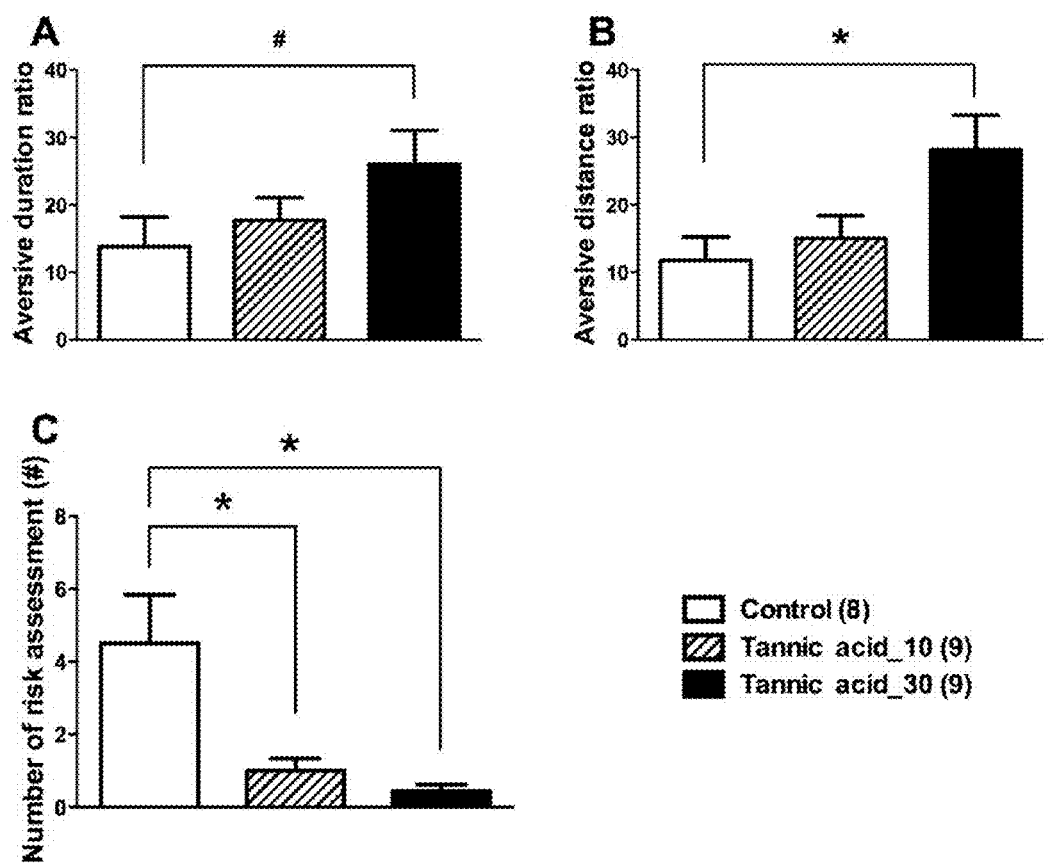
FIG. 7 includes diagrams showing the dose-dependent improvement of anxiety-like behaviors of the mice after repeated injections of tannic acids vs. vehicle control. Panel A: aversive duration of each group. Panel B: aversive distance ratio of each group. Panel C: number of risk assessments of each group.

The aversive duration ratio of each group was shown in FIG. 7, Panel A. In comparison to the control group, the tannic acid (30 mg/kg) group displayed marginal higher aversive duration ratios whereas the tannic acid (10 mg/kg) group did not. The aversive distance ratio of each group was shown in FIG. 7, Panel B. The tannic acid (30 mg/kg) group displayed significant higher aversive distance ratios as compared with the control group. The number of risk assessments of each group is displayed in FIG. 7 Panel C. As compared to the control group, both tannic acid groups displayed significant lower risk assessments (all $p<0.05$).

Spatial Learning and Memory

Figure 8:
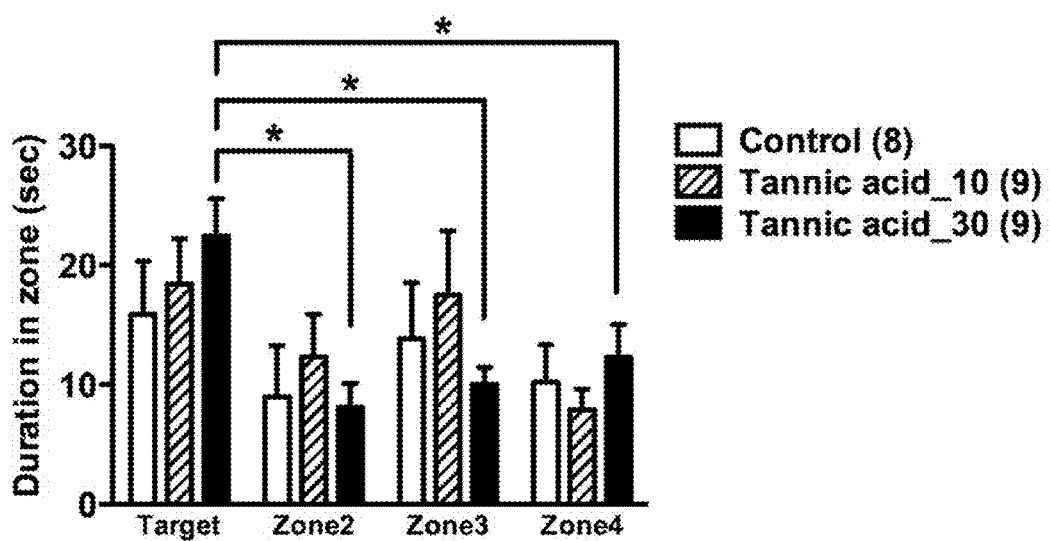
FIG. 8 is a chart showing the dose-dependent improved performance of spatial memory retrieval of mice after repeated injections of tannic acid vs. vehicle control. 30 mg/kg group of animals perform better than 10 mg/kg group.

Mice were tested in the Barnes maze to examine their spatial learning and memory as described previously (Barnes, *J Comp Physiol Psychol*, 93(1):74-104 [1979]). This paradigm has been commonly examined in mouse models of CNS disorders, including, but not limited to schizophrenia, depressions, obsessive compulsive disorder, post-traumatic stress disorder, addiction disorders, Alzheimer's disease, frontotemporal dementia, Parkinson's disease, Duchenne muscular dystrophy, stroke, and Fragile X syndrome (see Cook et al., 2014; Gotz and Ittner, 2008; Hendriksen and Vles, 2008; Conklin et al., 2000; Song et al., 2006; Lai et al., 2014; Vasterling et al., 2002; Hyman, 2005; Schaar et al., 2010; Santos et al., 2014; Zhu et al., 2007; Deckersbach et al., 2000). The testing apparatus was an elevated (50 cm above the floor) circular PLEXIGLAS® plate (100 cm in diameter) with 20 holes (7 cm in diameter, 7 cm between holes) evenly spaced around the perimeter. The mice were trained on the plate to identify an escape box (25×8×6 cm) hidden behind the target hole, which was designated as an analog to the hidden platform in the Morris water maze task. The location of the target hole was selected for each mouse but randomized across mice. Mice were initially placed at the center of the plate covered by an opaque cylinder, and the cylinder was removed 10 seconds after the beginning of the trial with both an aversive tone (440 Hz, 85 dB) and the lights (100 lux) switched on. The mice were trained to locate the target hole according to surrounding visual cues and escape from the aversive tone for three training trials per day over 3 consecutive days. The spatial memory was measured by the "probe test". All of the training trials and the probe trials were videotaped for 3 minutes. Then, the escape latency for the training trials and the percentage of time in different quadrants (target, left, right, and opposite) during the probe test were analyzed. In the probe test, the tannic acid (30 mg/kg) group displayed a significant preference to the target zone whereas the other groups did not, as illustrated in FIG. 8.

The basic metabolism, behavior functioning, and cognitive behaviors characteristics of mice treated with tannic acids with multiple injections at various doses were studied in the experiments described in Example 2. In summary, three main findings were noted.

First, the body weight of mice in the tannic acid (30 mg/kg) group decreased. This group of mice also displayed lower spontaneous locomotion in the open field. The open field tasks were used to test novelty-induced locomotor activity and general motor functions (Powell et al., *Biol Psychiatry*, 59(12):1198-1207 [2006]; van den Buuse, Schizophr Bull, 36(2):246-270 [2010]). Without being bound by theory, the decreased locomotion activity in mice with repeated tannic acid injections may be resulted from the faster habituation to the novel environment.

Second, the anxiety—like behaviors of mice treated with tannic acid were decreased in the elevated plus maze. The elevated plus maze task is a mouse model for putative anxiolytic or anxiogenic compounds screening (Rodgers et al., *Braz J Med Biol Res*, 30(3):289-304 [1997]; Steimer, *Dialogues Clin Neurosci*, 13(4):495-506 [2011]). The increase in the proportion of time spent in open arms represents lower anxiety in the plus maze. In the experiment, mice with repeated injections displayed not only higher proportion of time spent in open arms but also higher proportion of travel distance in open arms and lower risk assessment. These results support that repeated injections of tannic acid reduced the anxiety-like behaviors in the elevated plus maze.

Third, mice with repeated tannic acid injections displayed the enhancement of spatial memory retrieval in the Barnes maze. The Barnes maze is a task to evaluate the cognitive function in mice, especially the spatial learning and memory (Rosenfeld et al., *J Vis Exp*, (84):e51194 [2014]). Based on the advancement of the understanding of specific cognitive functional domains, an increasing amount of clinical research emphasizes the impact of cognitive deficits in many mental illnesses including schizophrenia, dementia, Alzheimer's disease, depression, and obsessive compulsive disorder (OCD) etc. (Kirova et al., *Biomed Res Int*, 748212 [2015]; Lai et al., *Curr Pharm Des*, 20(32):5139-5150 [2014]; Okasha et al., *Acta Psychiatr Scand*, 101(4):281-285 [2000]; Rosenblat et al., *Int J Neuropsychopharmacol*, pii: pyv082 [2015]; Terry et al., *Ann Neurol*, 30(4):572-580 [1991]). In the probe test (memory retrieval phase), the tannic acid (30 group) displayed preference to the target zone. This evidence indicated that repeated injections of a high dose tannic acid were capable of enhancing the cognitive function in normal mice. Furthermore, NMDA receptor signaling is considered as an important role in the learning process and memory consolidation (Newcomer et al., *Hippocampus*, 11(5):529-542 [2001]; Rezvani, *Animal Models of Cognitive Impairment*, 1(4) [2006]). Therefore, repeated injections of tannic acid may enhance the cognitive function through NMDA signaling in mice.

Thus, the results of this study indicate that tannic acids would be effective in weight reduction and improving basic behavioral functioning, hyperactivity, anxiety, memory and/or cognitive behavior. For example, a large percentage of children with ADHD have co-morbid learning disorder that can also be improved by tannic acid, given its effects on learning and memory.

Figure 9:
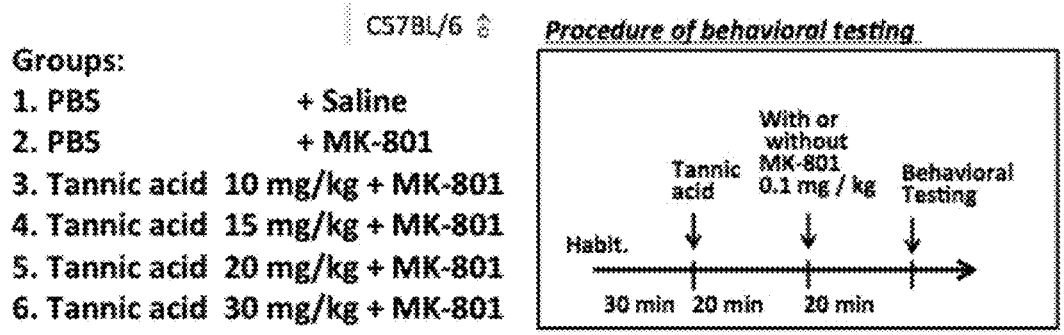
FIG. 9 is a schematic illustration of an exemplary experimental design for verifying the effects of tannic acids in mice treating with MK-801 as described in Example 3. The spontaneous locomotion activity and sensorimotor function of each mouse treated either with tannic acids or vehicle control were tested by open field and prepulse inhibition, respectively, with at least 1-week interval between tests. 20 minutes prior to the MK-801 (or vehicle) administration, tannic acids (or the vehicle) were administrated to each mouse. Also, 20 minutes prior to the behavioral tests, the MK-801 (or the vehicle) was administrated to each mouse.

Example 3. Rescue and Protective Effects of Tannic Acid Injection on MK-801-Treated Mice The objective of this experiment was to assess the potential mechanisms of action of tannic acids in treating CNS disorders, using MK-801, a well-known NMDA receptor antagonist. Tannic acids and MK-801 were administered in mice by intraperitoneal (i.p.) injections before the behavioral tests (i.e., open field and prepulse inhibition), respectively.
Experimental Design This experiment was designed to characterize the mechanism of action of tannic acid. MK-801, also known as dizocilpine, is an antagonist of NMDA receptor (Kovacic et al., *Oxid Med Cell Longev*, 3(1):13-22 [2010]). It has been used in many aspects of NMDA hypo-function induced symptoms of central nerve system diseases, including stereotypic behaviors, anhedonia, learning and memory deficits, working memory impairment and sensorimotor function abnormalities (Furuya et al., *Eur J Pharmacol*, 364(2-3):133-140 [1999]; McLamb et al., *Pharmacol Biochem Behav*, 37(1):41-45 [1990]; Vardigan et al., *Pharmacol Biochem Behav*, 95(2):223-229 [2010]; White et al., *Pharmacol Biochem Behav*, 59(3):613-617 [1998]; Wu et al., *Psychopharmacology (Berl)*, 177(3):256-263 [2005]). The objective of these experiments was to assess the effects of tannic acids on mice with hypo-function NMDA receptor. An exemplary experimental design is illustrated in FIG. 9.
Methods and Materials
Animal and Housing Conditions C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 2.5 months of age).
Drug Administration The mice were randomly assigned into six groups:
Group 1: PBS+Saline control;
Group 2: PBS+MK-801;
Group 3: tannic acid (10 mg/kg)+MK-801;
Group 4: tannic acid (15 mg/kg)+MK-801;
Group 5: tannic acid (20 mg/kg)+MK-801; and
Group 6: tannic acid (30 mg/kg)+MK-801.

Figure 10:
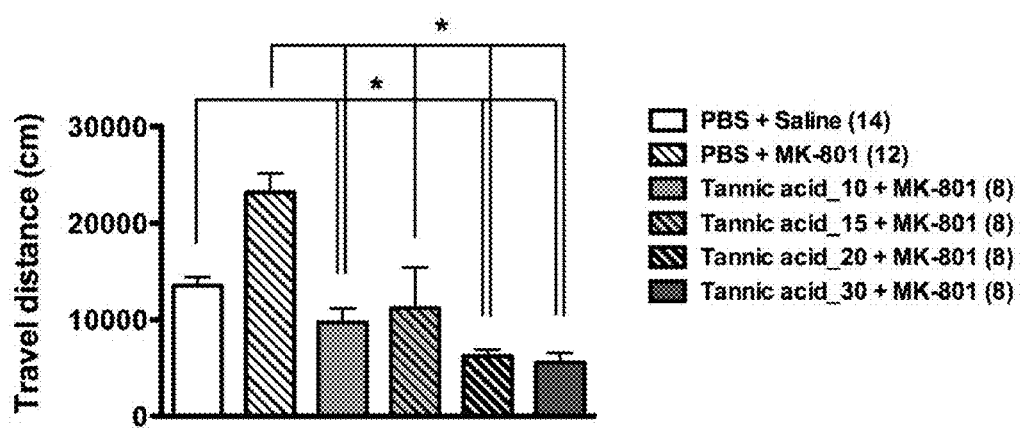
FIG. 10 is a chart showing the effect of tannic acids via a single oral administration in reducing MK-801-induced hyper-locomotion in a dose-dependent manner.

Each mouse in Groups 2-6 received an acute administration of MK-801 (Sigma-Aldrich, USA) dissolved in normal saline, 0.1 mg/kg, i.p.) 20 minutes prior to the behavioral tests. Each mouse in Groups 3-6 received an acute administration of tannic acids (Sigma-Aldrich, USA; dissolved in PBS, 10, 15, 20 or 30 mg/kg, i.p.) 20 minutes prior to the MK-801 administration.
Examination of the Effects of Tannic Acid Administration on MK-801 Treated Mice All mice in this study were tested with open field task and prepulse inhibition task with at least 1-week interval between two tasks. An additional cohort of mice was used to test the effect of different sources of tannic acid on prepulse inhibition.
Results
The Effects of Tannic Acid on Locomotion in MK-801 Treated Mice Compared to the control group (Group 1), the MK-801 group (Group 2) displayed a hyper-locomotion activity. The tannic acid 10, 20, and 30 groups (Groups 3, 5, and 6) displayed a lower locomotion activity than the control group as illustrated in FIG. 10. In comparison to the MK-801 group (Group 2), all tannic acid groups displayed lower locomotion activity, as shown in FIG. 10.

MK-801 generates hyperactivity which is frequently applied as animal models including, but not limited to schizophrenia, bipolar disorder, attention-deficit hyperactivity disorder, obsessive compulsive disorder, Tourette's syndrome, autism spectrum disorders, Fragile X syndrome, Parkinson's disease, dementia with Lewy bodies, and senile dementia (see Rubia et al., 2010; Sheppard and Bradshaw, 1999; Bent et al., 2014; Powell and Miyakawa, 2006; Nestler and Hyman, 2010; Bubeniková-Valesova et al., 2008; Gobira et al., 2013; Lai et al., 2014; Maio et al., 2014; Sontag et al., 2010; Ding et al., 2014; Walitza et al., 2007; Finestone et al., 1982; Golimstok et al., 2011).

The Effects of Tannic Acids on Prepulse Inhibition in MK-801-Treated Mice-Sensorimotor Function Pre-attentive processes tend to be automatic and rapid, and to operate outside of conscious awareness, whereas deliberate attention processes have limited resources, require more efforts, and operate more slowly. A common measure of pre-attentive process is prepulse inhibition. This paradigm has been commonly examined in mouse models of several CNS disorders, including, but not limited to schizophrenia, major depressive disorder, bipolar disorder, attention deficit disorder, attention-deficit hyperactivity disorder, tic disorder, obsessive compulsive disorder, Tourette's syndrome, blepharospasm, post-traumatic stress disorder, panic disorder, autism spectrum disorder, Asperger's disorder, Alzheimer's disease, mild dementia of Alzheimer, dementia with Lewy bodies, Huntington's disease, personality disorders, nocturnal enuresis, and non-epileptic seizures (see McAlonan et al., 2002; Braff et al., 2001; Giakoumaki et al., 2007; Ueki et al., 2006; Perriol et al., 2005; Ludewig et al., 2002; Castellanos et al., 1996; Cadenhead et al., 2000; Matsuo et al., 2017; Lai et al., 2014; McCool et al., 2003; Arguello & Gogos, 2006) because the deficit manifests in a similar manner to the human symptom.

Prepulse inhibition was used as an index of sensorimotor gating function using SR-LAB startle apparatus (San Diego Instruments, San Diego, Calif., USA). Under 72 dB background noise, each session was composed of 5 minutes accumulation period followed by 64 trials in four blocks. The pulse alone (PA) trial was a 40 ms, 120 dB white noise burst. In the prepulse (pp)+pulse trials, a 20 ms white noise prepulse stimuli of 78 dB (pp6), 82 dB (pp10), and 90 dB (pp18) were presented 100 ms before a 40 ms 120 dB pulse. The non-stimulus (NS) trials presented the background noise only. The initial and the last blocks were composed of six PA trials, respectively. Two middle blocks consisted of PA, pp+pulse, and NS trials. These trials were presented pseudo-randomly and separated by intertribal intervals of 15 seconds on average (varying between 10 to 20 s). The percentage of prepulse inhibition was evaluated by the following formula: % PPI=100×[(PA score)−(pp-P score)]/(PA score), where the PA score was the average of the PA value in the middle blocks. Tannic acid improved the prepulse inhibition as in FIGS. 11&12 and dose-dependently, as demonstrated in FIG. 11.

Figure 11:
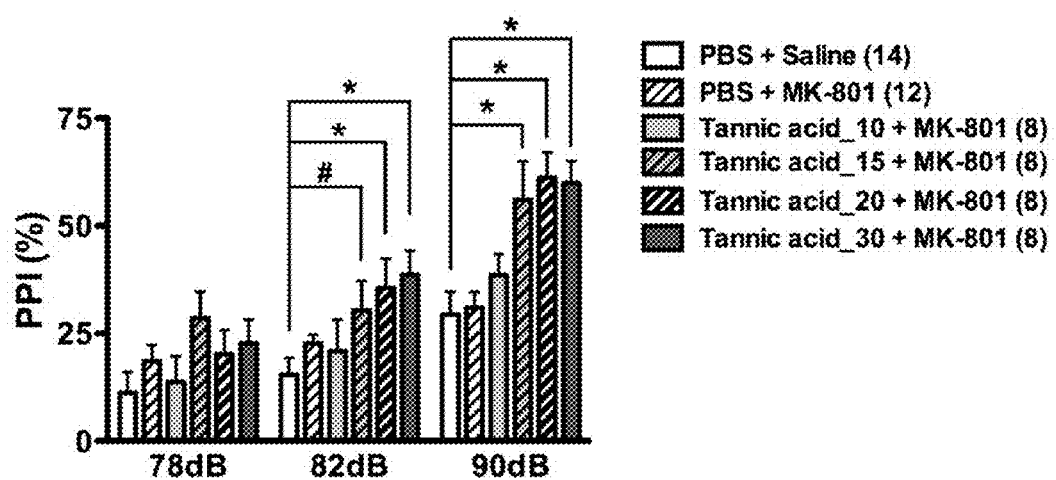
FIG. 11 is a chart showing the effects of tannic acids in improving prepulse inhibition in a dose-dependent manner. The improvement of the prepulse inhibition is better than the controls. 10 mg/kg group shows less improvement of prepulse inhibition than the groups of 15, 20 and 30 mg/kg groups.

In 78 dB prepulse intensity, no significant difference was found among the 6 groups. In 82 dB prepulse intensity, MK-801 and tannic acid (10 mg/kg) groups did not show the difference relative to the control group. As compared to the control group, the tannic acid (15 mg/kg) group displayed a marginally higher percentage of prepulse inhibition, and the tannic acid (20 mg/kg) and tannic acid (30 mg/kg) groups displayed significantly higher percentages of prepulse inhibition. In terms of the 90 dB prepulse intensity, compared to the control group, the tannic acid (15 mg/kg), tannic acid (20 mg/kg) and tannic acid (30 mg/kg) groups displayed significantly higher percentages of prepulse inhibition as compared with the control group, while no such results was observed in the MK-801 and tannic acid (10 mg/kg) groups, as depicted in FIG. 11.

The Effects of Different Tannic Acid Source on Prepulse Inhibition in MK-801-Treated Mice The objective of this experiment was to evaluate the effects of different sources of tannic acids on prepulse inhibition. Tannic acids purchased from Sigma-Aldrich (source A) and from Spectrum, USA (source B) at 15 mg/kg were used in this study. The $IC_{50}$ (μM) of anti-DAAO activities of tannic acids of sources A and B are 0.291 and 0.636, respectively.

Figure 12:
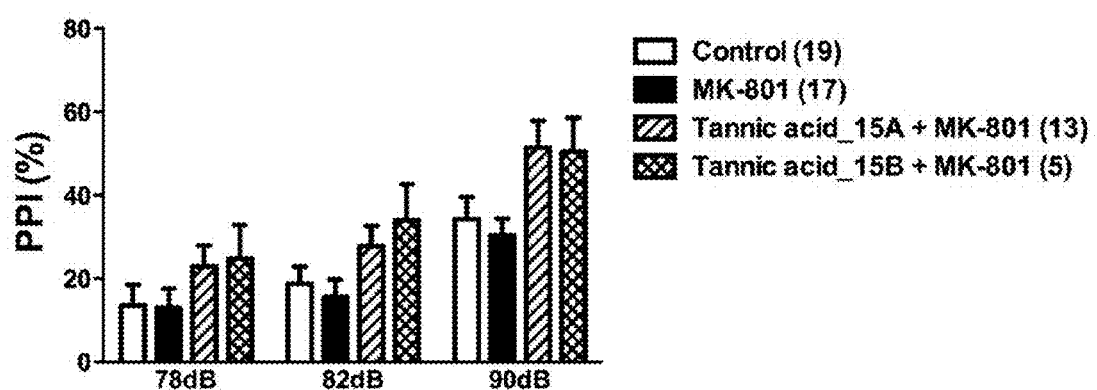
FIG. 12 is a chart showing the improving effects of tannic acids from different sources on prepulse inhibition. Tannic acid is from Sigma-Aldrich (source A) or Spectrum, USA (source B). The improvement of the prepulse inhibition is better than the controls.

With respect to the 78 dB and 82 dB prepulse intensities, no significant difference was observed between the mice treated with tannic acids of the two sources and the control group or the MK-801 group. In terms of the 90 dB prepulse intensity, both tannic acid groups displayed significantly higher percentages of prepulse inhibition as compared with the control group whereas no such results were observed in the MK-801 group. The results obtained from the mice treated with source A (Sigma-Aldrich) tannic acids and source B (Spectrum, USA) tannic acids were similar, as shown in FIG. 12.

Though psychosis symptoms are challenging to observe and measure in animal models, the psychosis-related behaviors can be tested include psychomotor agitation, excitement symptoms, sensory gating and sensitivity to psychotomimetic drugs, such as MK-801 (Arguello et al., Neuron, 52(1): 179-196 [2006]; Lai et al., Curr Pharm Des, 20(32): 5139-5150 [2014]). In mice, parameters related to hyper-locomotion activity and alteration of novelty-induced locomotion activity (either impairment of habituation to novelty or increased exploration) in an open field task can be used to measure the psychomotor agitation and excitement symptoms, respectively (Lai et al., Curr Pharm Des, 20(32):5139-5150 [2014]; Powell et al., Biol Psychiatry, 59(12):1198-1207 [2006]; Vardigan et al., Pharmacol Biochem Behav, 95(2):223-229 [2010]). In the present study, the administration of tannic acid, both by i.p. or per os (p.o.) routes, reversed/protected MK-801 induced hyper-locomotion activity in the open field. The result indicated that the tannic acids are a potential therapeutic agent for treating psychosis symptoms (e.g., delusions and hallucinations).

In the prepulse inhibition task, 15 mg/kg of tannic acid was sufficient to enhance the sensorimotor gating function in mice treated with MK-801. In addition, different sources of tannic acid did not affect the enhancement of sensorimotor function in the prepulse inhibition task. Deficits in prepulse inhibition has been commonly considered as a schizophrenic endophenotype in mouse models because the deficit manifests can be identified similarly in humans (Arguello et al., Neuron, 52(1):179-196 [2006]; Geyer et al., Schizophr Bull, 13(4):643-668 [1987]; Lai et al., Curr Pharm Des, 20(32): 5139-5150 [2014]). The deficits of prepulse inhibition were also found in other central nerve system diseases, including autism spectrum disorder (McAlonan et al., Brain, 125(Pt 7):1594-1606 [2002]), obsessive compulsive disorder, Huntington's disease, nocturnal enuresis, attention deficit disorder, Tourette's syndrome, blepharospasm, non-epileptic seizures, post-traumatic stress disorder (Braff et al., Psychopharmacology (Berl), 156(2-3):234-258 [2001]), panic disorder, bipolar disorder, mild dementia of Alzheimer's, dementia with Lewy bodies, and combined attention-deficit hyperactivity disorder and tic disorder (Giakoumaki et al., Biol Psychiatry, 62(12):1418-1422 [2007]; Ludewig et al., Depress Anxiety, 15(2):55-60 [2002]; Perriol et al., J Neurol Neurosurg Psychiatry, 76(1):106-108 [2005]; Ueki et al., Psychiatry Clin Neurosci, 60(1):55-62 [2006]).

As such, tannic acids are a promising therapeutic agent for various CNS disorders. Further, tannic acids reduce both spontaneous and MK-801-induced hyperlocomotion, indicating that tannic acids Tannic acid can serve as a therapeutic agent to improve symptoms of ADHD and its related disorders.

Moreover, it was observed that tannic acids could maintain and/or reduce body weights in mice treated thereby, indicating that tannic acids would be effective in control body weight and/or treating obesity and its disorders including eating disorder, anorexia nervosa, bulimia nervosa, stroke, coronary heart disease, heart attack, congestive heart failure, congenital heart disease, hypertension, non-alcoholic steatohepatitis, insulin resistance, hyperuricemia, hypothyroidism, osteoarthritis, gallstones, infertility (hypogonadism and hyperandrogegism), obesity hypoventilation syndrome, obstructive sleep apnea, chronic obstructed pulmonary disease, and asthma.

Example 4. Rescue and Protective Effects of Tannic Acid Oral Administration on MK-801 Treated Mice The objective of this experiment was to assess the potential mechanisms of action of tannic acids in treating CNS disorders, using MK-801, a well-known NMDA receptor antagonist. Tannic acids and MK-801 were administered in mice by oral gavage (p.o.) and intraperitoneal (i.p.) injections respectively before the behavioral tests (i.e., open field, prepulse inhibition, Barnes maze and sucrose preference), respectively.

Experimental Design

Figure 13:
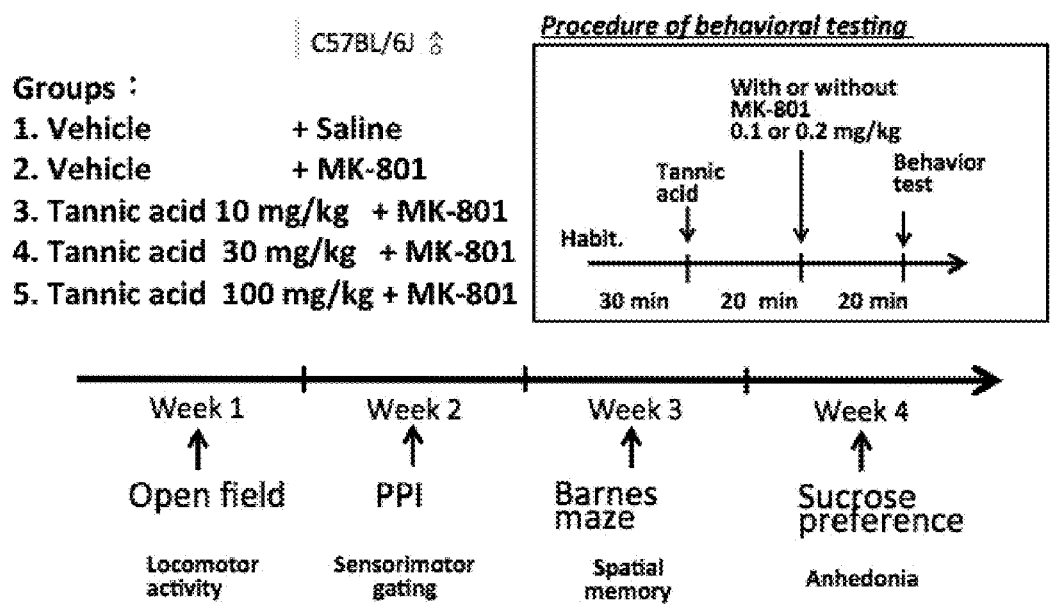
FIG. 13 is a schematic illustration of an exemplary experimental design for verifying the effects of tannic acids in mice treating with MK-801 as described in Example 3. The spontaneous locomotion activity and sensorimotor function of each mouse treated either with tannic acids or vehicle control in addition to MK-801 were tested by open field, prepulse inhibition, Barnes maze, sucrose preference respectively, with at least 1-week interval among tests. 20 minutes prior to the MK-801 (or vehicle) injection, tannic acid (or the vehicle) was administrated to each mouse by i.p. injection. Also, 20 minutes prior to the behavioral tests, the MK-801 (or the vehicle) was administrated to each mouse by i.p. injection.

This experiment was designed to characterize the mechanism of action of tannic acid. MK-801, also known as dizocilpine, is an antagonist of NMDA receptor (Kovacic et al., *Oxid Med Cell Longev*, 3(1):13-22 [2010]). It has been used in many aspects of NMDA hypo-function induced symptoms of central nerve system diseases, including stereotypic behaviors, anhedonia, learning and memory deficits, working memory impairment and sensorimotor function abnormalities (Furuya et al., *Eur f Pharmacol*, 364(2-3):133-140 [1999]; McLamb et al., *Pharmacol Biochem Behav*, 37(1):41-45 [1990]; Vardigan et al., *Pharmacol Biochem Behav*, 95(2):223-229 [2010]; White et al., *Pharmacol Biochem Behav*, 59(3):613-617 [1998]; Wu et al., *Psychopharmacology (Berl)*, 177(3):256-263 [2005]). The objective of these experiments was to assess the effects of tannic acids on mice with hypo-function NMDA receptor. An exemplary experimental design is illustrated in FIG. 13.

Methods and Materials

Animal and Housing Conditions

C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 2.5 months of age).

Drug Administration

The mice were randomly assigned into five groups:
 Group 1: PBS+Saline control;
 Group 2: PBS+MK-801;
 Group 3: tannic acid (10 mg/kg)+MK-801;
 Group 4: tannic acid (30 mg/kg)+MK-801; and
 Group 5: tannic acid (100 mg/kg)+MK-801.

Each mouse in Groups 2-5 received an acute administration of MK-801 (Sigma-Aldrich, USA) dissolved in normal saline, 0.1 mg/kg for open field and Barnes maze tasks, and 0.2 mg/kg for prepulse inhibition and sucrose preference tasks by i.p. injection) 20 minutes prior to the behavioral tests. Each mouse in Groups 3-6 received an acute oral administration of tannic acids (Merck Millipore, Germany; dissolved in PBS, 10, 30, or 100 mg/kg, p.o.) 20 minutes prior to the MK-801 administration.

Results

Examination of the Effects of Tannic Acid Administration on MK-801 Treated Mice

All mice in this study were tested with open field task, prepulse inhibition task, Barnes maze and sucrose preference with at least 1-week interval between tasks.

Figure 14:
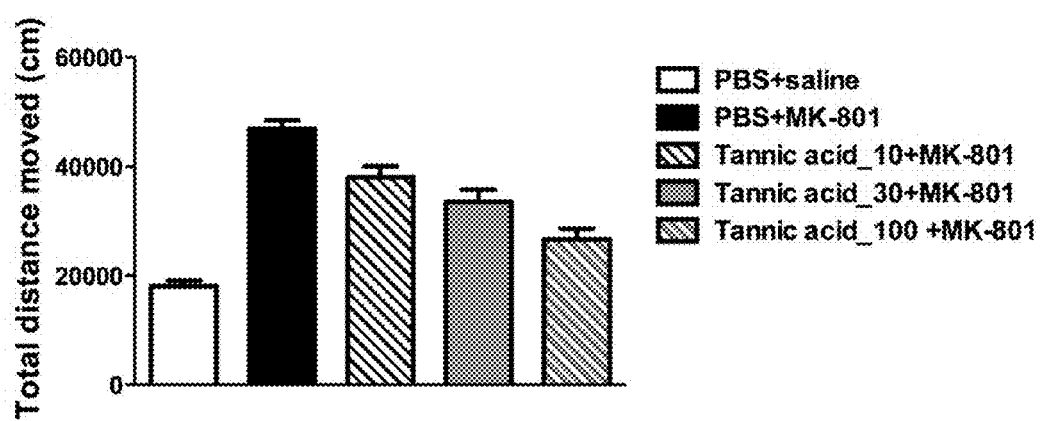
FIG. 14 is a chart showing the effects of tannic acids in improving MK-801-induced hyperactivity in a dose-dependent manner.

The Effects of Tannic Acid Oral Administration on Locomotion in MK-801 Treated Mice In this test, tannic acids were administered orally 20 minutes before the MK-801 (0.1 mg/kg) injection. As shown in FIG. 14, MK-801 induced hyper-locomotion and tannic acids rescued the MK-801-induced hyper-locomotion in a dose-dependent manner.

The Effects of Tannic Acids on Prepulse Inhibition in MK-801-Treated Mice

Figure 15:
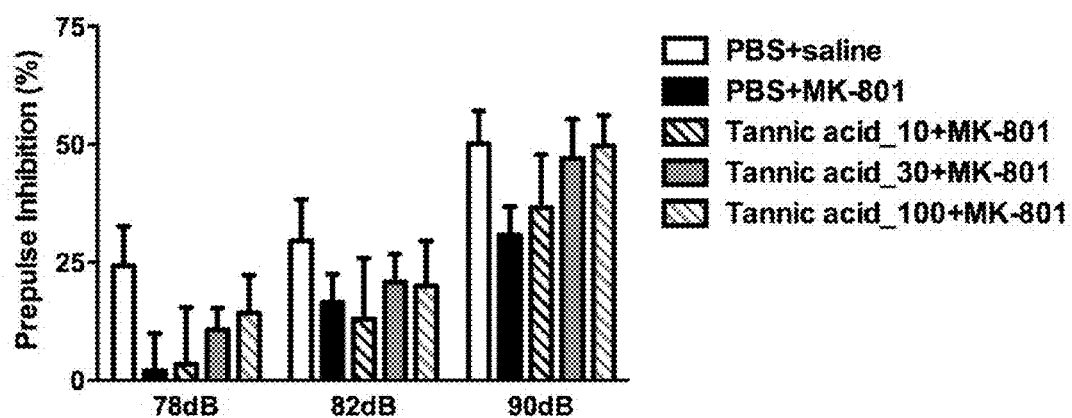
FIG. 15 is a chart showing the effects of tannic acids in improving MK-801-disrupted prepulse inhibition in a dose-dependent manner.

Compare to the control group, MK-801 (0.2 mg/kg) induced robust prepulse inhibition deficits. In 78 dB and 82 dB prepulse intensities, tannic acid (10, 30 and 100 mg/kg) did not rescue/protect the MK-801-induced prepulse inhibition deficits. In terms of the 90 dB prepulse intensity, compared to the MK-801 group, the tannic acid (30 mg/kg), and tannic acid (100 mg/kg) groups displayed significantly rescue/protective effects on MK-801 induced prepulse inhibition deficit. No similar results were observed in the MK-801 and tannic acid (10 mg/kg) groups, as illustrated in FIG. 15.

The Effects of Tannic Acids on Spatial Learning & Memory in MK-801-Treated Mice

Figure 16:
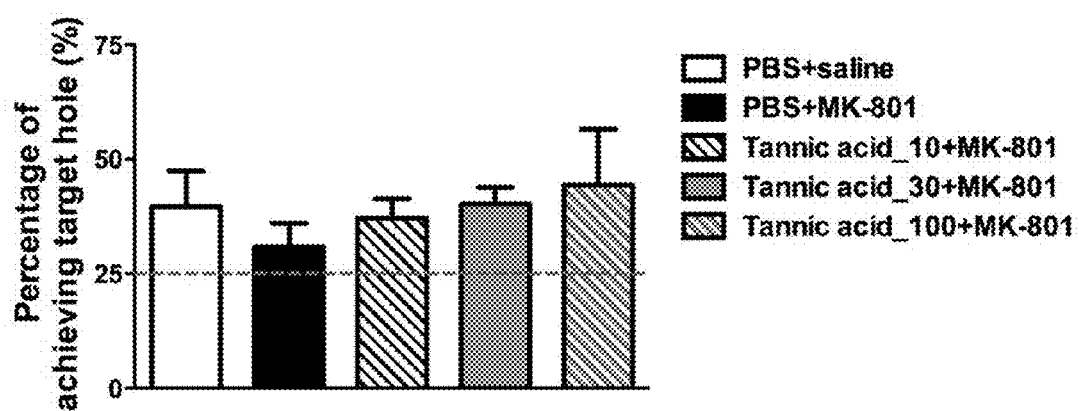
FIG. 16 is a chart showing the effects of tannic acids in improving MK-801-disrupted working memory in a dose-dependent manner in Barnes maze.

Tannic acid dose-dependently improves the memory retrieval of Barnes maze task in the MK-801-treated mice as shown in FIG. 16.

Figure 17:
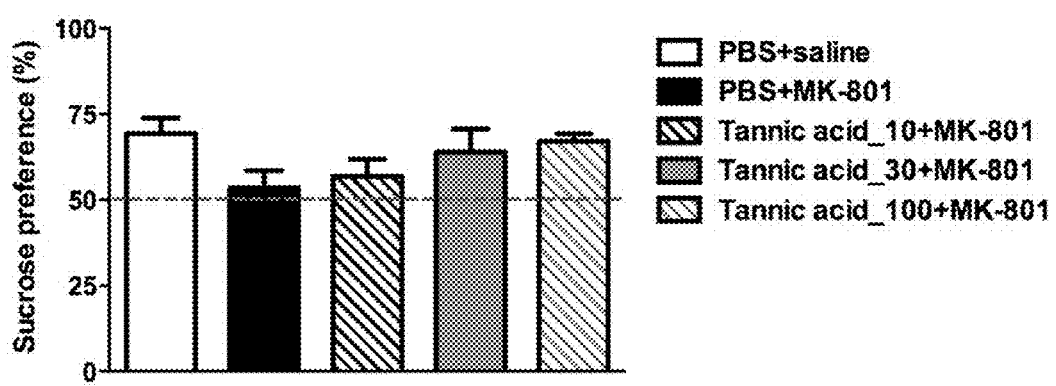
FIG. 17 is a chart showing the effects of tannic acids in improving MK-801-disrupted sucrose preference in a dose-dependent manner
Figure 18:
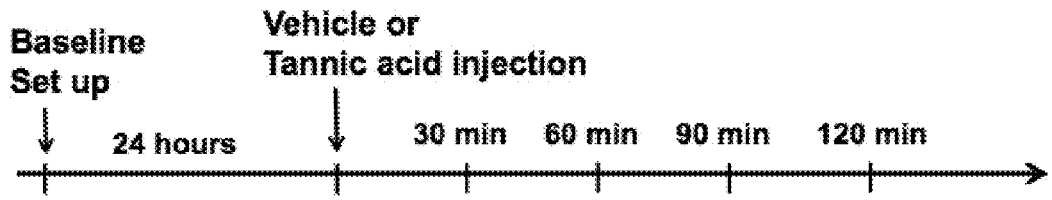
FIG. 18 is a schematic illustration of an exemplary experimental design for verifying the effects of tannic acids in mice on von Frey test. Tannic acids (or the vehicle) were administrated to each mouse by i.p. injection.

The Effects of Tannic Acids on Depressive-Like Behavior (Anhedonia) in MK-801 Treated Mice Compare to the control group, mice in MK-801 group did not show the preference toward the sucrose solution (2%). Compare to the MK-801 group, mice with tannic acid 30 mg/kg and 100 mg/kg displayed rescue/protective effects on MK-801 induced depressive-like behavior (anhedonia) as shown in FIG. 17. Sucrose preference test has been commonly examined in mouse models of several mental illnesses, including, but not limited to, depression, major depression disorder, anhedonia, negative symptoms of schizophrenia, chronic mild and unpredictable stress (see Anderson et al., 2006; Carvalho et al., 2013; Briones et al., 2011; Der-Avakian and Markou, 2012; Tye et al., 2013; Edwards and Koob, 2012; Brigman et al., 2010; Koo and Duman, 2007; Nestler and Hyman, 2010; Overstreet, 2012; Papp et al., 1991; Santiago et al., 2010; Skalisz et al., 2002; Szczypka et al., 2001; Taylor et al., 2010; Vardigan et al., 2010; Willner et al., 1987; You et al., 2011).

Example 5. Analgesic Effects of Tannic Acid in Mice

The objective of this experiment was to assess the analgesic effects of tannic acid in mice. Tannic acids were administrated in mice by intraperitoneal (i.p.) injections before the behavioral tests (i.e., von Frey test).

Experimental Design

Figure 22:
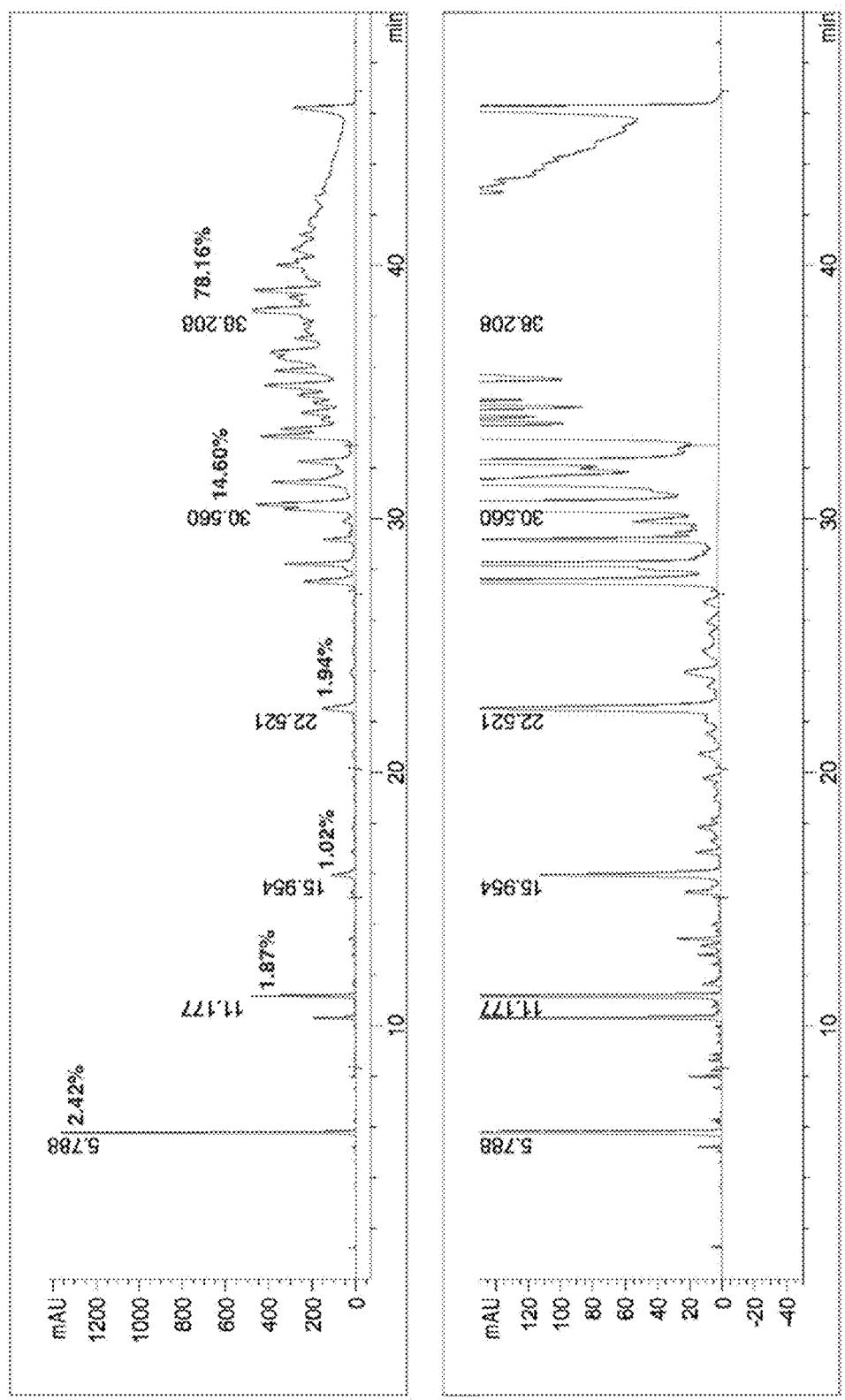
FIG. 22 includes two diagrams showing the HPLC chromatogram of the composition containing tannic acid from *Rhus chinensis*. There are impurities and substantial amount of tannic acids with 1-4 galloyl moieties.

Another cohort was used for von-Frey test (a typical assay for pain sensation). The paw withdrawal thresholds of each mouse were sampled before drug injection and 30, 60, 90 and 120 min after drug injection as shown in FIG. 22.

Methods and Materials
Animal and Housing Conditions

C57BL/6J male mice were group housed (5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 8 weeks of age).

Drug Administration

The mice were randomly assigned into two groups:
Group 1: PBS control; and
Group 2: tannic acid (15 mg/kg)

Each mouse in Groups 1 received an acute administration of PBS as a vehicle control by i.p. injection. Each mouse in Groups 2 received an acute administration of tannic acids (Merck Millipore, Germany; dissolved in PBS 15 mg/kg, i.p.).

Results

The Analgesic Effects of Tannic Acid Injection in Mice

Figure 19:
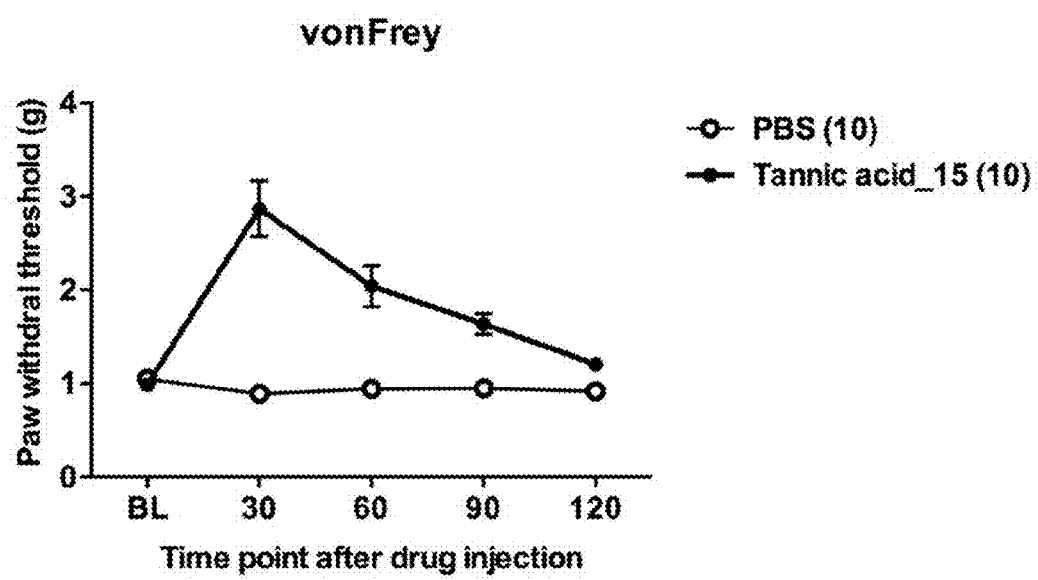
FIG. 19 is a chart showing the improvement of paw withdrawal pain threshold over time after injection of tannic acids or vehicle control (PBS). Tannic acid treatment much improves the pain threshold.

At baseline, no difference was found between groups. Compare to the PBS control, the threshold of Group 2 was significantly higher at 30 min, 60 min and 90 min after drug injection as shown in FIG. 19. The von Frey test has been commonly examined in mouse models of several CNS disorders, including, but not limited to, neuropathic pain including hyperalgesia and allodynia, hypoesthesia in diabetic polyneuropathy, chronic pain syndromes (see Park et al., 2015; Savage and Ma, 2015; Caterha et al., 2000; Nicotra et al., 2014; Keizer et al., 2007; Chakrabarty et al., 2011; Obrosova et al., 2007; Orita et al., 2011; Reeve et al., 2000).

Example 6. Comparisons of Different Tannic Acid Compositions

The compositions and inhibitory activities against D-amino acid oxidase (DAAO) of 3 commercial tannic acids from different suppliers were compared.

Experimental Design

The compositions of 3 commercial tannic acids were determined by HPLC and the inhibitory activities against D-AAO were determined by the method illustrated in Example 1.

Methods and Materials
HPLC Conditions
Instrument: Agilent 1260 Column: Atlantis T3 150*4.6 mm, 30 μm
Mobile phase A: Water+0.1% Trifluoroacetic acid
Mobile Phase B: Methanol: Acetonitrile 2:8 (v/v)
Column temperature: 25° C.
Detector: DAD 280 nm
Flow rate: 1.5 mL/min
Sample preparation: 10 mg/mL
Injection volume: 10 μL
Diluent: water
Gradient:

| Time (mm) | 0 | 10 | 25 | 26 | 34 | 36 | 40 |
|---|---|---|---|---|---|---|---|
| A % | 100 | 81 | 78 | 75 | 73 | 5 | 5 |
| B % | 0 | 19 | 22 | 25 | 27 | 95 | 95 |

Figure 20:
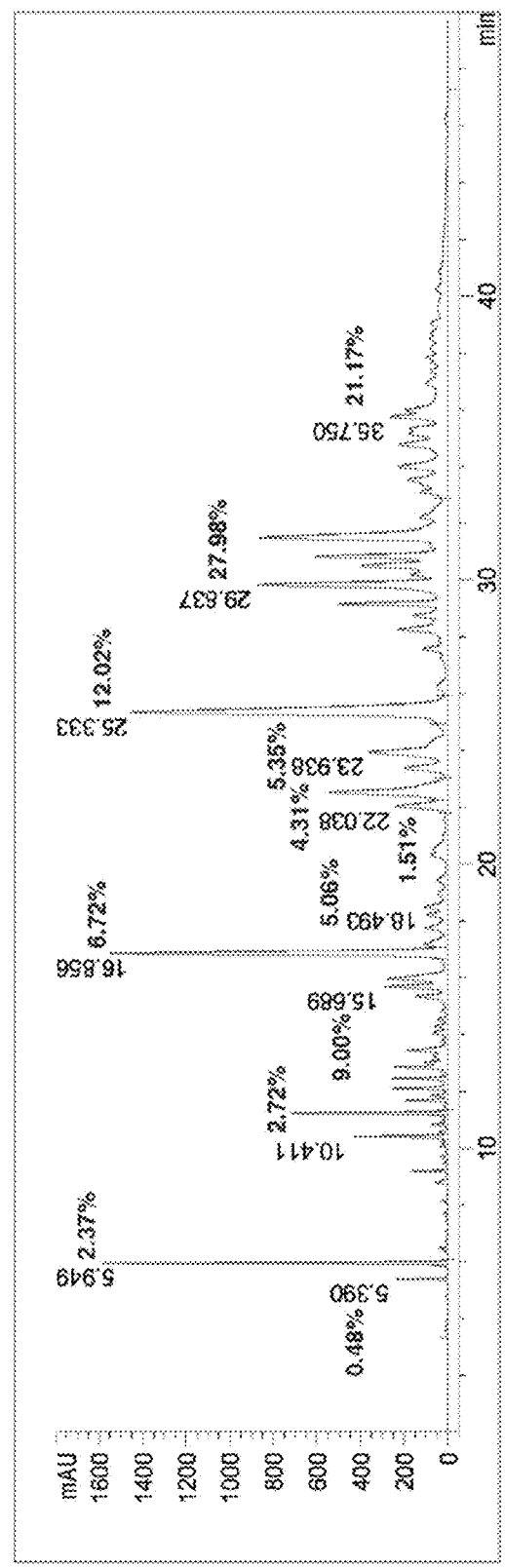
FIG. 20 is a diagram showing the HPLC chromatogram of the composition containing tannic acid from *Quercus infectoria*. There are impurities and substantial amount of tannic acids with 1-4 galloyl moieties.
Figure 21:
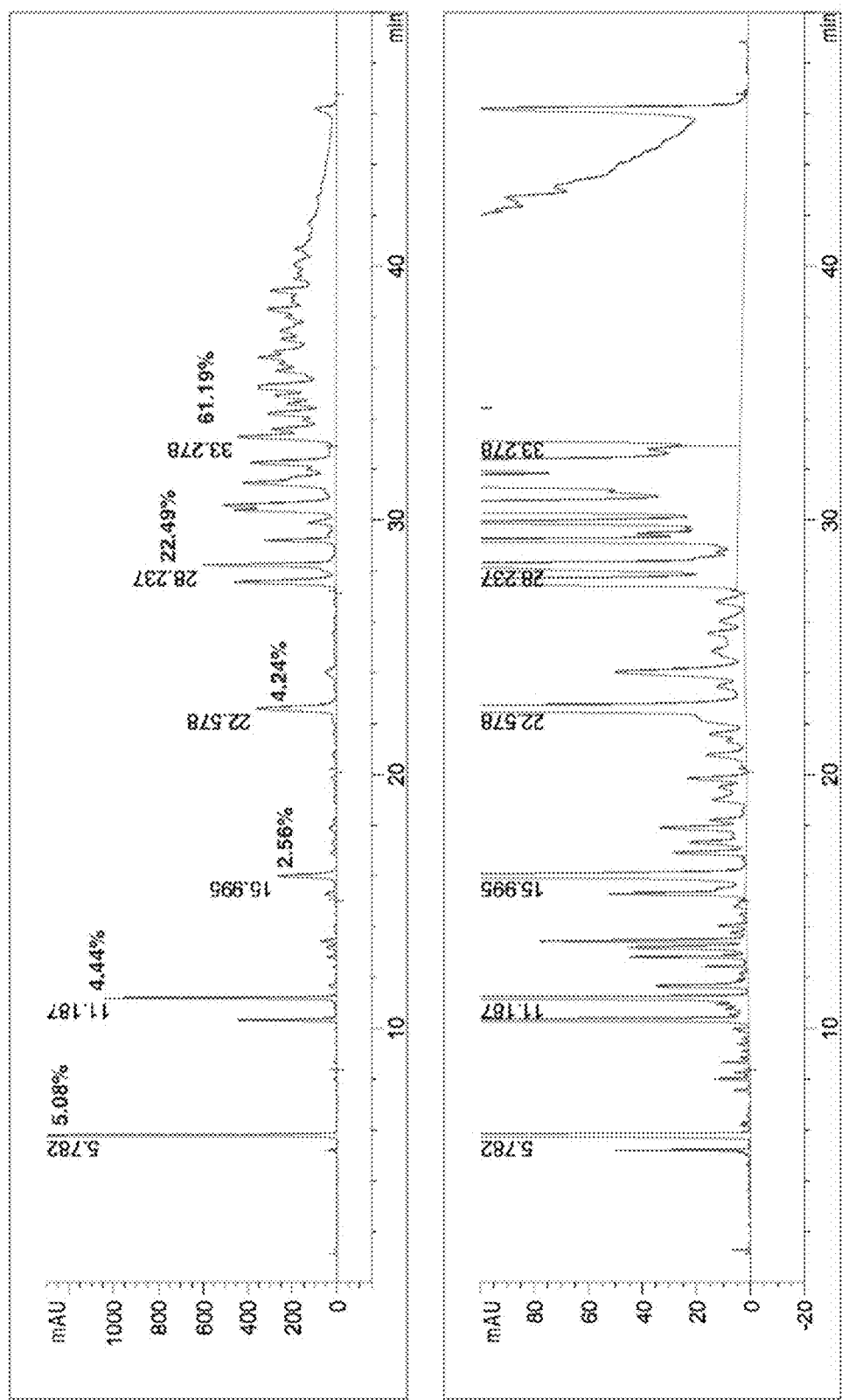
FIG. 21 includes two diagrams showing the HPLC chromatogram of the composition containing tannic acid from *Rhus chinensis*. There are impurities and substantial amount of tannic acids with 1-4 galloyl moieties.

Results
Compositions:

The HPLC chromatograms of 3 tannic acids from different plant or botanic sources are illustrated in FIGS. 20-22.

Inhibitory Activities Against DAAO:

The inhibitory activities of 3 commercial tannic acids against DAAO and their compositions are illustrated in Table 6.

TABLE 6

Inhibitory activities of 3 commercial tannic acids from different plant or botanic sources

| Plant or botanic source | Quercus infectoria | Rhus chinensis | Rhus chinensis |
|---|---|---|---|
| Supplier | Supplier #1 | Supplier #2 | Supplier #3 |
| $IC_{50}$ (μg/ml) | 0.601 | 0.424 | 0.336 |
| $IC_{50}$ Std. Error | 0.007 | 0.005 | 0.006 |
| 2-5G % | 50.86% | 16.32% | 7.25% |
| 6-12G % | 49.14% | 83.68% | 92.76% |
| 8-12G % | 21.17% | 61.19% | 78.16% |

Tannic acids extractted from *Rhus chinensis* have much higher percentage of 6-12 G and much lower 2-5 G percentage than tannic acids from *Quercus infectoria*, and therefore higher DAAO inhibitory potency than the other two.

Example 7. Extraction of Tannic Acid from Gallnuts of Different Plant or Botanic Sources for Comparison Tannic acids were extracted from gallnuts of different plant or botanic sources as indicated and their inhibitory activity against D-amino acid oxidase (DAAO) was investigated.

Methods
Gallnut Grinding Method

Tannic acid producing gallnuts from a suitable plant or botanic source (see Table 6 below) were milled by a mechanical grinder and passed through a 40-mesh sieve to produce fine gallnut powder.

Fine Gallnut Powder Extraction Method

The fine gallnut powder (20.0 g) was placed in 200.0 mL of a suitable solvent (e.g., acetone, acetonitrile, methyl ethyl ketone (MEK), ethyl acetate (EtOAc), ethanol (EtOH), isopropanol, tetrahydrofuran, or 1,4-dioxane). The mixture thus formed was stirred at either RT or 40° C. overnight. The resultant solution was filtered, and the filtrate was concentrated in vacuum to generate a composition containing tannic acids.

Figure 23:
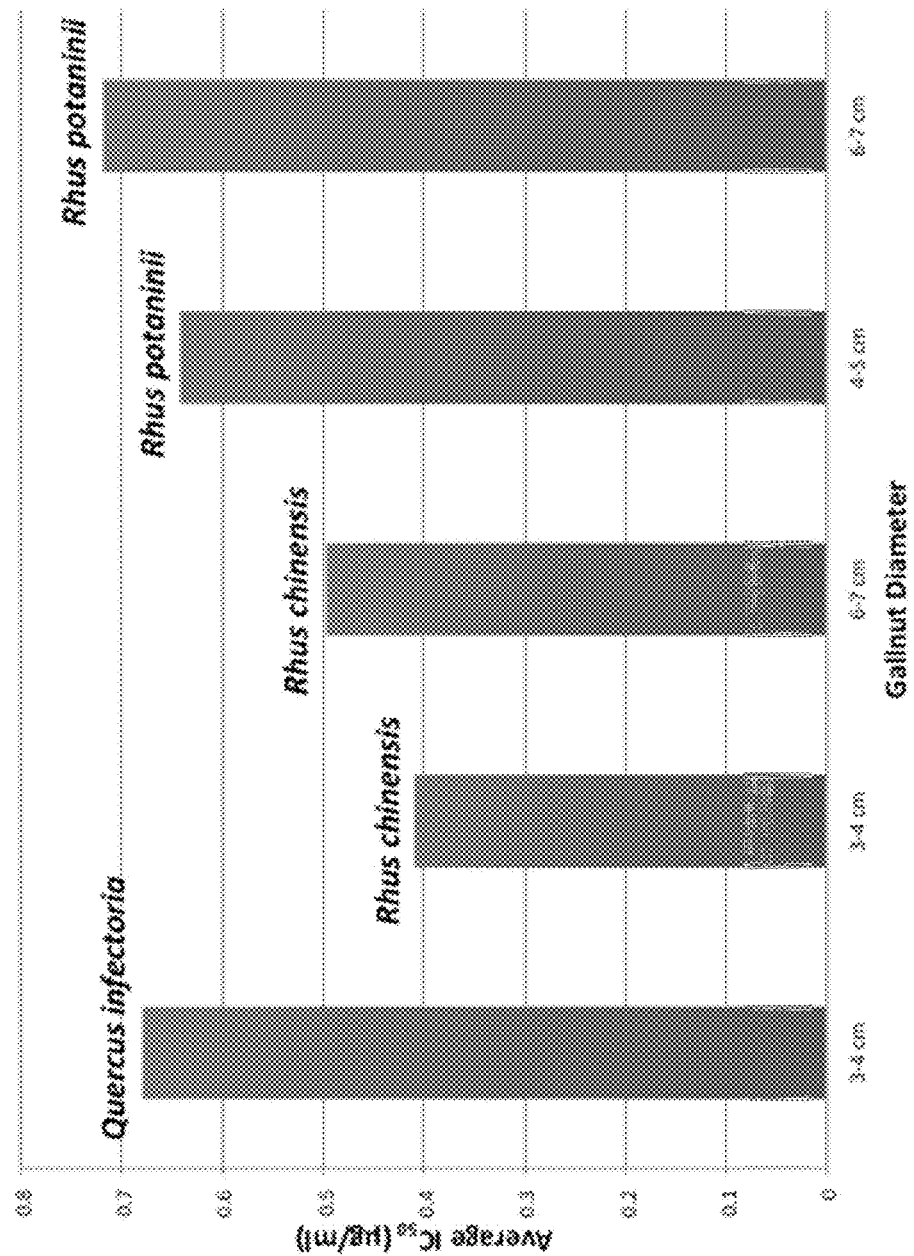
FIG. 23 is a diagram showing the inhibitory activities against DAAO of tannic acids extracted from gallnuts from various plant or botanic sources as indicated. Tannic acids extract from gallnut of *Rhus chinensis* have higher inhibitory activity than from *Rhus potaninii* or *Quercus infectoria*, and 3-4 cm diameter gallnut of *Rhus chinensis* have higher inhibitory activity than the 6-7 cm diameter ones.

Results
Inhibitory Activities Against DAAO:

The inhibitory activities of the tannic acids extracted from gallnuts of different plant or botanic sources against DAAO, following the above method, are illustrated in Table 7. The comparison of gallnuts of various diameters and their DAAO $IC_{50}$'s is illustrated in FIG. 23.

TABLE 7

Inhibitory activities of tannic acids extracted from
gallnuts of different plant or botanic sources

| Plant or botanic source | Quercus infectoria | Rhus chinensis | Rhus chinensis | Rhus potaninii | Rhus potaninii |
|---|---|---|---|---|---|
| Gallnut shape | Spiky ball-shape | horned-shape | horned-shape | belly-shape | belly-shape |
| Gallnut Diameter | 3-4 cm | 3-4 cm | 6-7 cm | 4-5 cm | 6-7 cm |
| Extraction Solvent | MEK | MEK | MEK | MEK | MEK |
| Extraction Temp. | RT | RT | RT | RT | RT |
| $IC_{50}$ (µg/ml) | 0.679 | 0.393-0.424 | 0.441-0.553 | 0.560-0.724 | 0.718 |

As illustrated in Table 6 and FIG. 23, either gallnuts from *Rhus chinensis* or *Rhus potaninii* have lower $IC_{50}$'s against DAAO (stronger inhibition) than those from *Quercus infectoria*. Moreover, smaller gallnuts from *Rhus chinensis* (diameters of 3-4 cm) and *Rhus potaninii* (diameters of 4-5 cm) have lower $IC_{50}$'s as compared to the larger (diameters of 6-7 cm) gallnuts from the same plant or botanic sources.

Example 8. Enrichment Methods of Tannic Acid Extracted from Gallnuts of Different Plant or Botanic Sources Tannic acids extracted from gallnuts of each plant or botanic source noted herein were enriched as described below. Their inhibitory activities against DAAO were investigated.

Enrichment Method 1

The fine gallnut powder (20.0 g) was placed in 200.0 mL of a suitable solvent (acetone, methyl ethyl ketone, ethyl acetate, or ethanol) and the mixture thus formed was stirred at either RT or 20-60° C. for 12 hrs. The resultant solution was filtered, and the filtrate was concentrated in vacuum to form a composition containing tannic acids. The composition was mixed with 50.0 mL of 50 or 30% methyl ethyl ketone/hexane solution (50% or 30% methyl ethyl ketone in hexane). The mixture thus formed was further stirred at RT for 12 hrs, and the resulting two organic layers were separated. The oilier layer (the lower layer) was concentrated in vacuum to produce a crude solid. The solid was dissolved in 50.0 mL of a suitable solvent (acetone, methyl ethyl ketone, ethyl acetate, methyl acetate, or ethanol), and the resulting solution was mixed with charcoal (1.6 g). The resulting mixture was stirred at RT for 12 hrs and $CaSO_4$ or $MgSO_4$ (2.5 g) was added into the mixture. The mixture thus formed was further stirred at RT for 30 min and filtered through a bed of Celite, washed with a suitable solvent (acetone, methyl ethyl ketone, ethyl acetate, methyl acetate, or ethanol) (100 mL×2), and concentrated in vacuum. The resultant solid (containing tannic acids) was dissolved in acetone or ethyl acetate (12.0 mL), and then the solution thus formed was stirred and mixed with $CH_2Cl_2$ (72.0 mL) dropwise. The solid thus formed was collected by filtration and dried under vacuum at 40° C. for 2 hrs to produce an enriched tannic acid solid.

Enrichment Method 2

The fine gallnut power (20.0 g) was placed in 200.0 mL of a suitable solvent (acetone, methyl ethyl ketone, ethyl acetate, methyl acetate, ethanol) was stirred at RT for 12 hrs. The solution thus formed was filtered, and the filtrate collected was mixed with 200.0 mL of hexane. The mixture was stirred at RT for 12 hrs, and the resulting two organic layers were separated. The oiler layer (lower layer) was concentrated in vacuum and the solid thus obtained was dissolved in 50.0 mL of a suitable solvent (acetone, methyl ethyl ketone, ethyl acetate, methyl acetate, ethanol, etc.). The resulting solution was mixed with charcoal (1.6 g) and further stirred at RT for 12 hrs. The mixture thus obtained was further mixed with $CaSO_4$ or $MgSO_4$ (2.5 g) and stirred at RT for 30 min. The mixture was filtered through a bed of Celite, washed with (acetone, methyl ethyl ketone, ethyl acetate, methyl acetate, ethanol, etc.) (100 mL×2), and concentrated in vacuum. The crude residues thus obtained were dissolved in acetone or ethyl acetate (12.0 mL), and the solution thus formed was stirred and mixed with $CH_2Cl_2$ (72.0 mL) slowly. The solid thus formed was collected by filtration and dried under vacuum at 40° C. for 2 hrs to produce an enriched tannic acid composition.

Enrichment Method 3

The fine gallnut power (20.0 g) was placed in 200.0 mL of solvent (acetone, methyl ethyl ketone, ethyl acetate, methyl acetate, or ethanol) was stirred at RT for 12 hrs. The resultant solution was filtered, and the filtrate was collected. The filtrate was then added into 200.0 mL hexane. The mixture thus formed was stirred at RT for 12 hrs, and the resulting two organic layers were separated. The oilier layer (lower layer) was collected and mixed with 40.0 mL of solvent (acetone, methyl ethyl ketone, ethyl acetate, methyl acetate, or ethanol) and charcoal (1.6 g) and the resulting mixture was stirred at RT for 12 hrs. The mixture was further mixed with $CaSO_4$ or $MgSO_4$ (2.5 g) and stirred at RT for 30 min, filtered through a bed of Celite, and washed with solvent (acetone, methyl ethyl ketone, ethyl acetate, methyl acetate, or ethanol) (100 mL×2). The filtrate thus collected was concentrated in vacuum and the resultant solid substances were dissolved in acetone or ethyl acetate (12.0 mL). The solution thus formed was stirred and mixed with $CH_2Cl_2$ (72.0 mL) dropwise. The solid thus formed was collected by filtration and dried under vacuum at 40° C. for 2 hrs to form an enriched tannic acid composition.

Enrichment Method 4

The fine gallnut power (20.0 g) was placed in 200.0 mL of solvent (acetone, methyl ethyl ketone, ethyl acetate, methyl acetate, or ethanol) to form a mixture, which was stirred at RT for 12 hrs. The mixture was mixed with charcoal (1.6 g) and stirred at RT for 12 hrs. The resultant mixture was further mixed with $CaSO_4$ or $MgSO_4$ (2.5 g) and stirred at RT for 30 min, filtered through a bed of Celite, washed with solvent (acetone, methyl ethyl ketone, ethyl acetate, methyl acetate, or ethanol) (100 mL×2). The filtrate was concentrated in vacuum, the resultant residue was dissolved in acetone or ethyl acetate (12.0 mL), and the solution thus formed was stirred and mixed with $CH_2Cl_2$ (72.0 mL) slowly. The solid thus formed was collected by filtration and dried under vacuum at 40° C. for 2 hrs to produce an enriched tannic acid composition.

Enrichment Method 5

The fine gallnut power (20.0 g) was placed in 200.0 mL of solvent (acetone, methyl ethyl ketone, ethyl acetate, methyl acetate, or ethanol) and the mixture thus formed was stirred RT for 12 hrs. The mixture was mixed with charcoal (1.6 g) and stirred at RT for 12 s hrs. The mixture was further mixed with $CaSO_4$ or $MgSO_4$ (2.5 g) and stirred at RT for 30 min. The mixture was filtered through a bed of Celite, and washed with solvent (acetone, methyl ethyl ketone, ethyl acetate, methyl acetate, or ethanol) (100 mL×2). The filtrate was concentrated down to about 10~15 mL and the resulting solution was mixed with $CH_2Cl_2$ (60~90 mL) dropwise. The solid thus formed was collected by filtration and dried under vacuum at 40° C. for 2 hrs to form an enriched tannic acid composition.

Enrichment Method 6

The fine gallnut power (20.0 g) was placed in 200.0 mL of solvent (acetone, methyl ethyl ketone, ethyl acetate, methyl acetate, or ethanol) and the solution thus formed was stirred at RT for 12 hrs, and then filtered. The filtrate was collected and mixed with charcoal (1.6 g) and stirred at RT for 12 hrs. The mixture was further mixed with $CaSO_4$ or $MgSO_4$ (2.5 g) and stirred at RT for 30 min. The resulting mixture was then filtered through a bed Celite, washed with solvent (acetone, methyl ethyl ketone, ethyl acetate, methyl acetate, or ethanol) (100 mL×2), and the combined filtrates were concentrated by vacuum evaporation. The crude solid thus formed was dissolved in acetone or ethyl acetate (12.0 mL), and the solution was stirred and mixed with $CH_2Cl_2$ (72.0 mL) slowly. The solid thus formed was collected by filtration and dried under vacuum at 40° C. for 2 hrs to give an enriched tannic acid composition.

Enrichment Method 7

The fine gallnut power (20.0 g) was placed in 50.0 mL of 50% or 30% methyl ethyl ketone/hexane and was stirred at RT for 12 hrs. The resultant mixture was filtered and solids were collected. The solids were then mixed with 200.0 mL solvent (acetone, methyl ethyl ketone, ethyl acetate, methyl acetate, or ethanol). The mixture thus formed was stirred at RT for 12 hrs, filtered and the filtrate was collected. The filtrate was then mixed with charcoal (1.6 g) and stirred at RT for 12 hrs. The resulting mixture was further mixed with $CaSO_4$ or $MgSO_4$ (2.5 g) and stirred at RT for 30 min, filtered through a bed of Celite, washed with solvent (acetone, methyl ethyl ketone, ethyl acetate, methyl acetate, or ethanol) (100 mL×2), and the filtrate was concentrated by vacuum evaporation. The residue thus obtained was dissolved in acetone or ethyl acetate (12 mL), and then the solution was stirred and mixed with $CH_2Cl_2$ (72.0 mL) dropwise. The solid thus formed was collected by filtration and dried under vacuum at 40° C. for 2 hrs to produce an enriched tannic acid composition.

Enrichment Method 8

The fine gallnut power (20.0 g) was placed in 50 mL of 50 or 30% methyl ethyl ketone/hexane and was stirred at RT for 12 hrs. The solution was filtered and the solid collected was mixed with 200.0 mL of solvent (acetone, methyl ethyl ketone, ethyl acetate, methyl acetate, or ethanol). The mixture was stirred at RT for 12 hrs and filtered, and the filtrate collected was mixed with charcoal (1.6 g) and stirred at RT for 12 hrs. The resulting mixture was further mixed with $CaSO_4$ or $MgSO_4$ (2.5 g) and stirred at RT for 30 min. The mixture was then filtered through a bed of Celite, washed with solvent (acetone, methyl ethyl ketone, ethyl acetate, methyl acetate, or ethanol) (100 mL×2), and the filtrate was concentrated down about 10~15 mL. The residual solution was mixed with $CH_2Cl_2$ (60~90 mL) slowly and the solid thus formed was collected by filtration and dried under vacuum at 40° C. for 2 hrs to produce an enriched tannic acid composition.

Enrichment Method 9

The fine gallnut power (20.0 g) was placed in 200.0 mL of solvent (acetone, methyl ethyl ketone, ethyl acetate, or ethanol) and was stirred at 20~60° C. for 12 hrs. The solution was filtered and the filtrate collected was placed in 200.0 mL of hexane. The mixture thus formed was stirred at RT for 12 hrs, and the two resulting organic layers were separated. The oiler layer (lower layer) was collected and mixed with 40.0 mL of solvent (acetone, methyl ethyl ketone, ethyl acetate, methyl acetate, or ethanol), and the solution thus formed was mixed with charcoal (1.6 g) and stirred at RT for 12 hrs. The mixture was further mixed with $CaSO_4$ or $MgSO_4$ (2.5 g) and stirred at RT for 30 min. The mixture was then filtered through a bed of Celite, washed with solvent (acetone, methyl ethyl ketone, ethyl acetate, methyl acetate, or ethanol) (100 mL×2), and the filtrate was concentrated under vacuum. The residue thus formed was dissolved in acetone or ethyl acetate (12 mL), and then the solution was stirred and mixed with $CH_2Cl_2$ (72.0 mL) dropwise. The solid thus formed was collected by filtration and dried under vacuum at 40~45° C. for 2 hrs to produce an enriched tannic acid composition.

Enrichment Method 10

Figure 26:
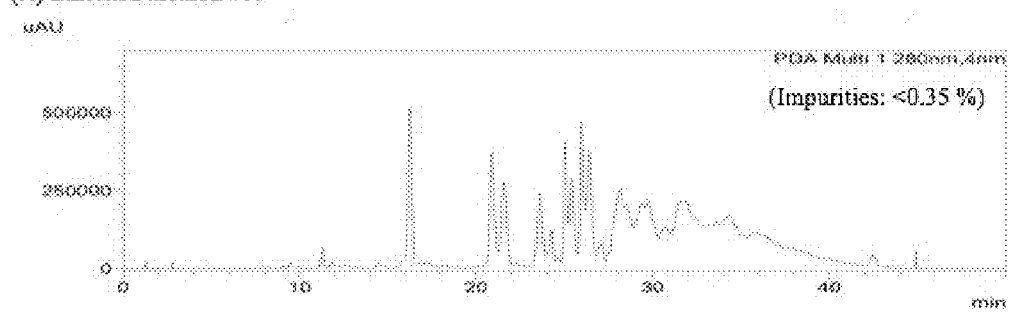
FIG. 26 is the diagram showing the HPLC-MS chromatograms of the compositions of tannic acid from Enrichment Method #10, USP Standard, and Wenzhou Ouhai Fine Chemicals Corporation where that of Enrichment Method #10 contains less than 0.35% of non-tannic acid impurities while those of UPS Standard and Wenzhou Ouhai Fine Chemicals Corporation contain much higher quantities of non-tannic acid impurities, 15.99% and 6.46%, respectively.
Figure 26:
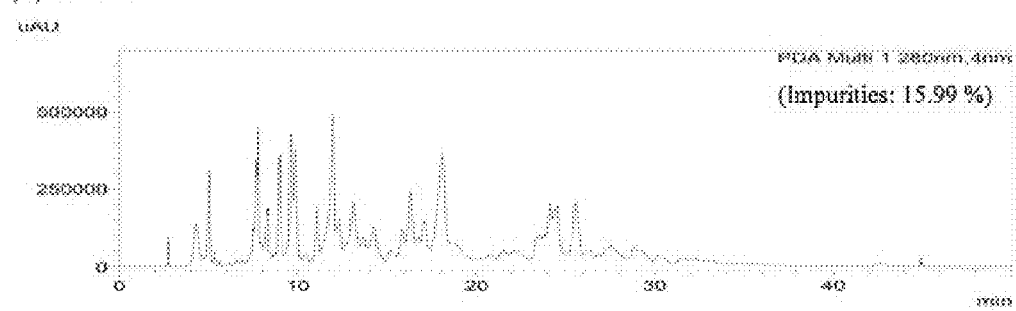
Figure 26:
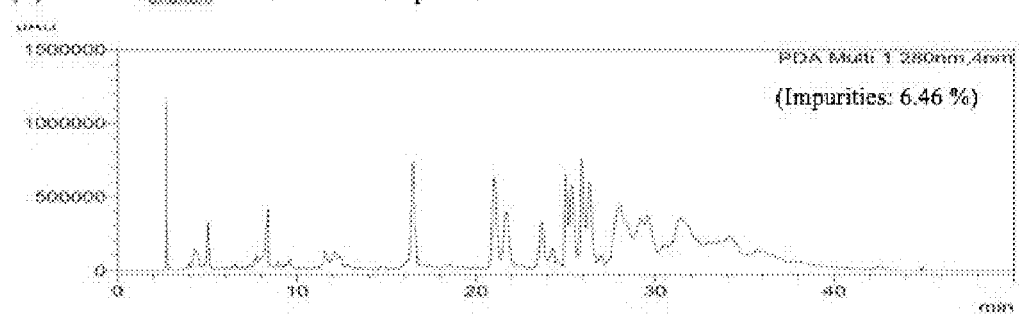

The solution of tannic acid solid (100 g), either from commercial source or crude extract from gallnut powder or small chips, in 250 mL of water was stirred at RT until the all solid was dissolved, then the solution was added with 3.0 g of $K_2CO_{3(s)}$ dissolved in 50 mL of water. The mixture was then extracted with 600 mL of a solvent (including ethyl acetate, methyl acetate, or methyl ethyl ketone) at RT for 1 hr, and this organic layer was separated. The organic layer was further added with 20 g of $MgSO_{4(s)}$ and stirred at RT for 0.5 hr. The mixture was then filtered through a bed of Celite (20 g), washed with a solvent (including ethyl acetate, methyl acetate, or methyl ethyl ketone, 100 mL), and the filtrate was concentrated in vacuo. The resulting residue was diluted with a solvent (including acetone, ethyl acetate, methyl acetate, or methyl ethyl ketone, 110 mL), then 660 ml of another solvent was mixed with the resulting solution at RT and the resulting solution was stirred until the addition was completed. The mixture was stirred at RT for 12~18 hrs. The solid formed was collected by filtration and dried under vacuum at 45° C. for 12 hrs. The composition of tannic acid afforded was analyzed by HPLC-MS (FIG. 26) and $^1$H-NMR. The HPLC-MS chromatogram (FIG. 26) of the composition of tannic acid from Enrichment Method #10 contains less than 0.35% of non-tannic acid impurities, compared to those of UPS Standard and Wenzhou Ouhai Fine Chemicals Corporation containing much higher quantities of non-tannic acid impurities, 15.99% and 6.46%, respectively. The $^1$H-NMR spectrum of the composition of tannic acid from Enrichment Method #10 illustrates only peaks from gallolyl and glucose moieties while those of USP Standard and Wenzhou Ouhai Fine Chemicals Corporation show several peaks other than those from galloyl and glucose moieties. Further HPLC-MS analyses of the compositions of tannic acid from Enrichment Method #10, USP Standard, and Wenzhou Ouhai Fine Chemicals Corporation are illustrated in Table 8. Further $^1$H-NMR analyses of the compositions of tannic acid from Enrichment Method #10, USP Standard, and Wenzhou Ouhai Fine Chemicals Corporation are illustrated in Table 9. It was thus demonstrated that after Enrichment Method #10, the composition of tannic acid showed a much higher purity than those of tannic acid from USP Standard and Wenzhou Ouhai Fine Chemicals Corporation.

TABLE 8

Further HPLC-MS analyses of composition of tannic acid from Enrichment Method #10, USP Standard, and Wenzhou Ouhai Fine Chemicals Corporation

| Different sources of tannic acid | Retention time (min) | LC-MS (negative), base peak m/z | HPLC (UV 280), Area % (>0.10%) | Total area (%) |
|---|---|---|---|---|
| Enriched method #10 (Purity: >99.65%) | 0-9.5 | ND | ND | <0.35 |
| USP Standard (Purity: 84.01%) | 2.74 | 191 | 0.15 | 15.99 |
| | 4.30 | 343 | 2.27 | |
| | 5.05 | 343 | 2.05 | |
| | 5.36 | 687 | 0.25 | |
| | 5.62 | 343 | 0.12 | |
| | 6.10 | 325 | 0.12 | |
| | 6.56 | 325 | 0.14 | |
| | 6.84 | 495 | 0.26 | |
| | 7.52 | 495 | 1.10 | |
| | 7.69 | 991 | 1.89 | |
| | 7.78 | 991 | 1.66 | |
| | 7.93 | 495 | 0.57 | |
| | 8.26 | 643 | 1.29 | |
| | 8.34 | 643 | 0.73 | |
| | 8.50 | 643 | 0.17 | |
| | 8.77 | 477 | 0.49 | |
| | 9.00 | 647 | 2.73 | |
| Wenzhou Ouhai Fine Chemicals Corporation (Purity: 93.54%) | 2.74 | 347 | 0.96 | 6.46 |
| | 4.01 | 337 | 0.18 | |
| | 4.34 | 339 | 1.14 | |
| | 5.07 | 339 | 1.37 | |
| | 7.74 | 643 | 0.43 | |
| | 7.97 | 643 | 0.28 | |
| | 8.37 | 643 | 2.10 | |

TABLE 9

Further $^1$H-NMR (400 MHz, acetone-$d_6$/$D_2O$ (9:1, v/v)) analyses of composition of tannic acid from Enrichment Method #10, USP Standard, and Wenzhou Ouhai Fine Chemicals Corporation

| Different sources of tannic acid | Enriched method #10 | USP standard | Wenzhou Ouhai Fine Chemicals Corporation |
|---|---|---|---|
| Substituent | | $\delta_H$ (H, mult) | |
| Glucose | 4.31-4.32 (1H, m) | 4.31-4.33 (1H, m) | 4.31-4.33 (1H, m) |
| | 4.57 (2H, m) | 4.55-4.56 (2H, m) | 4.58 (2H, m) |
| | 5.60-5.72 (2H, m) | 5.64-5.70 (2H, m) | 5.64-5.70 (2H, m) |
| | 5.98-6.04 (1H, m) | 5.98-6.12 (1H, m) | 6.02-6.07 (1H, m) |
| | 6.26-6.31 (1H, m) | 6.27-6.31 (1H, m) | 6.30-6.36 (1H, m) |
| Galloyl | 6.97-7.60 (15H, m) | 6.98-7.60 (10H, m) | 6.98-7.50 (15H, m) |
| Impurities | N/A | 1.95 | 2.20 |
| | | 2.22-2.38 | 2.62-2.68 |
| | | 2.51-2.55 | 3.71 |
| | | 4.05-4.10 | 4.38 |
| | | 4.15-4.19 | 6.73 |
| | | 4.44 | |
| | | 4.64-4.69 | |
| | | 5.22-5.29 | |
| | | 5.42-5.56 | |
| | | 5.72-5.78 | |
| | | 6.98-7.60 | |

Slurrying Method

The solid afforded from any of the Enrichment Methods described above was slurried with 2000 mL of a solvent (including heptane, $CH_2Cl_2$, or heptane/$CH_2Cl_2$ (1:9 to 9:1)) at 35~60° C. for 8-16 hrs, then the solid formed was filtered and evaporated in vacuo at 60~70° C. for 8 hrs. The solids were then slurry with 2000 mL of a solvent (including heptane, $CH_2Cl_2$ or heptane/$CH_2Cl_2$ (1:9 to 9:1)) at 35~60° C. for 8-16 hr, then the solid was filtered and evaporated in vacuo at 60~70° C. for 8 hrs. The solid was finally further slurried with 2000 mL of a solvent (including heptane, $CH_2Cl_2$ or heptane/$CH_2Cl_2$ (1:9 to 9:1)) at 35~60° C. for 8-16 hrs, then the solid generated was filtered and evaporated in vacuo at 60~70° C. for 8 hrs to give tannic acid solid (yield: 80%).

Enrichment Method 11—Extraction of Gallnuts

Gallnuts were either ground thoroughly to form fine powder or roughly to form small chips first. The solution of gallnut powder or small chips (10.0 g) in 60~100 mL of a solvent (including ethyl acetate, methyl acetate, methyl ethyl ketone, ethanol, or water) was stirred at 35-60° C. for 3 hrs, then the second batch of 10.0 g of gallnut powder or small chips were added to the solution and continued to stir at 35-60° C. for 3 hrs. The third batch of 10.0 g of gallnut powder or small chips were added to the solution followed by stirring at 35-60° C. for 8~14 hrs. After the stirring period ended, the solution was filtered and the filtrate collected was concentrated in vacuo to give the crude tannic acid solid (yield: 54~60%).

It was found that this multiple-batch approach significantly enhanced the yield of crude tannic acid extract. See Table 10 below for comparison results.

TABLE 10

Comparison of Different Extraction Methods

| | One-Batch Approach | Multiple-Batch Approach |
|---|---|---|
| Total Gallnut | 30 g powder | 30 g powder/ 10 g for each batch |

TABLE 10-continued

Comparison of Different Extraction Methods

|  | One-Batch Approach | Multiple-Batch Approach |
|---|---|---|
| Total time | 9 h | 9 h/3 h for each batch |
| Solvent (Ethyl acetate) | 100 mL | 100 mL |
| Temp. | 45° C. | 45° C. |
| Yield | 19% | 37% |

It was also found that using gallnut power and gallnut small chips resulted in similar tannic acid extraction efficiency, as illustrated in Table 11 below.

TABLE 11

Extraction Conditions Using Gallnut Power and Gallnut Chips

| Gallnut | Power | Chips |
|---|---|---|
| Size | ≤420 μm | 0.4~0.7 cm |
| Extraction method | Extracting 10 g gallnut power every 3 h for three times | Extracting 10 g gallnut chips every 3 h for three times |
| Total Gallnut | 30 g | 30 g |
| Extract solvent (Ethyl acetate) | 60 mL | 100 mL |
| Temp. | 45° C. | 45° C. |
| Total time | 14 h | 14 h |
| Yield | 54% | 52% |

Enrichment Method 11—Further Enrichment of Tannic Acid

The solution of crude tannic acid solid from above (80 g) in 700 mL of water was stirred at RT until all solid was dissolved, then the solution was added with the solution of 2.4 g of $K_2CO_{3(s)}$ dissolved in 100 mL of water. The mixture was then extracted with 1600 mL of a solvent (including ethyl acetate, methyl acetate, or methyl ethyl ketone) at RT for 1 hr, and this organic layer was separated. The organic layer was further added with 16 g of $MgSO_{4(s)}$ and further stirred at RT for 0.5 hr. The mixture was then filtered through a bed of Celite (16 g), washed with a solvent (including ethyl acetate, methyl acetate, or methyl ethyl ketone, 80 mL), and the filtrate was concentrated in vacuo. The residue was diluted with a solvent (including acetone, ethyl acetate, methyl acetate, or methyl ethyl ketone, 240 mL), then the solution was added with hexanes (720 mL) and stirred at RT for 2 hrs, and then this organic layer was separated. The resulting oily residue was diluted with a solvent (including acetone, ethyl acetate, methyl acetate, or methyl ethyl ketone, 240 mL), then the solution was added with hexanes (720 mL) and stirred at RT for 2 hrs, and then this organic layer was separated. The resulting oily residue was diluted with a solvent (including acetone, ethyl acetate, methyl acetate, or methyl ethyl ketone, 100 mL), then 660 ml of another solvent was mixed with the resulting solution at RT and stirred until the addition was completed. The mixture was further stirred at RT for 12~18 hrs. The solid formed was collected by filtration and dried under vacuum at 45° C. for 6 hrs. The solid was slurry with 1600 mL of a solvent (including heptane, $CH_2Cl_2$ or heptane/$CH_2Cl_2$ (1:9 to 9:1)) at 35~60° C. for 16 hrs, then the solid was filtered and evaporated in vacuo at 60~70° C. for 8 hrs. The solid was then slurry with 1600 mL of a solvent (including heptane, $CH_2Cl_2$ or heptane/$CH_2Cl_2$ (1:9 to 9:1)) at 35~60° C. for 8-16 hrs, then the solid was filtered and evaporated in vacuo at 60~70° C. for 8 hrs. The solid was further slurried with 1600 mL of a solvent (including heptane, $CH_2Cl_2$ or heptane/$CH_2Cl_2$ (1:9 to 9:1)) at 35~60° C. for 8-16 hrs, then the solid was filtered and evaporated in vacuo at 60~70° C. for 8 hrs to give the desirable tannic acid (yield: 62%).

Table 12 below shows the content of tannic acids in the tannic acid composition prepared by Enrichment method 11 described herein as determined by HPLC. A tannic acid composition prepared by this method is substantially free of small tannic acids (e.g., having <4 galloyl moieties and a substantial portion is large tannic acids (e.g., having >8 galloyl moieties). As disclosed herein, such tannic acid compositions are expected to have superior therapeutic effects.

TABLE 12

Tannic Acids Content in Tannic Acid Composition Prepared by Enrichment Method 11

|  | Retention time (min) | Area | Area (%) |
|---|---|---|---|
| 1G | 2.74 | 159721 | 0.05 |
| 2-3G | 9.62 | 877350 | 0.30 |
| 4G | 11.63 | 4177341 | 1.41 |
| 5G | 16.56 | 17052862 | 5.76 |
| 6-7G | 26.01 | 91742212 | 30.97 |
| 8-12G | 28.17 | 182200691 | 61.51 |
| Total |  | 296210177 | 100 |

A schematic illustration of the preparation process described above is provided in FIG. 27.

Results

Inhibitory Activities Against DAAO:

The inhibitory activities of differently enriched tannic acids extracted from gallnuts of different plant or botanic sources against DAAO are illustrated in Tables 13 and 14.

TABLE 13

Inhibitory activities of enriched tannic acids extracted from gallnuts of different plant or botanic sources-1

|  | Plant or botanic source | | | | | | | |
|---|---|---|---|---|---|---|---|---|
|  | Quercus infectoria | Quercus infectoria | Rhus chinensis | Rhus chinensis | Rhus chinensis | Rhus chinensis | Rhus chinensis | Rhus chinensis |
| Gallnut Diameter | 3-4 cm | 3-4 cm | 4-5 cm | 4-5 cm | 4-5 cm | 4-5 cm | 4-5 cm | 4-5 cm |
| Extraction Solvent | MEK | MEK | MEK | MEK | MEK | MEK | MEK | EtOH |
| Extraction Temp. | RT | RT | RT | RT | RT | RT | RT | RT |
| Enrichment Method | None | 1 | None | 1 | 2 | 3 | 7 | 1 |

TABLE 13-continued

Inhibitory activities of enriched tannic acids extracted from gallnuts of different plant or botanic sources-1

| | Plant or botanic source | | | | | | | |
|---|---|---|---|---|---|---|---|---|
| | Quercus infectoria | Quercus infectoria | Rhus chinensis | Rhus chinensis | Rhus chinensis | Rhus chinensis | Rhus chinensis | Rhus chinensis |
| $IC_{50}$ (μg/ml) | 0.679 | 0.626 | 0.428 | 0.373 | 0.338 | 0.319 | 0.389 | 0.384 |

As shown in Table 13, all enriched tannic acids by any of the preparation methods described herein showed lower $IC_{50}$ values (indicating stronger inhibition) than those without being enriched (direct extraction only and without removal of tannic acids with 1-5 galloyl moieties, no treatment with charcoal and $CaSO_4$ or $MgSO_4$, and/or no further treatment with the second solvent and methylene chloride). Moreover, enrichment methods 2 and 3 provided the enriched tannic acids with the lowest $IC_{50}$'s activities against DAAO, as compared with methods 1 and 7, while enrichment method 3 afforded the enriched tannic acid with a lower $IC_{50}$ value than enrichment method 2. Also shown, the tannic acid from extraction with EtOH followed by enrichment method 1 showed slightly weaker inhibition than that with MEK followed by the same enrichment method.

TABLE 14

Inhibitory activities of enriched tannic acids extracted from gallnuts of different plant or botanic sources - 2

| Plant or botanic source | Rhus chinensis | Rhus chinensis | Rhus chinensis | Rhus chinensis |
|---|---|---|---|---|
| Gallnut Diameter | 4-5 cm | 4-5 cm | 4-5 cm | 4-5 cm |
| Extraction Solvent | MEK | MEK | MEK | EtOAc |
| Extraction Temp. | RT | 40° C. | 40° C. | 40° C. |
| Enrichment Method | None | None | 3 | 3 |
| $IC_{50}$ (μg/ml) | 0.428 | 0.449 | 0.361 | 0.337 |

As illustrated in Table 14, extraction by ethyl acetate (EtOAc) at the extraction temperature of 40° C. followed by enrichment method 3 afforded the enriched tannic acid with a much lower $IC_{50}$ against DAAO than extraction by MEK at room temperature, extraction by MEK at 40° C., and extraction by MEK at 40° C. followed by enrichment method 3, respectively. Furthermore, as shown in Tables 13 and 14, gallnuts from Rhus chinensis with the diameters of no more than 6 cm showed lower $IC_{50}$ values than those of more than 6 cm.

TABLE 15

Inhibitory activities of various tannic acids

| Tannic acid | From Enrichment Method 10 | Merck | Sigma | Wenzhou Ouhai Fine Chemicals |
|---|---|---|---|---|
| Grade | | USP Standard | ACS | Medical |
| DAAO ($IC_{50}$, μM) | 0.227 | 0.534 | 0.291 | 0.257 |
| 1-4G (%) | 1.76 | 25.08 | 8.75 | 11.84 |
| 4-12G (%) | 99.65 | 91.46 | 92.94 | 91.69 |
| 5-12G (%) | 98.24 | 74.92 | 91.26 | 88.16 |
| 6-12G (%) | 92.48 | 51.13 | 88.35 | 82.50 |
| 8-12G (%) | 61.51 | 24.99 | 68.46 | 51.57 |

As shown in Table 15, tannic acid from Enrichment method 10 gave the lowest DAAO $IC_{50}$ with the compositions of lowest amount of 1-4 G and highest amount of 5-12 G as illustrated above.

Residual Solvents:

The residual solvents determined by $^1$H-NMR are illustrated in Table 16.

TABLE 16

Residual solvents from further slurrying method

| | Methods | | | |
|---|---|---|---|---|
| Residual Solvent | no slurry | $1^{st}$ slurry | $2^{nd}$ slurry | $3^{rd}$ slurry |
| Acetone | 4.7% | 1.1% | 0.7% | 0.4% |
| Dichloromethane | 2.5% | 0.3% | 0.0% | 0.0% |

As illustrated above, after three slurrying, the residual solvents, namely, acetone ad dichloromethane, were further reduced.

Example 9. Rescue and Protective Effects of Enrichment #10 Tannic Acid on MK-801 Treated Mice The objective of this experiment was to evaluate of Enrichment #10 tannic acids in treating CNS disorders, using MK-801 model, a well-known NMDA receptor antagonist. Tannic acids and MK-801 were administrated in mice by oral gavage (p.o.) and intraperitoneal (i.p.) injections respectively before the behavioral tests (i.e., open field and prepulse inhibition), respectively.

Methods and Materials

Animal and Housing Conditions

C57BL/6J male mice were group housed (3-5 mice per cage) with food and water available ad libitum in polysulfone ventilated cages (Alternative Design, AR, USA) in the animal rooms. The colony was maintained on a 12/12-hr light/dark cycle at the temperature of 22±2° C. and all behavioral studies will be performed during the dark cycle. All animals used in this study were adult mice (at least 2.5 months of age).

Drug Administration for Locomotion Test

The mice were randomly assigned into five groups:
Group 1: $ddH_2O$+Saline control;
Group 2: $ddH_2O$+MK-801;
Group 3: Merck TA (50 mg/kg)+MK-801;
Group 4: CCBiotech TA (50 mg/kg)+MK-801; and
Group 5: Enrichment #10 (50 mg/kg)+MK-801.

Each mouse in Groups 2-5 received an acute administration of 0.2 mg/kg MK-801 (Sigma-Aldrich, USA) dissolved in normal saline by i.p. injection 20 minutes prior to the locomotion activity test. Each mouse in Groups 3-6 received an acute oral administration of 50 mg/kg tannic acids dissolved in ddH$_2$O by p.o. 20 minutes prior to the MK-801 administration. Tannic acid purchased from Merch Millipore (Merck TA) and from Wufeng Chicheng Biotech (CCBiotech TA), and tannic acid from Enrichment method 10 (Enrichment #10) at 50 mg/kg were used in this study.
Drug Administration for Prepulse Inhibition Test The mice were randomly assigned into four groups:
Group 1: ddH$_2$O+Saline control;
Group 2: ddH$_2$O+MK-801;
Group 3: Enrichment #10 (50 mg/kg)+MK-801; and
Group 4: Enrichment #10 (200 mg/kg)+MK-801.

Each mouse in Groups 2-4 received an acute administration of 0.3 mg/kg MK-801 (Sigma-Aldrich, USA) dissolved in normal saline by i.p. injection 20 minutes prior to the prepulse inhibition test. Each mouse in Groups 3-4 received an acute oral administration of 50 or 200 mg/kg Enrichment #10 tannic acids dissolved in ddH$_2$O by p.o. 20 minutes prior to the MK-801 administration.
Results
The Effects of Enrichment #10 Tannic Acid on Locomotion Activity in MK-801-Treated Mice The open field task is a common measurement of novelty induced exploratory behavior and general activity in both mice and rats. In this study, the mice were placed in a PLEXIGLAS® cage (37.5 cm×21.5 cm×18 cm) under 50-65 lux light intensity. Their spontaneous locomotor activities were measured for 30 minutes using the SMART video tracking system (Panlab, Harvard Apparatus). The travel distance of each mouse was measured as an index of locomotion activity.

Figure 24:
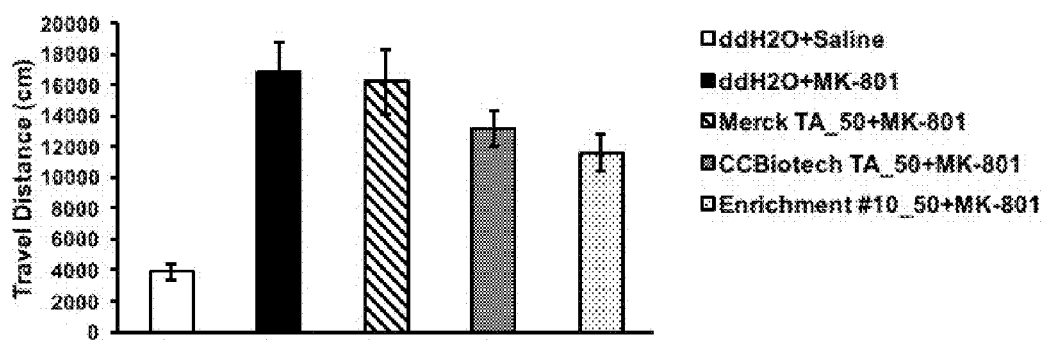
FIG. 24 is a chart showing the effect of tannic acids from different sources, via a single oral administration, in reducing MK-801-induced hyper-locomotion. Tannic acids from Enrichment #10 method have the highest inhibitory activities.
Figure 25:
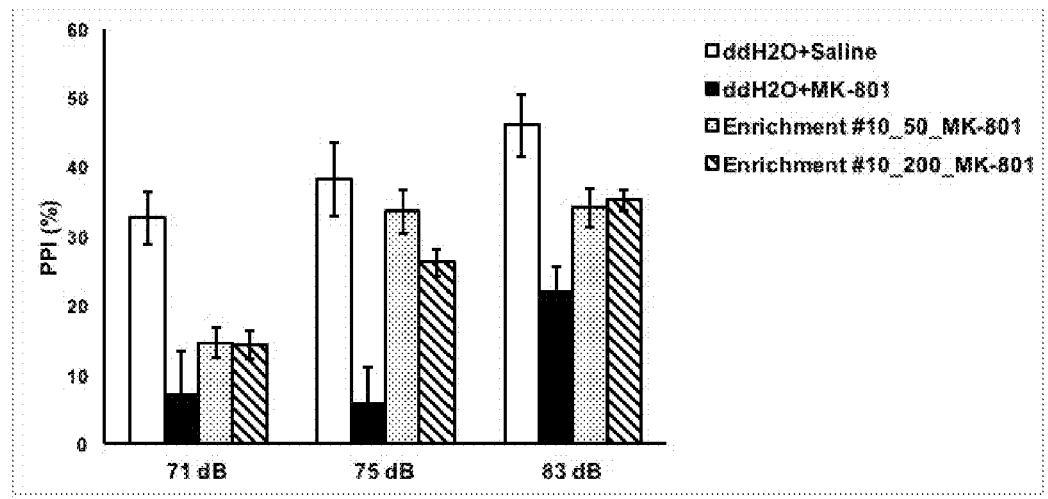
FIG. 25 is a chart showing tannic acids extracted by Enrichment #10 method have high potency, with a ceiling effect that the 50 mg/kg group of animals performed as well as the 200 mg/kg group, in improving MK-801-disrupted prepulse inhibition.

The objective of this experiment was to evaluate the effects of different sources of tannic acids on locomotion activities. Compared to the control group (Group 1), the MK-801 group (Group 2) displayed hyper-locomotion activity. In comparison to the MK-801 group (Group 2), both tannic acid from Wufeng Chicheng Biotech (CCBiotech TA; Group 4) and from Enrichment method 10 (Enrichment #10; Group 5) groups displayed a significant lower locomotion activity whereas tannic acid from Merck Millipore (Merck TA; Group 3) did not. Moreover, Enrichment #10 (Group 5) displayed a lower locomotion activity than CCBiotech TA (Group 4), as shown in FIG. 24.
The Effects of Enrichment #10 Tannic Acid on Prepulse Inhibition in MK-801-Treated Mice Prepulse inhibition was used as an index of sensorimotor gating function using SR-LAB startle apparatus (San Diego Instruments, San Diego, Calif., USA). Under 65 dB background noise, each session was composed of 5 minutes accumulation period followed by 64 trials in four blocks. The pulse alone (PA) trial was a 40 ms, 120 dB white noise burst. In the prepulse (pp)+pulse trials, a 20 ms white noise prepulse stimuli of 71 dB (pp6), 75 dB (pp10), and 83 dB (pp18) were presented 100 ms before a 40 ms 120 dB pulse. The non-stimulus (NS) trials presented the background noise only. The initial and the last blocks were composed of six PA trials, respectively. Two middle blocks consisted of PA, pp+pulse, and NS trials. These trials were presented pseudorandomly and separated by intertribal intervals of 15 seconds on average (varying between 10 to 20 s). The percentage of prepulse inhibition was evaluated by the following formula: % PPI=100×[(PA score)−(pp-P score)]/(PA score), where the PA score was the average of the PA value in the middle blocks Compare to the control group, MK-801 (0.3 mg/kg) induced robust prepulse inhibition deficits in all prepulse intensities. In 71 dB prepulse intensities, tannic acid (50 and 200 mg/kg) did not rescue/protect the MK-801-induced-prepulse inhibition deficits. In terms of the 75 dB and 83 dB prepulse intensity, compared to the MK-801 group, the tannic acid (50 mg/kg), and tannic acid (200 mg/kg) groups displayed significantly rescue/protective effects on MK-801-induced prepulse inhibition deficit. The results obtained from the mice treated with 50 mg/kg and 200 mg/kg Enrichment #10 tannic acids were similar, as illustrated in FIG. 25. It demonstrates a ceiling effect of Enrichment #10 tannic acids at a relative low dose of 50 mg/kg.

Example 10. The Acute Toxicity Study of Tannic Acid from Different Sources

The objective of this example was to evaluate the adverse effects and to determine the maximum tolerated dose (MTD) of tannic acid purchased from Sigma (Sigma tannic acid) and tannic acid from Enrichment method 10 (Enrichment #10) after a single dose administration by oral gavage (p.o.) following a 7-day observation period.
Methods and Materials
Animal and Housing Conditions C57BL/6J male mice were group housed (3-5 mice per cage) with food and water available ad libitum in polysulfone ventilated cages (Alternative Design, AR, USA) in the animal rooms. The colony was maintained on a 12/12-h light/dark cycle at the temperature of 22±2° C. and all behavioral studies will be performed during the dark cycle. All animals used in this study were adult mice (at least 2.5 months of age).
Drug Administration Tannic acids were purchased from Sigma (Sigma tannic acid) or made from Enrichment method 10 (Enrichment #10). For Sigma tannic acid, the adult mice were randomly assigned to four groups: (1) control, (2) tannic acid (500 mg/kg), (3) tannic acid (750 mg/kg), and (4) tannic acid (1000 mg/kg) which were treated, respectively, by a vehicle control (ddH$_2$O), tannic acid at 500 mg/kg, tannic acid at 750 mg/kg and tannic acid at 1000 mg/kg. For Enrichment #10 tannic acid, the adult mice were randomly assigned to five groups: (1) control, (2) tannic acid (200 mg/kg), (3) tannic acid (500 mg/kg), (4) tannic acid (1000 mg/kg), and (5) tannic acid (2000 mg/kg) which were treated, respectively, by a vehicle control (ddH$_2$O), tannic acid at 200 mg/kg, tannic acid at 500 mg/kg, tannic acid at 1000 mg/kg and tannic acid at 2000 mg/kg. All mice were administrated with either the vehicle control or tannic acid by oral gavage (p.o.). Animals will be observed twice daily (a.m. and p.m.) or as often as needed during study periods for signs of mortality, morbidity, respiration, secretion, feces, and capability of water and food intake. The body weight of each mouse, which served as an index of its physical development and metabolism, was recorded daily throughout the study.
Results In Sigma tannic acid study, all mice received 1000 mg/kg Sigma tannic acid displayed inactivity, sternal recumbency, and altered respiration rate 35 minutes after dosing, and became moribund on day 2. The symptoms were not reversible during the study. One-third mice received 500 mg/kg or 750 mg/kg displayed sternal recumbency in 35 minutes after dosing. All mice received 500 mg/kg or 750 mg/kg survived during the study. The maximum tolerated dose of Sigma tannic acid was 750 mg/kg. In Enrichment #10 tannic acid study, all mice received 2000 mg/kg tannic acid displayed decreased activity, arching back, and heavy breathe immediately after dosing, and recovered in 10 minutes. No adverse effects were observed and the gross autopsy gave no significant finding in all groups. The maximum tolerated dose of Enrichment #10 tannic acid was at least 2000 mg/kg. In conclusion, enrichment #10 tannic acid showed a much higher maximum tolerated dose than Sigma tannic acid and is safer to be used as treatment for CNS and obesity disorders.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one of skill in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A composition, comprising (i) a mixture of tannic acids or a pharmaceutically acceptable salt thereof, and (ii) a carrier, wherein the composition contains less than 5% of tannic acids having less than four galloyl moieties, wherein the carrier comprises silicon dioxide and benzoic acid.

2. The composition of claim 1, wherein ≥98% of the tannic acids in the composition have 4-12 galloyl moieties.

3. The composition of claim 1, wherein ≥97% of the tannic acids in the composition have 5-12 galloyl moieties.

4. The composition of claim 1, wherein ≥90% of the tannic acids in the composition have 6-12 galloyl moieties.

5. The composition of claim 1, wherein ≥60% of the tannic acids in the composition have 8-12 galloyl moieties.

6. The composition of claim 1, wherein in the composition, about 10-20% of the tannic acids have 5 galloyl moieties, about 15-25% of the tannic acids have 6-7 galloyl moieties, and about 55-65% of the tannic acids have 8-12 galloyl moieties.

7. The composition of claim 1, wherein the composition is a pharmaceutical composition, a nutraceutical composition, a health food, or a medical food.

8. The composition of claim 7, wherein the composition is a tablet, a capsule, a soft chew, or gel.

9. A method for inhibiting D-amino acid oxidase (DAAO) in a subject, comprising administering to a subject in need thereof an effective amount of the composition of claim 1.

10. The method of claim 9, wherein the subject is a human patient having, suspected of having, or at risk for a central nervous system (CNS) disorder or a disorder associated with obesity.

11. The method of claim 10, wherein the human patient has, suspected of having, or at risk for a CNS disorder, which is selected from the group consisting of schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

12. The method of claim 10, wherein the human patient has, suspected of having, or at risk for a disorder associated with obesity, which is selected from the group consisting of eating disorders, anorexia nervosa, bulimia nervosa, stroke, coronary heart disease, heart attack, congestive heart failure, congenital heart disease, hypertension, non-alcoholic steatohepatitis, insulin resistance, hyperuricemia, hypothyroidism, osteoarthritis, gallstones, infertility, obesity hypoventilation syndrome, obstructive sleep apnea, chronic obstructed pulmonary disease, and asthma.

13. The method of claim 10, wherein the human patient has, suspected of having, or at risk for a disorder associated with obesity, which is an obesity disorder selected from the group consisting of diabetes, hyperglycemia, hyperlipidemia, and hypercholesterolemia.

14. The method of claim 9, wherein the subject is administered the composition at a frequency of three times a day to one time every two months.

15. The method of claim 10, wherein the subject is treated concurrently with, prior to, or subsequent to one or more additional pharmaceutical agents for treating the CNS disorder, or the disorder associated with obesity.

16. The composition of claim 1, wherein the composition contains less than 1% of tannic acids having less than four galloyl moieties.

17. The composition of claim 1, wherein the mixture of tannic acids is prepared by a process comprising extracting tannic acids from a plant source and removing tannic acids having less than four galloyl moieties.

* * * * *